United States Patent
Jur et al.

(10) Patent No.: US 10,064,270 B2
(45) Date of Patent: Aug. 28, 2018

(54) FLEXIBLE INTERCONNECTS, SYSTEMS, AND USES THEREOF

(71) Applicant: North Carolina State University, Raleigh, NC (US)

(72) Inventors: Jesse S. Jur, Raleigh, NC (US); Murat Yokus, Raleigh, NC (US); Rachel Foote, Raleigh, NC (US); Amanda Caton Myers, Raleigh, NC (US); Raj Pravinbhai Bhakta, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/174,677

(22) Filed: Jun. 6, 2016

(65) Prior Publication Data
US 2016/0358849 A1 Dec. 8, 2016

Related U.S. Application Data

(60) Provisional application No. 62/171,640, filed on Jun. 5, 2015, provisional application No. 62/173,044, filed on Jun. 9, 2015.

(51) Int. Cl.
| | |
|---|---|
| *H05K 1/02* | (2006.01) |
| *H01L 23/498* | (2006.01) |
| *H05K 1/18* | (2006.01) |
| *H05K 1/03* | (2006.01) |
| *H05K 3/36* | (2006.01) |
| *G01N 33/36* | (2006.01) |

(52) U.S. Cl.
CPC ....... *H05K 1/0283* (2013.01); *H01L 23/4985* (2013.01); *H01L 23/49883* (2013.01); *H05K 1/189* (2013.01); *G01N 33/367* (2013.01); *H05K 1/038* (2013.01); *H05K 3/361* (2013.01); *H05K 2201/0129* (2013.01); *H05K 2201/09263* (2013.01); *H05K 2201/10106* (2013.01); *H05K 2201/10219* (2013.01)

(58) Field of Classification Search
CPC ... H05K 1/0268; H05K 1/0393; H05K 1/0283
See application file for complete search history.

(56) References Cited

U.S. PATENT DOCUMENTS

| | | | | |
|---|---|---|---|---|
| 3,859,711 | A * | 1/1975 | McKiddy | G01R 31/2805 174/266 |
| 2005/0107501 | A1* | 5/2005 | Yasuhiro | C08J 5/00 524/115 |
| 2013/0016363 | A1* | 1/2013 | Iwamoto | G06F 3/046 356/616 |

OTHER PUBLICATIONS

M. Ciocchetti, C. Massaroni, P. Saccomandi, M. A. Caponero, A. Polimadei, D. Formica, and E. Schena, "Smart Textile Based on Fiber Bragg Grating Sensors for Respiratory Monitoring: Design and Preliminary Trials," Biosensors, vol. 5, No. 3, pp. 602-615, Sep. 2015.

Q. He, Z. Zeng, Z. Yin, H. Li, S. Wu, X. Huang, and H. Zhang, "Fabrication of Flexible MoS2 Thin-Film Transistor Arrays for Practical Gas-Sensing Applications," Small, vol. 8, No. 19, pp. 2994-2999, Oct. 2012.

(Continued)

*Primary Examiner* — Jeremy C Norris
(74) *Attorney, Agent, or Firm* — Thomas | Horstemeyer, LLP

(57) ABSTRACT

Provided herein are flexible interconnects, systems containing one or more flexible interconnects, and textiles including one or more flexible interconnects.

20 Claims, 42 Drawing Sheets

(56) References Cited

OTHER PUBLICATIONS

Y. He, W. Chen, X. Li, Z. Zhang, J. Fu, C. Zhao, and E. Xie, "Freestanding Three-Dimensional Graphene/MnO2 Composite Networks as Ultralight and Flexible Supercapacitor Electrodes," ACS Nano, vol. 7, No. 1, pp. 174-182, Jan. 2013.

Y. Cheng, R. Wang, J. Sun, and L. Gao, "Highly Conductive and Ultrastretchable Electric Circuits from Covered Yarns and Silver Nanowires," ACS Nano, vol. 9, No. 4, pp. 3887-3895, Apr. 2015.

C. Mattmann, O. Amft, H. Harms, G. Troster, and F. Clemens, "Recognizing Upper Body Postures using Textile Strain Sensors," in 2007 11th IEEE International Symposium on Wearable Computers, 2007, pp. 29-36.

K. Cherenack, C. Zysset, T. Kinkeldei, N. Münzenrieder, and G. Tröster, "Woven Electronic Fibers with Sensing and Display Functions for Smart Textiles," Adv. Mater., vol. 22, No. 45, pp. 5178-5182, Dec. 2010.

Y. Sun and J. A. Rogers, "Structural forms of single crystal semiconductor nanoribbons for high-performance stretchable electronics," J. Mater. Chem., vol. 17, No. 9, pp. 832-840, Feb. 2007.

S. P. Lacour, S. Wagner, Z. Huang, and Z. Suo, "Stretchable gold conductors on elastomeric substrates," Appl. Phys. Lett., vol. 82, No. 15, pp. 2404-2406, Apr. 2003.

T. Someya, Y. Kato, T. Sekitani, S. Iba, Y. Noguchi, Y. Murase, H. Kawaguchi, and T. Sakurai, "Conformable, flexible, large-area networks of pressure and thermal sensors with organic transistor active matrixes," Proc. Natl. Acad. Sci. U. S. A., vol. 102, No. 35, pp. 12321-12325, Aug. 2005.

H. C. Ko, M. P. Stoykovich, J. Song, V. Malyarchuk, W. M. Choi, C.-J. Yu, J. B. Geddes Iii, J. Xiao, S. Wang, Y. Huang, and J. A. Rogers, "A hemispherical electronic eye camera based on compressible silicon optoelectronics," Nature, vol. 454, No. 7205, pp. 748-753, Aug. 2008.

D. S. Gray, J. Tien, and C. S. Chen, "High-Conductivity Elastomeric Electronics," Adv. Mater., vol. 16, No. 5, pp. 393-397, Mar. 2004.

K. L. Lin and K. Jain, "Design and Fabrication of Stretchable Multilayer Self-Aligned Interconnects for Flexible Electronics and Large-Area Sensor Arrays Using Excimer Laser Photoablation," IEEE Electron Device Lett., vol. 30, No. 1, pp. 14-17, Jan. 2009.

H.-J. Kim, C. Son, and B. Ziaie, "A multiaxial stretchable interconnect using liquid-alloy-filled elastomeric microchannels," Appl. Phys. Lett., vol. 92, No. 1, p. 011904, Jan. 2008.

F. Bossuyt, T. Vervust, and J. Vanfleteren, "Stretchable Electronics Technology for Large Area Applications: Fabrication and Mechanical Characterization," IEEE Trans. Compon. Packag. Manuf. Technol., vol. 3, No. 2, pp. 229-235, Feb. 2011.

Y.-Y. Hsu, M. M Gonzalez, F. Bossuyt, J. Vanfleteren, and I. De Wolf, "Polyimide-Enhanced Stretchable Interconnects: Design, Fabrication, and Characterization," IEEE Trans. Electron Devices, vol. 58, No. 8, pp. 2680-2688, Aug. 2011.

N. Lu, C. Lu, S. Yang, and J. Rogers, "Highly Sensitive Skin-Mountable Strain Gauges Based Entirely on Elastomers," Adv. Funct. Mater., vol. 22, No. 19, pp. 4044-4050, Oct. 2012.

S. Lee, S. Shin, S. Lee, J. Seo, J. Lee, S. Son, H. J. Cho, H. Algadi, S. Al-Sayari, D. E. Kim, and T. Lee, "Ag Nanowire Reinforced Highly Stretchable Conductive Fibers for Wearable Electronics," Adv. Funct. Mater., vol. 25, No. 21, pp. 3114-3121, Jun. 2015.

Q. Li and X. Tao, "A stretchable knitted interconnect for three-dimensional curvilinear surfaces," Text. Res. J., vol. 81, No. 11, pp. 1171-1182, Jul. 2011.

Q. Li and X. M. Tao, "Three-dimensionally deformable, highly stretchable, permeable, durable and washable fabric circuit boards," Proc. R. Soc. Lond. Math. Phys. Eng. Sci., vol. 470, No. 2171, p. 20140472, Nov. 2014.

T. H. J. van Osch, J. Perelaer, A. W. M. de Laat, and U. S. Schubert, "Inkjet Printing of Narrow Conductive Tracks on Untreated Polymeric Substrates," Adv. Mater., vol. 20, No. 2, pp. 343-345, Jan. 2008.

M. Suh, K. E. Carroll, E. Grant, and W. Oxenham, "Effect of fabric substrate and coating material on the quality of conductive printing," J. Text. Inst., vol. 104, No. 2, pp. 213-222, Feb. 2013.

B. Karaguzel, C. R. Merritt, T. Kang, J. M. Wilson, H. T. Nagle, E. Grant, and B. Pourdeyhimi, "Flexible, durable printed electrical circuits," J. Text. Inst., vol. 100, No. 1, pp. 1-9, Mar. 2009.

S. Takamatsu, T. Lonjaret, E. Ismailova, A. Masuda, T. Itoh, and G. G. Malliaras, "Wearable Keyboard Using Conducting Polymer Electrodes on Textiles," Adv. Mater., p. 4485-4488, Nov. 2015.

K.-S. Kim, K.-H. Jung, and S.-B. Jung, "Design and fabrication of screen-printed silver circuits for stretchable electronics," Microelectron. Eng., vol. 120, pp. 216-220, May 2014.

N. Matsuhisa, M. Kaltenbrunner, T. Yokota, H. Jinno, K. Kuribara, T. Sekitani, and T. Someya, "Printable elastic conductors with a high conductivity for electronic textile applications," Nat. Commun., vol. 6, p. 7461, Jun. 2015.

M. A. Yokus and J. S. Jur, "Fabric-Based Wearable Dry Electrodes for Body Surface Biopotential Recording," IEEE Trans. Biomed. Eng., vol. 63, No. 2, pp. 423-430, Feb. 2016.

\* cited by examiner

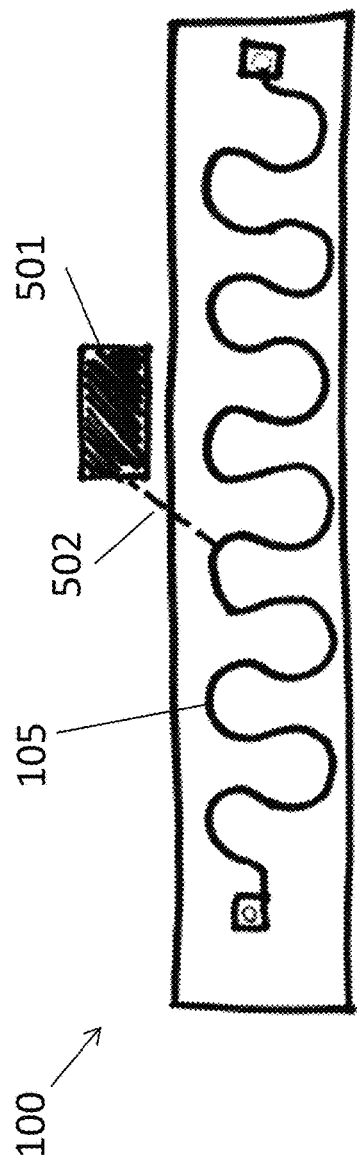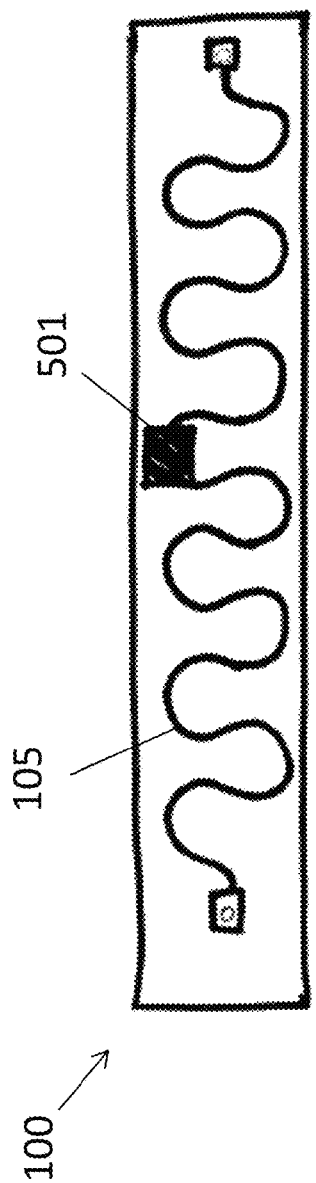

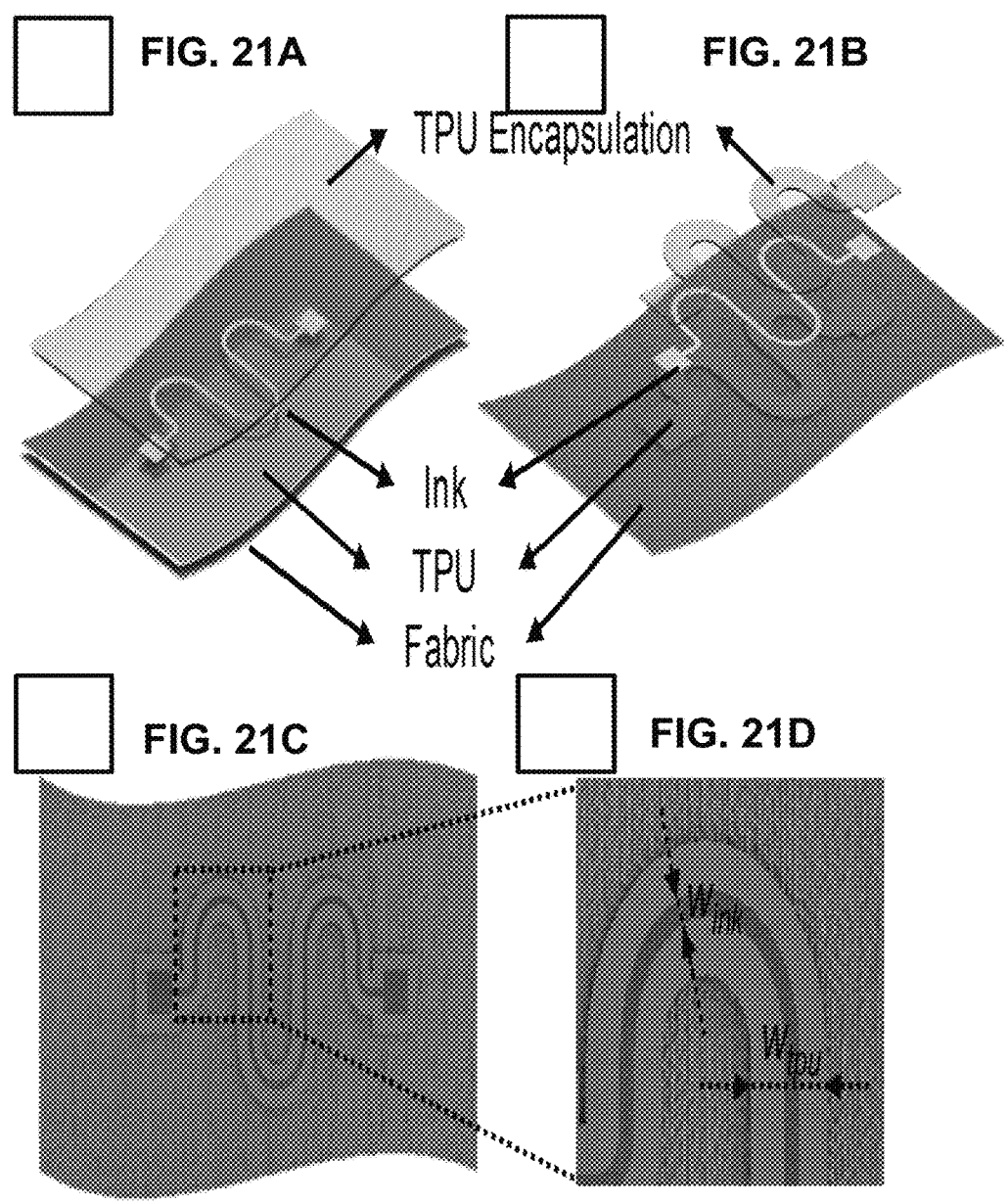

w: width    R: radius
l: arm length    α: angle

FIG. 22F

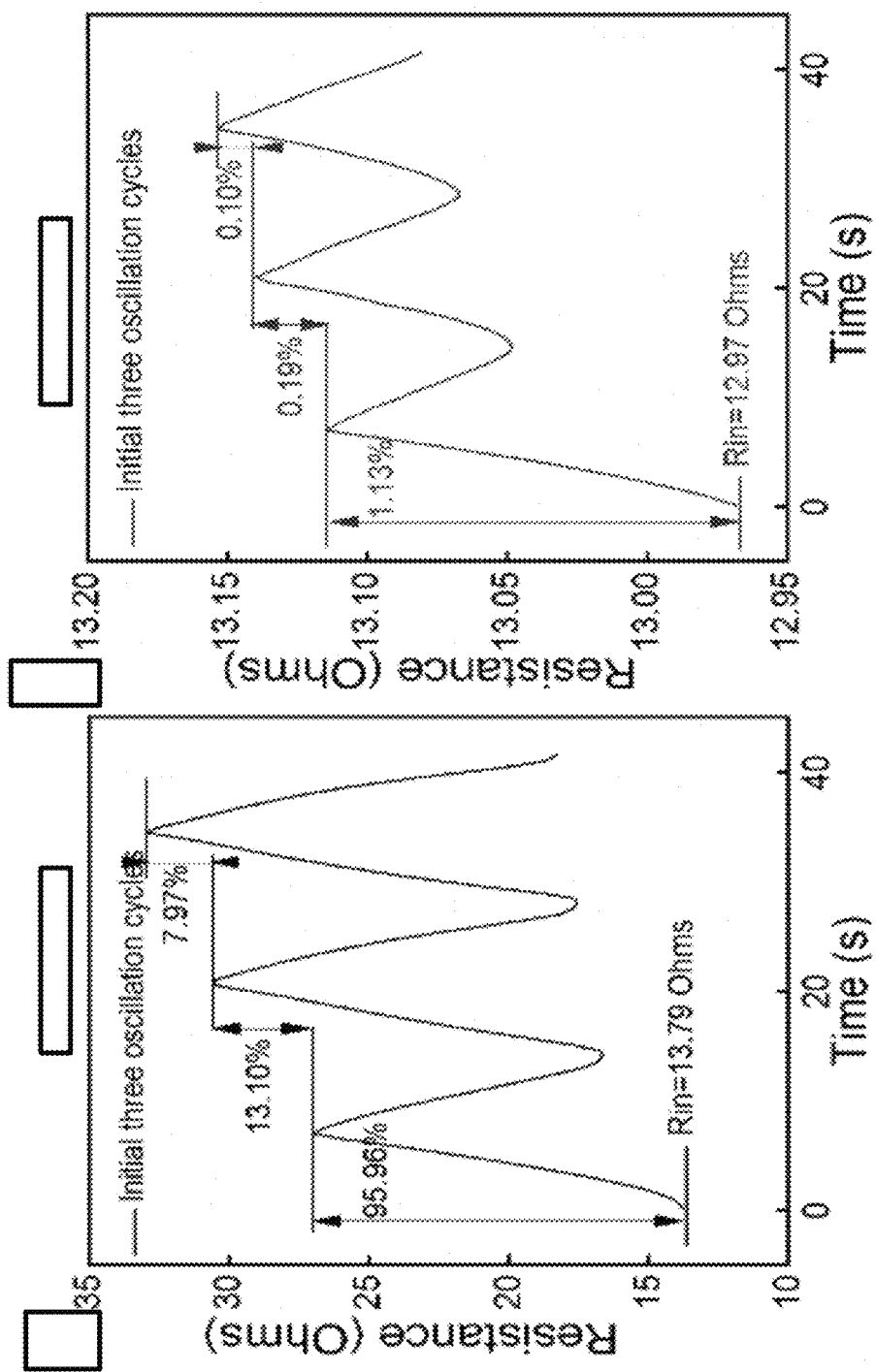

|  | D2 | D3 | D4 | E1 | E2 | E3 |
|---|---|---|---|---|---|---|
| Length (mm) | 134.36 | 135.71 | 131.63 | 139.10 | 130 | 133.84 |
| Height (mm) | 15.76 | 17.5 | 19.78 | 12.94 | 17 | 20.46 |
| α (°) | 20 | 30 | 45 | -20 | 0 | 20 |
| l (mm) | 0 | 0 | 0 | 5 | 5 | 5 |
| w (mm) | 1 | 1 | 1 | 1 | 1 | 1 |

FIG. 32

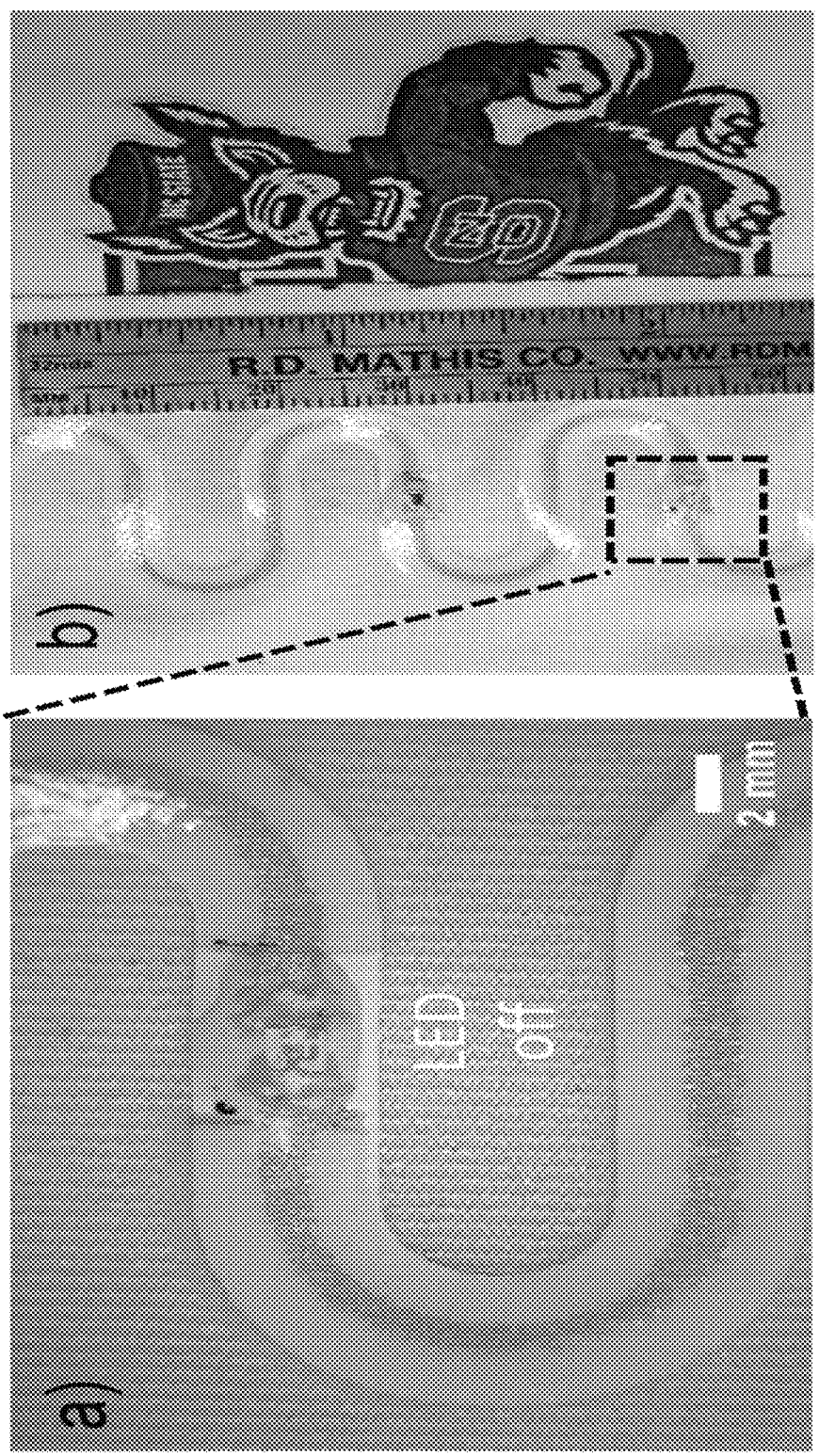

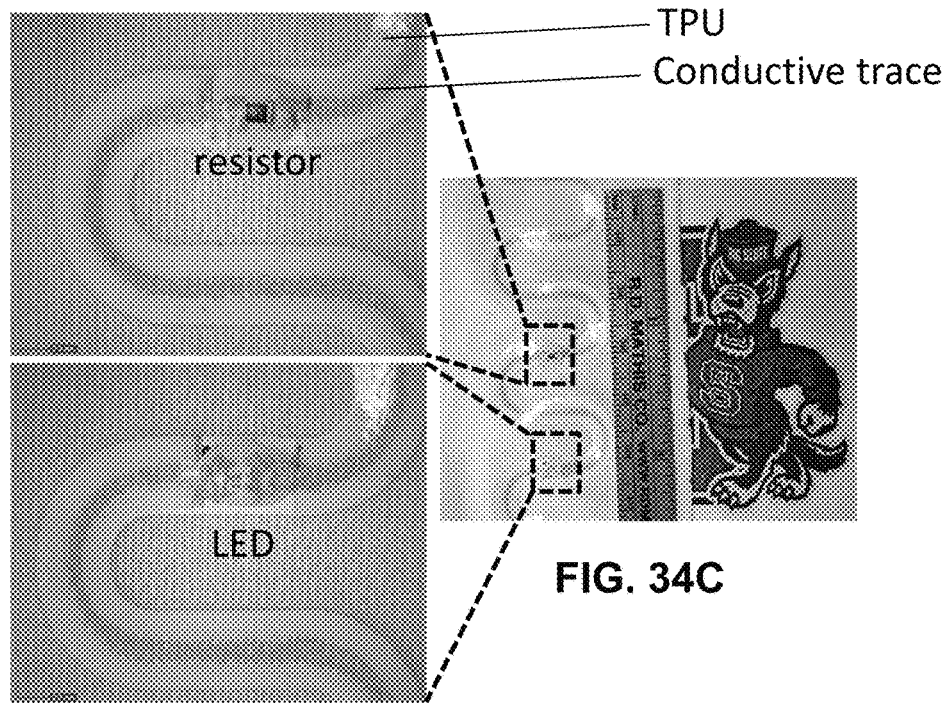
FIG. 34A
FIG. 34B
FIG. 34C
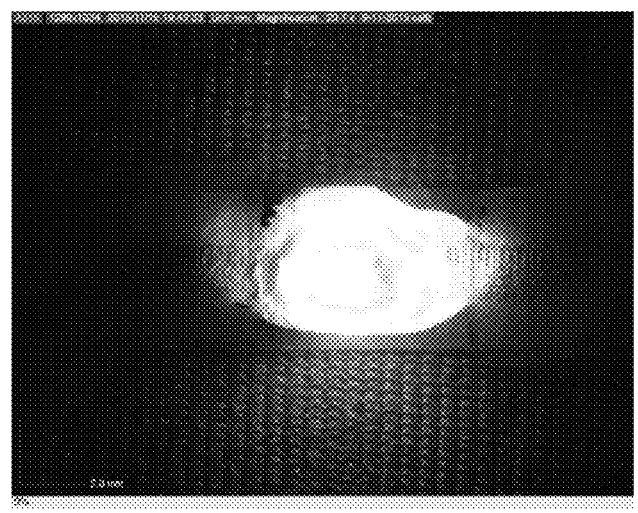
FIG. 35

FLEXIBLE INTERCONNECTS, SYSTEMS, AND USES THEREOF

CROSS-REFERENCE TO RELATED APPLICATIONS

This application claims the benefit of and priority to co-pending U.S. Provisional Patent Application No. 62/171,640, filed on Jun. 5, 2015, entitled "FLEXIBLE INTERCONNECTS, SYSTEMS, AND USES THEREOF," and co-pending U.S. Provisional Patent Application No. 62/173,044, filed on Jun. 9, 2015 entitled "FLEXIBLE INTERCONNECTS, SYSTEMS, AND USES THEREOF," the contents of which are incorporated by reference herein in its entirety.

STATEMENT REGARDING FEDERALLY SPONSORED RESEARCH OR DEVELOPMENT

This invention was made with government support under grant number 1160483 awarded by the National Science Foundation. The government has certain rights to this invention.

BACKGROUND

Electronic textiles have widespread application and use in diverse fields such as healthcare, fitness, sensors, and energy harvesting. The vast potential of electronic textiles remains to be tapped. As such, there is an urgent and increasing need for improved electronic textiles.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 5A-5B show embodiments of a flexible interconnect that include an electrical component.

FIGS. 21A-21D show an embodiment of a multilayer stretchable interconnect. FIG. 21A Whole area TPU film lamination and TPU film encapsulation, FIG. 21B shows an embodiment of a meandering shaped TPU film lamination and TPU film encapsulation, FIG. 21C shows a top view of laminated and encapsulated structure, and FIG. 21D shows close-up picture of meandering line.

FIGS. 22A-22J show (FIG. 22A) embodiments of meandering line design parameters (w, l, R, α), (FIG. 22B) resistance vs. strain behavior of the printed straight lines (width: 3 mm, length: 14 cm) on both knit fabric and TPU printing layer, (FIG. 22C), (FIG. 22D), (FIG. 22E), (FIG. 22F) digital microscope pictures of printed meandering and straight lines on knit fabric, (FIG. 22G), (FIG. 22H), (FIG. 22I), (FIG. 22J) digital microscope pictures of printed meandering and straight lines on TPU printing layer.

FIGS. 27A-27D show graphs demonstrating results of a cycling test of multilayer interconnect structure (test speed: 10.16 cm/min). FIG. 27A shows whole area TPU lamination and encapsulation. FIG. 27B shows meandering line shaped (offset-cut) TPU lamination and encapsulation. FIG. 27C shows the initial three cycles of FIG. 27A. FIG. 27D shows the initial three cycles of FIG. 27B.

FIG. 32 shows Block D2-E3 meandering line design parameters.

FIGS. 33A-33D show (FIG. 33A) a close up picture of LED integrated printed stretchable line, (FIG. 33B) a LED integrated stretchable line, (FIG. 33C) a cross-sectional view of LED integration, and (FIG. 33D) LED intensity with stretching. Inset of 33D: Stretched LED integrated printed line.

FIGS. 34A-34C show (FIGS. 34A-34B) a close up picture of LED integrated printed stretchable line having an integrated resistor (FIG. 34A) and an integrated LED (FIG. 34B) and a picture of the stretchable line (FIG. 34C).

FIG. 35 shows an image of the LED light of FIG. 34B lighting up when electricity is conducted through the conductive trace of the printed stretchable line.

DETAILED DESCRIPTION

Figure 1A:
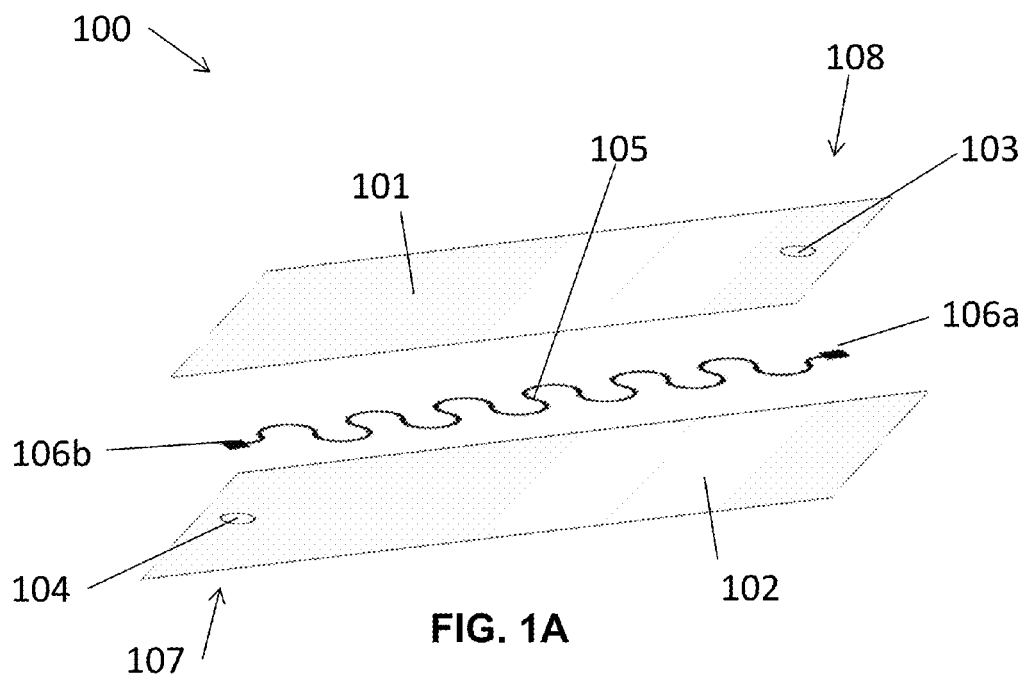
FIGS. 1A-1B show several views of one embodiment of a flexible interconnect.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, textile engineering, electrical engineering, and the mechanical arts.

Definitions

As used herein, "thermoplastic material" refers to a polymer that becomes pliable, moldable, and/or liquid above a threshold temperature and hard and/or solid when cold.

As used herein, "thermoset polymer" refers to a polymer based material made of monomers that polymerize (cure) when heated, subjected to a chemical reaction, or irradiated (e.g. exposure to UV light). Thermoset materials are typically liquid or malleable prior to curing.

As used herein, "conductive ink" refers to a material that can conduct electricity and can be molded into shapes and patterns and when set or dry results in an object or conduit.

As used herein, "about," "approximately," and the like, when used in connection with a numerical variable, generally refers to the value of the variable and to all values of the variable that are within the experimental error (e.g., within the 95% confidence interval for the mean) or within +−10% of the indicated value, whichever is greater.

As used herein, "electrical component" refers to any basic discrete device or physical entity in an electronic system, and includes without limitation to semiconductors, diodes, transistors, integrated circuits, optoelectronic devices (e.g. LEDs, OLEDS, opto-isolators, opto-couplers, photo-couplers, photodiodes, PJT, JFET, SCR, TRIAC, Zero-crossing, TRIAC, open collector, CMOS, IC, solid state relays, opto switch, opto interrupter, optical switchm optical interrupter, photo switch, photo interrupter), battery, fuel cell, power supply, photo voltaic device, thermoelectric generator, piezoelectric sensor or circuit, Van de Graff generator, resistors (e.g. power resistor, SIP, DIP resistor networks, Rheostat, potentiometer, trim pot, thermistor, humistor, photoresistor, memristor, varistor, voltage dependent resistor, MOV, resistance wire, Nichrome wire, heating element, capacitor (e.g. integrated capacitors, fixed capacitors, variable capacitors, special capacitors (e.g. power, safety, filter, light-emitting, motor, photoflash, and reservoir capacitors), capacitor networks/arrays), vricap diodes, inductors (e.g. coil, choke, variable inductor, saturable inductor, transformer, magnetic amplifier, ferrite impedances, beads solenoid, microphone), RC networks, LC networks, transducers, sensors (e.g. gas sensors, liquid sensor, chemical sensors, biomolecule sensors, and the like). LVDTs, rotary encoder, inclinometer, motion sensor, flow meter, strain gauge (e.g. piezoelectric or resistive), accelerometer, RTD, bolometer, thermal cutoff switch, thermocouple, thermopile, magnetometer, hygrometer, terminals, connectors, ultrasonic motors, piezoelectric devices, switch (e.g. SPST, SPDT, DPST, DPDT, NPNY, humidistat, thermostat, reed switch, relay, centrifugal switch, mercury switch, limit switch, micro switch, knife switch), fuse, and optical fiber and other waveguides. Other electrical components will be instantly appreciated by those of skill in the art. When coupled to or otherwise integrated with the flexible interconnects provided herein, the electrical component(s) can have any number of connection points to the flexible interconnect as practically implementable, which will be appreciated by those of ordinary skill in the art. It will also be immediately appreciated that the electrical component(s) can have one or more connection points to one or more than one (multiple) flexible interconnect(s).

Discussion

Wearable electronics have been the focus of attention for researchers in the last couple decades. There is a significant growing interest in this field ranging from unobtrusive textile integrated bio-sensors, to electrochromic displays embedded into textiles. Current research focuses on the use of nanotechnology, organic materials, and innovative fabrication techniques to create flexible electronic devices such as sensors, supercapacitors, conductive yarns, and energy harvesting devices. These flexible devices are designed to bend and flex to form on curvilinear surfaces, which make them suitable for integration into textiles. The unobtrusive integration of discrete flexible devices into textiles creates a new norm for wearable technology, i.e., a smart garment.

There are several characteristics to be considered when creating a wearable smart garment, including air and vapor permeability biocompatibility, comfort, washing and chemical (e.g., detergent) resistance, and ease of deformation (bending, compression, extension etc.). Electro-mechanical durability of the smart garment when subjected to large strains is also important to consider in determining the endurance of the garment to the dynamic forces of body movement. Prior research has shown that fabrics may experience up to ~20% strain during a set of various physical activities. Electronics positioned various locations of the fabric will undergo this range of deformation from the body's movement. Ideally, this deformation needs to happen through stretchable interconnects between the less resilient, hard electronic components. Therefore, the design of stretchable interconnects is important for maximizing the functionality while at the same time accommodating larger strains without constraining body movement for human comfort.

In order to provide stretchability without diminishing the functionality of electronic devices, various fabrication methods and stretchable material structures have been studied. Fabrication of wavy or buckled single crystal semiconductor nanoribbons or metals (e.g., gold) by pre-straining the elastomeric substrate, and mesh-shaped structures yielded electronic component (e.g., thin film transistors and transistor-based pressure sensors) functionalities up to 25% strain values by undergoing out-of-plane deformation. These techniques have yielded hemispherical electronic eye cameras based on an array of silicon photodetectors. However, the methods require complex component transferring and mechanical pre-straining the polymeric substrate. A different approach to make stretchable interconnects is to fabricate planar horseshoe shaped structures by lithographically patterning gold on elastomeric substrates. Failure strain of 54% and cyclic endurance of 200 cycles at 25% strain have been achieved. Moreover, a photoablation method was utilized to fabricate rectilinear and meandering interconnect designs. Its fabrication process used metal layers for polymer masking; therefore, eliminating the alignment process and use of chemicals for etching. However, the presence of conical defects was stated to have an effect on the stretchability of the meandering lines. A failure strain of 50% with a resistance change ($\Delta R/R$) of 5% was shown. As an alternative method for stretchable interconnects, liquid alloy filled elastomeric micro-channels were studied. This technique did not result in a crack formation, which is commonly encountered in metals upon elongation above 1%, due to the presence of alloy metal in liquid form at room temperature. Resistance change ($\Delta R$) of 0.24$\Omega$ with 100% strain was indicated, but lower stretchability (~30%) was observed when active circuit elements were integrated into liquid metal filled micro-channels. Furthermore, an in-plane metal conductor technology for horseshoe shaped meandering lines was proposed by to pattern copper with a polyimide support underneath. The polyimide support layer increased the fatigue life (3,400 cycles at 10% strain) of the meandering line. The fatigue life was further increased to 40,000 cycles at 30% strain by the addition of a supporting polyimide layer on top of the copper layer.

More recently, notable research has been done in nanomaterial research and development to fabricate stretchable interconnects. Carbon nanotubes (CNTs) and carbon black (CB) filled elastomers were developed toward the fabrication of strain gauges. It was shown that CB filled elastomers had $\Delta R/R$ of ~140% at 5% strain because of separation of carbon particles with applied strain, which produced breakage of the conductive pathways. Likewise, serpentine shaped CNT filled elastomers had a $\Delta R/R$ of ~5% at 15% strain due to rotation and slide of CNTs against each other upon applied strain. In another study, silver nanowires (AgNWs) and silver nanoparticles (AgNPs) embedded in an elastomeric matrix had $\Delta R/R$ of ~2 after 1,000 cycles with 10% strain, which was attributed to AgNW breakage with high number of cycles. Even though some of the aforementioned methods and novel materials show excellent stretchability and endurance results, their manufacturing complexity, material cost, and scalability limit their usage in mass production of wearable electronics. For example, the current market price of CNTs and AgNWs is relatively expensive than conductive inks, which limits their usage to only nano-based applications rather than large-scale fabrications.

Other large-scale mass-production techniques such as knitting and weaving have been used in integration of electronic functionality into smart garments. Knitting polyurethane covered copper fibers with conventional yarns yielded 1% resistance change up to 300% strain values. Screen-printing of the conductive inks, on the other hand, is an alternative industry scalable technique for fabrication of inexpensive electronic components action and removal steps as commonly found in semiconductor fabrication processes. Printing of various silver inks has been investigated on polyarylate films, woven and knitted fabrics, and nonwoven fabrics. However, the electromechanical properties of the printed lines as a function of stretching were not investigated. On the other hand, a brush painting of poly(3,4-ethylenedioxythiophene):poly(styrene sulfonate) (PEDOT:PSS) conducting polymer on knitted fabrics was studied, reporting an elastic stretchability up to 30%. The resistance change after 1000 stretching cycles with 20% strain was about 10%. Screen-printing of horseshoe shaped silver ink on TPU films was studied in, and 7% stretchability value was reported. Finally, another study showed development and printing of a new ink material with stretchability of >93% and endurance of 1,000 cycles at 30% strain. However, the design and optimization of the printed conductive meandering lines on films, its subsequent integration onto textile wearables, and the effect of stretching on the electrical properties of the printed lines were not studied thoroughly before. Addressing these matters will shed light on some of the challenges (e.g. interconnect reliability under large strains, electronics integration, and washability) in textile-based electronics.

With the limitations of current electronic textiles in mind, described herein are flexible interconnects that contain a conductive trace that can be encapsulated between two or more thermoplastic polymer films. The flexible interconnects described herein can be coupled to or otherwise included or integrated with a textile. In some embodiments, two or more of the flexible interconnects described herein can be electrically and/or physically coupled to one another through conductive pads that can be exposed through via hole(s) in one or more of the thermoplastic polymer films. Also described herein are textiles incorporating one or more of the flexible interconnects described herein. The flexible interconnects and systems thereof can result in electronic and smart textiles with improved durability. Further, full encapsulation of the conductive trace can allow for completely hidden electronic systems on textiles, which can satisfy privacy concerns.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Figure 1B:
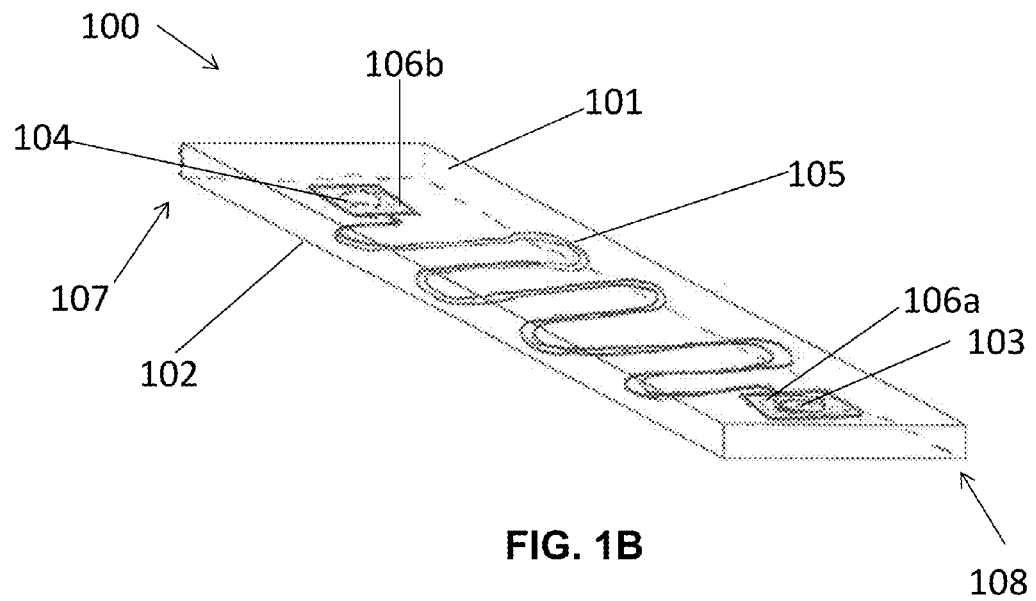
Figure 2:
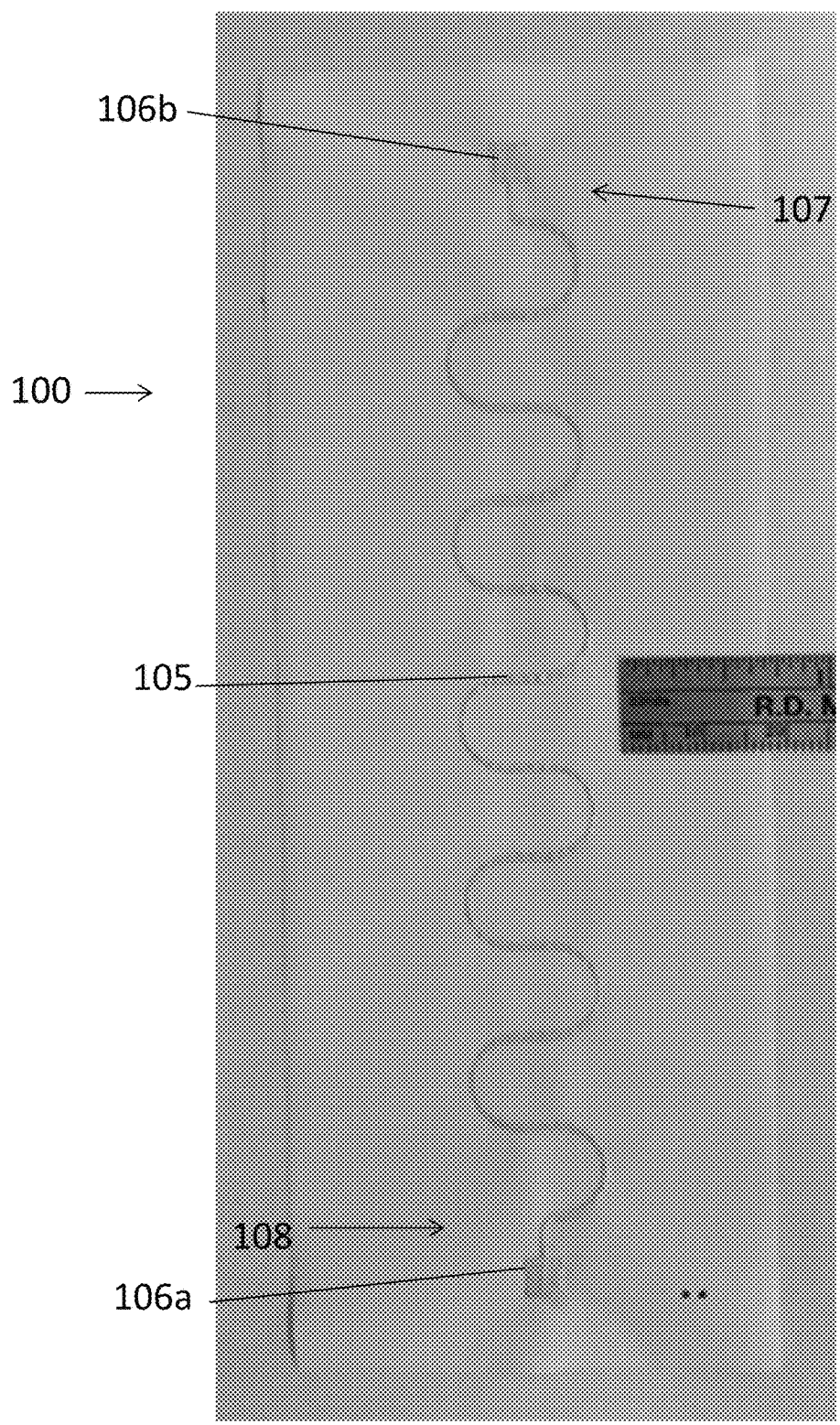
FIG. 2 shows an image of one embodiment of a flexible interconnect.

With a general description of the devices and systems described herein, attention is directed to FIGS. 1A-1B and 2, which show several views of one embodiment of a flexible interconnect. FIG. 1A shows an exploded view of the flexible interconnect, while FIGS. 1A and 2 show embodiments of the assembled flexible interconnect. In some embodiments, all the individual components of the flexible interconnect are flexible. The flexible interconnect 100 can have a first thermoplastic polymer film 101 that forms the top layer of the flexible interconnect. The first thermoplastic polymer film 101 can have a first hole 103. The flexible interconnect 100 can have a second thermoplastic polymer film 102 that forms the bottom layer of the flexible interconnect 100. The second thermoplastic polymer film 102 can have a second hole 104. The first and the second thermoplastic polymer films can be made from any suitable thermoplastic polymer. Suitable thermoplastic polymers include, without limitation, polyurethane, polyethylene, vinylester, epoxys, polyamides, polypropylene, polyethylene terephthalate, polybutylene terephthalate, polyetherimide, polyvinylidene fluoride, polyetheretherketone, Poly (Acrylonitrile Butadiene Styrene) (ABS), polylactic acid (PLA), polycarbonate, polyvinyl chloride silicones, and any permissible combinations or copyolymers thereof. In some embodiments, the thermoplastic polymer film can be a composite material that can include any of the suitable thermoplastic polymer materials previously listed and one or more suitable filler material. Suitable filler materials can include organic and inorganic materials, such as, but not limited to, carbon nanotubes (CNTs), metal particles (e.g. Ag particles), graphene, nanowires (e.g. Ag nanowires), cellulose and the like.

The thermoplastic films can be any shape or size. In some embodiments, the shape can be rectangular, circular, triangular, or irregular. In some embodiments, the shape of the thermoplastic films are not the same shape as the conductive trace (See e.g. at least FIG. 2). In some embodiments, they can follow the shape of the conductive trace. In other words, they can be the same shape as the conductive trace and/or conductive pads (discussed below) but only slightly larger (e.g. about 1 µm to about 30 mm) in any or all dimensions as the conductive trace and/or conductive pads (See e.g. at least FIGS. 21A-21D). By constructing the flexible interconnect such that thermoplastic films are the same shape as the conductive trace can improve the performance and/or durability of the flexible interconnect and/or textile that they can be incorporated into.

The flexible interconnect 100 can have a conductive trace 105. The conductive trace can be made from any suitable conductive ink. Suitable conductive inks include, without limitation, silver, carbon, silver chloride, silver/silver chloride, gold, and combinations thereof. Other suitable conductive inks include, without limitation, dielectric inks, silver plated copper inks, and positive temperature coefficient inks. The conductive trace can be configured in or contain any shape or design (e.g., without limitation, curved lines, straight lines, zig-zag, sinusoid, horseshoe, and combinations thereof) that falls within the design parameters. Design parameters are discussed in greater detail in reference to FIGS. 3A-3D. FIGS. 1A-1B and 2 show one embodiment of a conductive trace having a meandering sinusoid pattern comprising palindromic horseshoe shaped repeating units. The total length of the conductive trace can be any suitable length desired and will depend on inter alia, textile, conductive ink, conductive pads, and/or conductive trace used and/or the particular application of the flexible interconnect and/or electronic textile. In some embodiments the total length of the conductive trace can range from about 1 mm to about 300 mm. In other embodiments, the total length of the conductive trace can be greater than 300 mm. One of ordinary skill in the art will appreciate the practical upper boundary of the length in any instance and can be based on, inter alia, application of the conductive trace, textile used, and durability desired.

The conductive trace can have a conductive pad electrically coupled to each end 106a, 106b (collectively 106). In some embodiments, the conductive pads 106 are integrated extensions of the conductive trace 105. In other words, the conductive pads 106 can be made of the same conductive ink and are seamless extensions of the conductive trace 105.

The flexible interconnect can be configured such that the conductive pads 106 are aligned with and in physical contact with the first hole 103 and the second hole 104 present in the first thermoplastic polymer film 101 and the second thermoplastic polymer film 102, respectively. Thus, the conductive pads 106 can be exposed through the first and the second thermoplastic polymer films 101, 102. In some embodiments, during manufacture of the flexible interconnect 100, the conductive ink that can be used to form the conductive trace 105 and/or conductive pads 106 can fill the holes 103, 104. In any instance, the exposed conductive pads 106 can facilitate an electronic via between two or more flexible interconnects 100 and/or a flexible interconnect 100 and an electrical component.

As shown in FIGS. 1A-1B and 2, in some embodiments, the holes 103, 104 can be placed at one end of the first and the second thermoplastic polymer film 101, 102, respectively, where when the flexible interconnect is assembled the holes 103, 104 are at opposite ends from one another. In these embodiments, when the conductive pads 106 are aligned with the holes, each side of the flexible interconnect 100 has an exposed conductive pad. In this way, a flexible interconnect 100 with a "plus" end (e.g. 107) and a "minus" end (e.g. 108) can be manufactured.

The conductive trace 105 and conductive pads 106 (except for any exposed surface of the conductive pads 106 are encapsulated between the first and the second thermoplastic polymer film 101, 102.

Figures 3C, 3D:
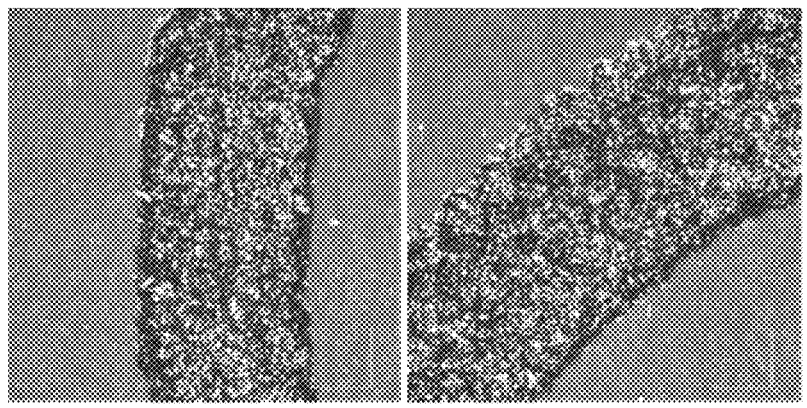
FIGS. 3A-3D show several views of a region of a conductive trace.
Figure 3B:
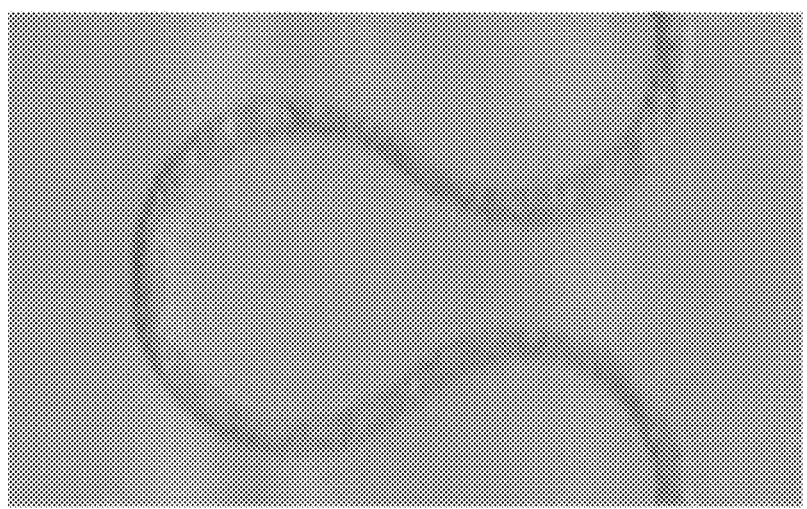
Figure 3A:
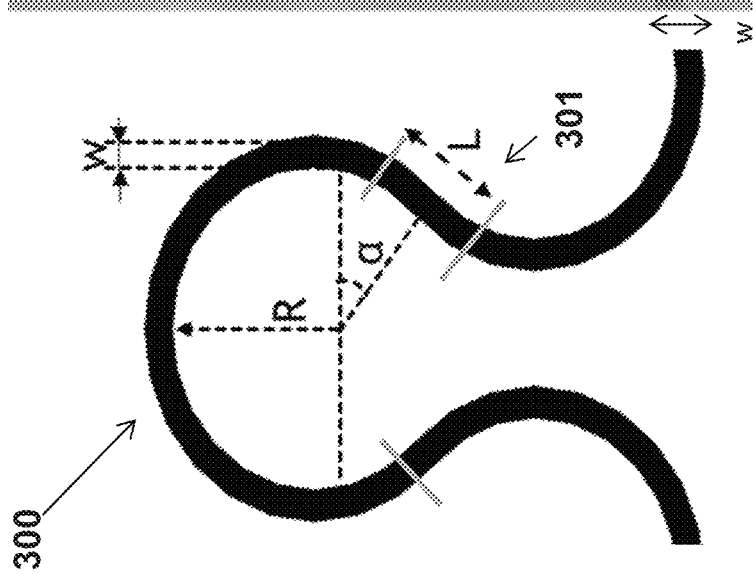

Attention is directed to FIGS. 3A-3D, which demonstrate aspects of the conductive trace in greater detail. FIG. 3A shows a cartoon demonstrating design parameters for the conductive trace of a segment of the conductive trace, using the repeating unit 300 of the conductive trace pattern shown in FIG. 1A as an example. The conductive trace can have a width w. The repeat unit 300 of the sinusoidal conductive trace of FIG. 1A can have a radius, R, which corresponds to the radius of a circle that can be superimposed on the horseshoe portion of the repeat unit 300. The repeat unit 300 can have a leg 301 having a leg length, L. The leg corresponds to the portion of the repeat unit that extends between the superimposed circle and the superimposed circle of the next repeat unit. α or θ is the angle at which the leg connects to the horseshoe portion of the repeat unit 300. One of skill in the art will appreciate that the exact dimension of the design parameters will vary depending, inter alia, on the textile, conductive ink, conductive pads, and/or conductive trace used and/or the particular application of the flexible interconnect and/or electronic textile. In some embodiments, R can range from about 0 mm to about 20 mm. In some embodiments, α can range from about 0° to about 180°. In some embodiments, L can range from about 0 mm to about 10 mm. In some embodiments, w can range from about 0.01 mm to about 30 mm.

Figure 4B:
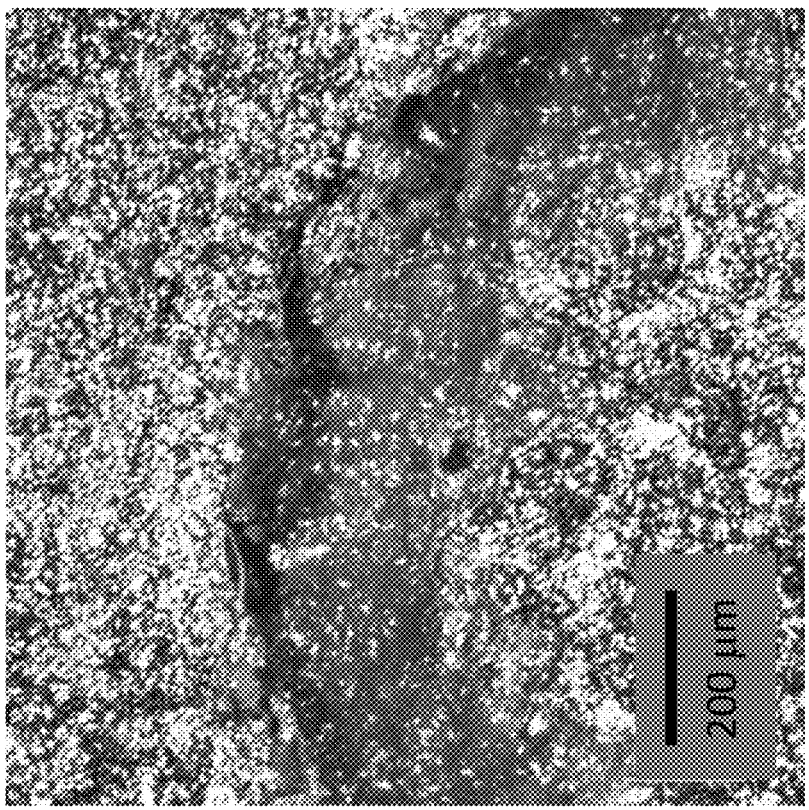
FIGS. 4A-4B show scanning electron microscope images of one embodiment of a conductive pad in physical contact with a hole (or via) in a thermoplastic polymer layer of the flexible interconnect.
Figure 4A:
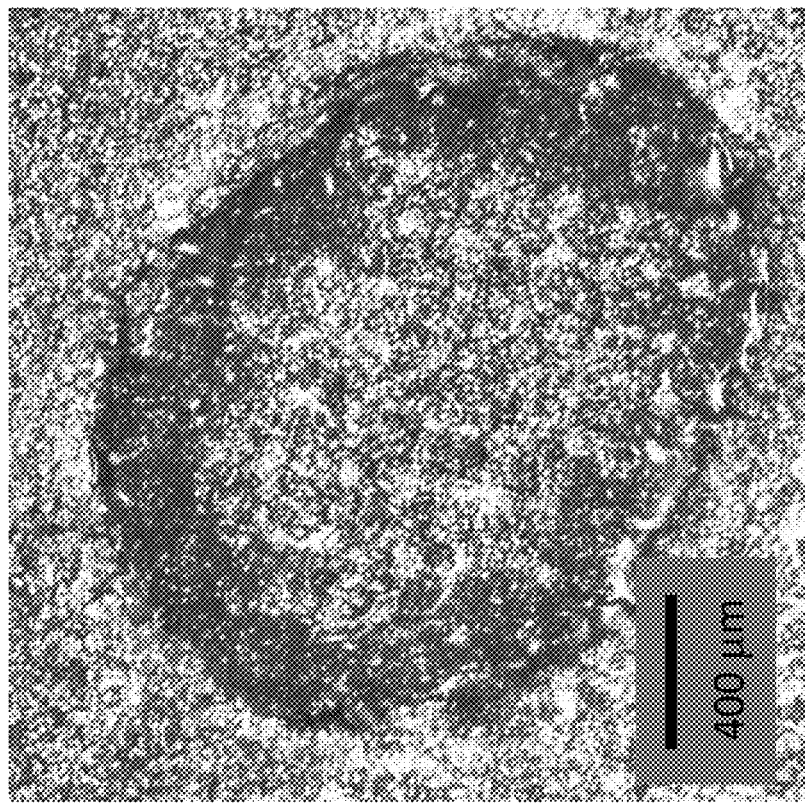

FIG. 3B shows an image of the repeat unit 300 of the conductive trace cartooned in FIG. 3A. FIGS. 3C and 3D show microscopic images of the conductive trace. FIGS. 4A and 4B show microscopic images of a conductive pad in physical contact with a hole (103, 104) of the first or the second thermoplastic polymer film (101, 102) two different magnifications.

As shown in FIGS. 5A and 5B, the flexible interconnect 100 can also include one or more electrical components 501 electrically coupled to the conductive trace 105. As shown in FIG. 5B, the electrical component 501 can also be encapsulated between the two or more thermoplastic polymer films. As shown in FIG. 5A, the electrical component 501 can be outside of between the two or more thermoplastic polymer films. Where the electrical component 501 is outside of the two or more thermoplastic polymer films, a suitable electrical conduit 502 can extend through the first or the second thermoplastic polymer film and electrically couple the conductive trace 105 and/or an encapsulated electrical component (not shown) and the outside electrical component 501. Suitable electrical conduits include, but are not limited to, wires, conductive ink, waveguides (including air and optical fibers).

Electrical component(s) can be electrically or otherwise coupled to one or more ends, such as to one or more of the conductive pads, of the flexible interconnect. Electrical component(s) can be electrically or otherwise coupled to the conductive trace, such as being spliced into the conductive trace, of the flexible interconnect. In some embodiments, the flexible interconnect can contain electrical components coupled to the flexible interconnect both at one or more ends and directly to the conductive trace.

Figure 6:
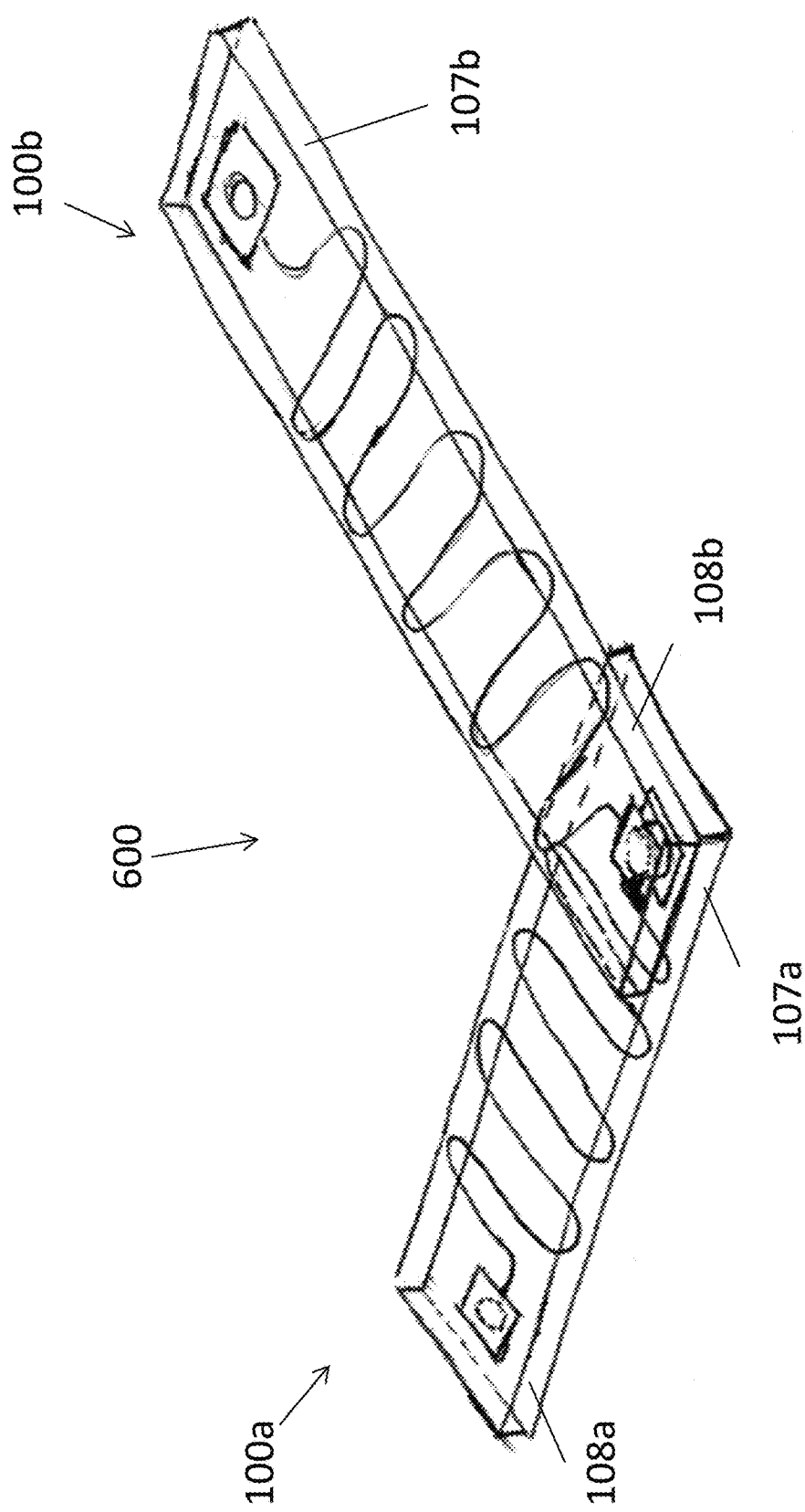
FIG. 6 shows one embodiment of a system that includes a flexible interconnect.
Figure 7:
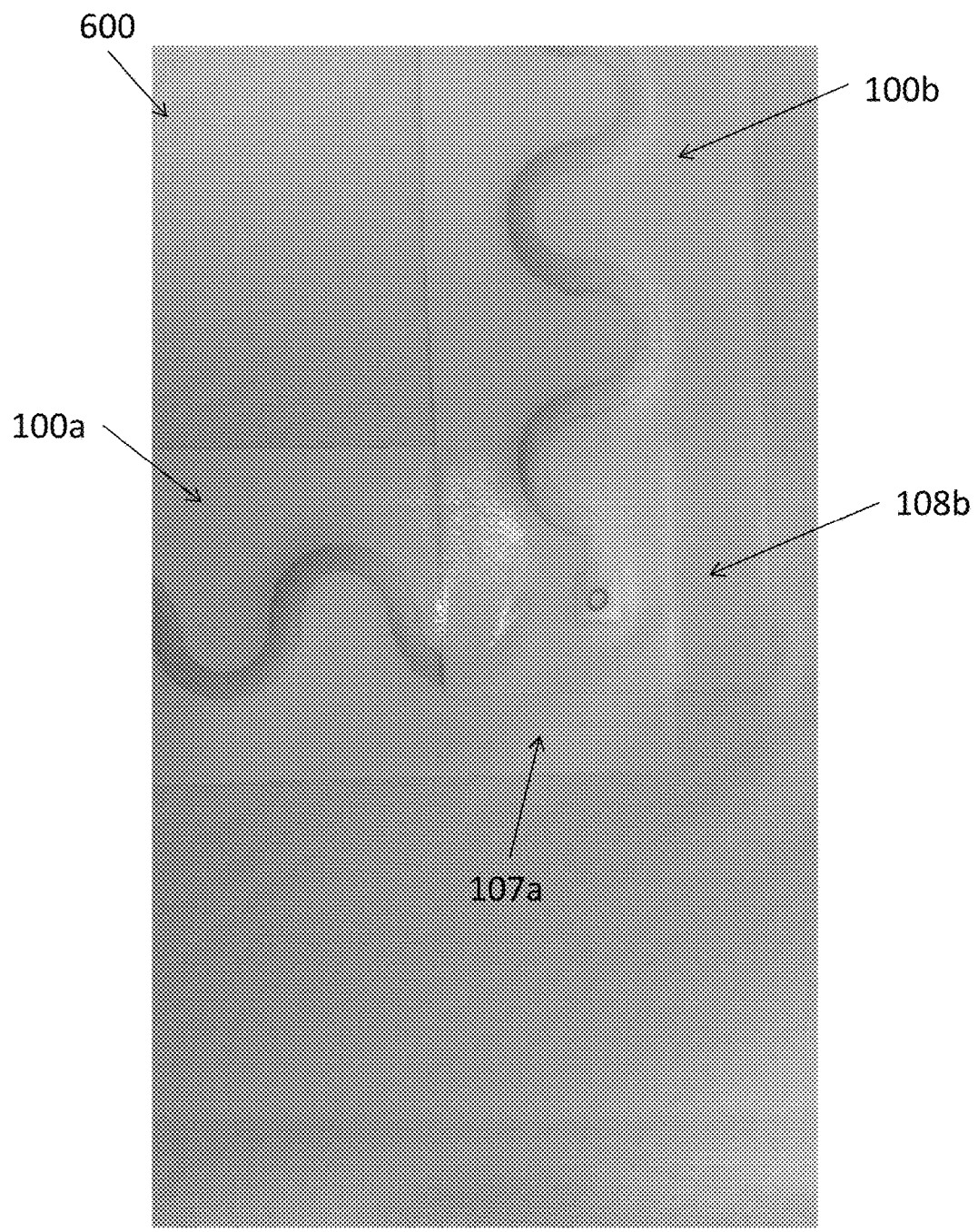
FIG. 7 shows an image of one embodiment of the system of FIG. 6.
Figure 8A:
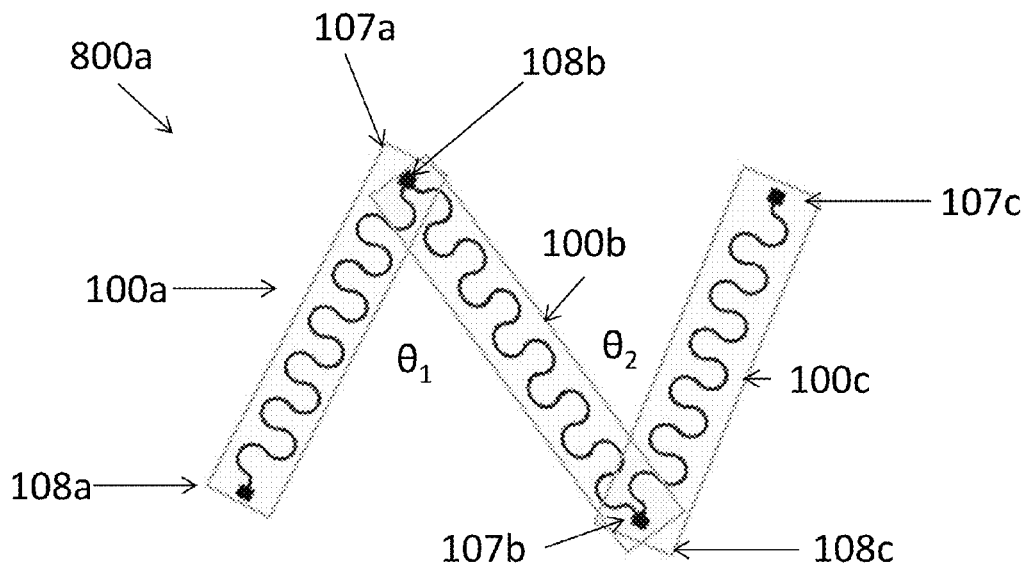
FIGS. 8A-8B show embodiments of a system that includes a flexible interconnect.
Figure 8B:
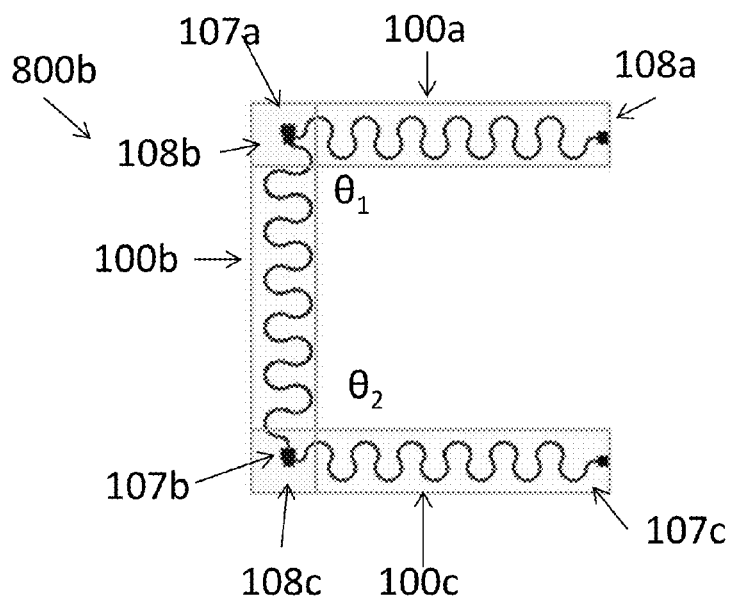

With embodiments of the flexible interconnect described in mind, attention is directed to FIG. 6, which one embodiment of a system 600 that includes a flexible interconnect. As shown in FIG. 6, the system 600 can include two flexible interconnects (100a, 100b) that are coupled to each other through an electrical via generated by physically contacting and/or physically integrating an exposed conductive pad at the "minus" end 108a of the first flexible interconnect 100a to the "plus" end 107b of the second flexible interconnect 100b. In this way, any number of flexible interconnects (100a, b, c . . . n) can be connected in the system. FIG. 7 shows an image of an embodiment of a system having two flexible interconnects. With this in mind, FIGS. 8A and 8B demonstrate systems 800a, b having 3 flexible interconnects. The flexible interconnects 100a, b, c . . . n can be connected at any angle θ from about 0° to about 108°. As shown in FIG. 8A, the flexible interconnects 100a, b, c are connected at angles ($\theta_1$, $\theta_2$) of less than about 90°. In FIG. 8B, the flexible interconnects 100a, b, c are connected at angles ($\theta_1$, $\theta_2$) of 90°.

Figure 9:
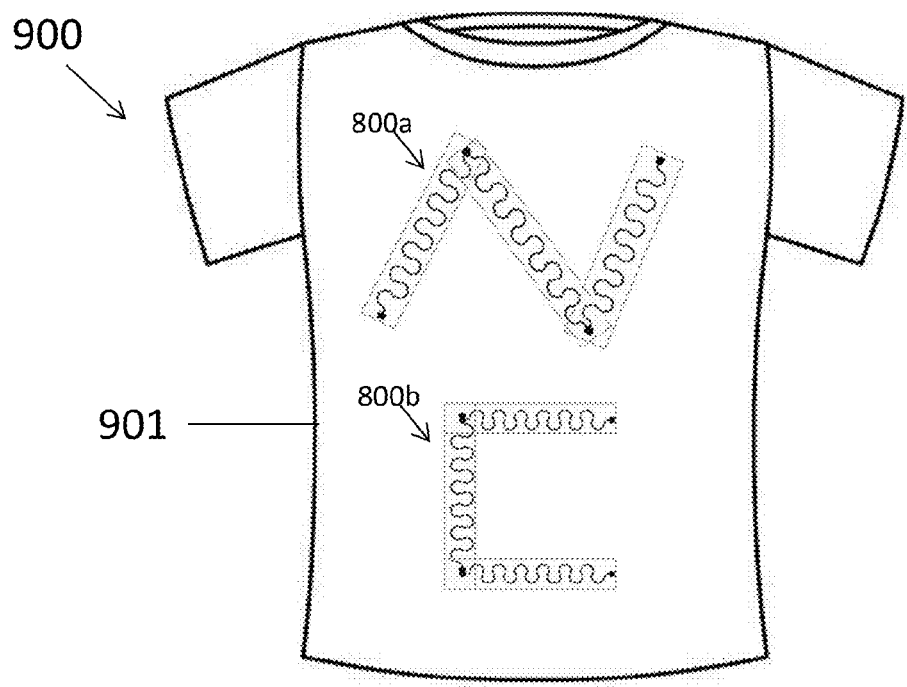
FIG. 9 shows one embodiment of a textile that includes a flexible interconnect.
Figure 10:
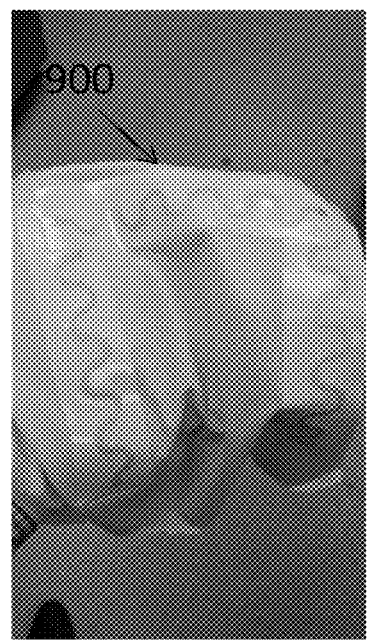
FIG. 10 shows an image of one embodiment of a textile that includes a flexible interconnect.

The system can include a textile. FIGS. 9-10 show embodiments of electronic textiles having a flexible interconnect or flexible interconnect system. As shown in FIG. 9, the flexible interconnects and flexible interconnect systems described herein can be coupled to, attached, or otherwise integrated with a textile 901 to create an electronic textile 900. The textile can be a woven textile (including knitted textiles) a non-woven textile, or a combination thereof. Woven and non-woven textiles are generally known in the art. Any textile can include any number of flexible interconnects and/or flexible interconnect systems described herein. The electronic textiles described herein can be configured into anything a textile can be used for, including but not limited to, garments (including protective clothing and suits), footwear, bags and other containers, towels and bedding, floor coverings, wall coverings, window coverings, upholstery and/or furniture, tents, flags, parachutes, boat sails, and airbags.

The flexible interconnects, flexible interconnect systems, and electronic textiles described herein can be made using manufacturing techniques generally known in the art. The electronic textiles described herein can be fabricated through a process that includes screen printing, di-cutting, and heat-transfer of the flexible interconnect to a textile. In some embodiments, printing of the conductive ink onto a thermoplastic polymer film can be performed by hand. In other embodiments, printing of the conductive ink onto a thermoplastic polymer film can be performed by lab scale and/or industrial scale screen-printing equipment. An adhesive stencil can be placed on screen-printing mesh and conductive ink can be transferred to the thermoplastic polymer film. Transfer can occur by hand or by machine. In some embodiments, a hand held squeegee operated at a 45° angle at an operator-controlled pressure can be used to transfer the conductive ink by hand. Any number of passes with the conductive ink can be conducted. In some embodiments 1-5 passes are conducted.

After printing, the printed thermoplastic polymer film can be cured. In some embodiments, the printed thermoplastic polymer film can be cured at about 60°. In some embodiments curing can take about 15 minutes. It will be appreciated that the exact time and temperature need for curing will depend on, inter alia, the composition of the conductive ink, the number of layers of conductive ink used, and the composition of the thermoplastic polymer film.

After curing, a second thermoplastic polymer film can be laminated on top of the cured and printed thermoplastic polymer film to generate a flexible interconnect. The flexible interconnect can be transferred onto a textile. In some embodiments, a heat pressing machine can be used to transfer the flexible interconnect.

In other embodiments, after curing the printed thermoplastic polymer film can be transferred onto a textile. In some embodiments, a heat pressing machine can be used to transfer the cured and printed thermoplastic polymer film to the textile. A second thermoplastic polymer film can be laminated on top of the cured and printed thermoplastic polymer film that is attached to textile.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Figure 11:
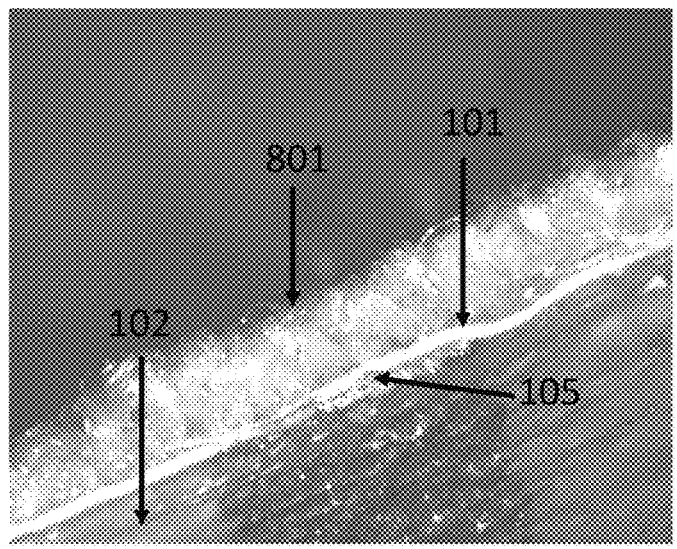
FIG. 11 shows a cross-sectional image of one embodiment of a textile that includes a flexible interconnect.
Figure 12:
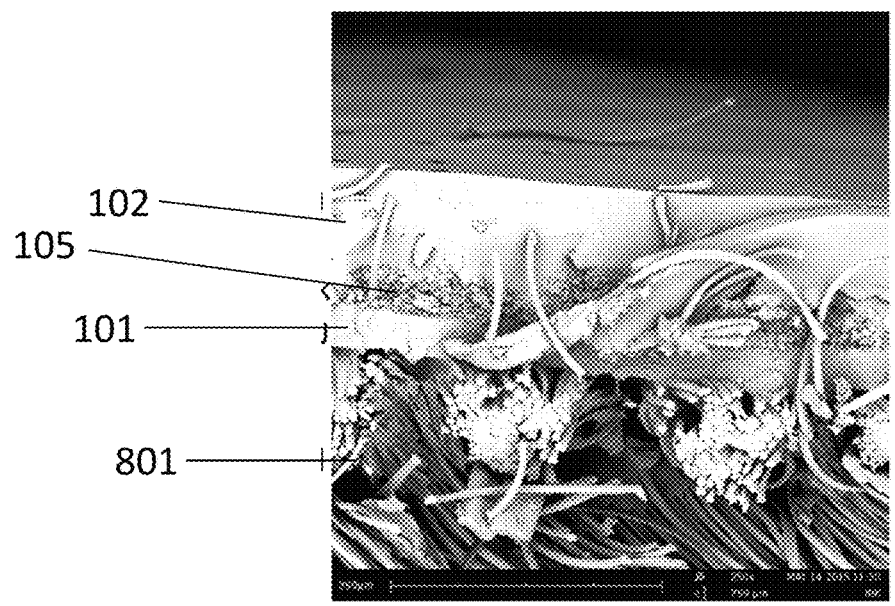
FIG. 12 shows a scanning electron microscope image demonstrating a cross-section of one embodiment of a textile that includes a flexible interconnect.

FIGS. 11-12 show cross sections of an electronic textile having a flexible interconnect as described herein. FIG. 11 shows an image of a cross section of an electronic textile having a flexible interconnect encapsulated in thermoplastic polyurethane (TPU). FIG. 12 shows a scanning electron microscope image of an electronic textile having a flexible interconnect encapsulated in thermoplastic polyurethane (TPU). As shown in FIGS. 11 and 12, the first TPU layer 101 is physically coupled to a knitted fabric 801 and the silver ink conductive trace 105 is encapsulated between the first TPU layer 101 and a second TPU layer.

Example 2

Figure 13:
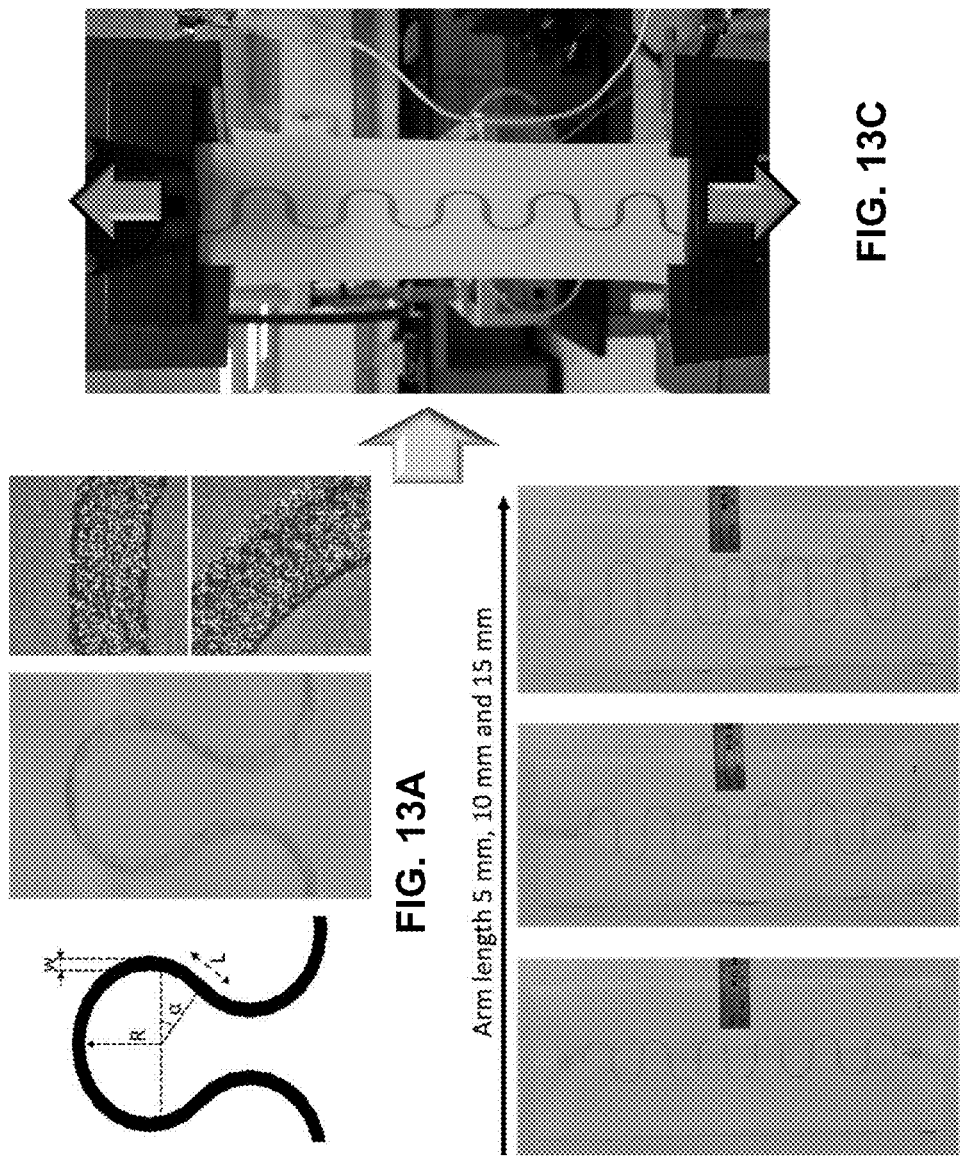
FIGS. 13A-13C shows several examples of the flexible interconnect described herein, demonstrating various dimensions of the conductive trace (FIG. 13A), various arm lengths of the conduction trace (FIG. 13B), and an image demonstrating a method for testing the flexible interconnects described herein (FIG. 13C).

FIGS. 13A-13C shows several examples of the flexible interconnect described herein, demonstrating various dimensions of the conductive trace (FIG. 13A), various arm lengths of the conduction trace (FIG. 13B), and an image demonstrating a method for testing the flexible interconnects described herein (FIG. 13C). As shown in FIG. 13(C), a strain or stress can be applied acutely or cyclically by pulling the ends of a flexible interconnect or electronic textile as described herein in opposite directions from one another. The durability of the flexible interconnect and textiles incorporating the flexible interconnects can be tested by measuring changes in resistance of the conductive trace after applying stress or strain. Other tests for durability include evaluating performance generally following the standard practice for the evaluation of machine washable t-shirts (ASTM D6321/D6321M-14).

Example 3

Figure 14:
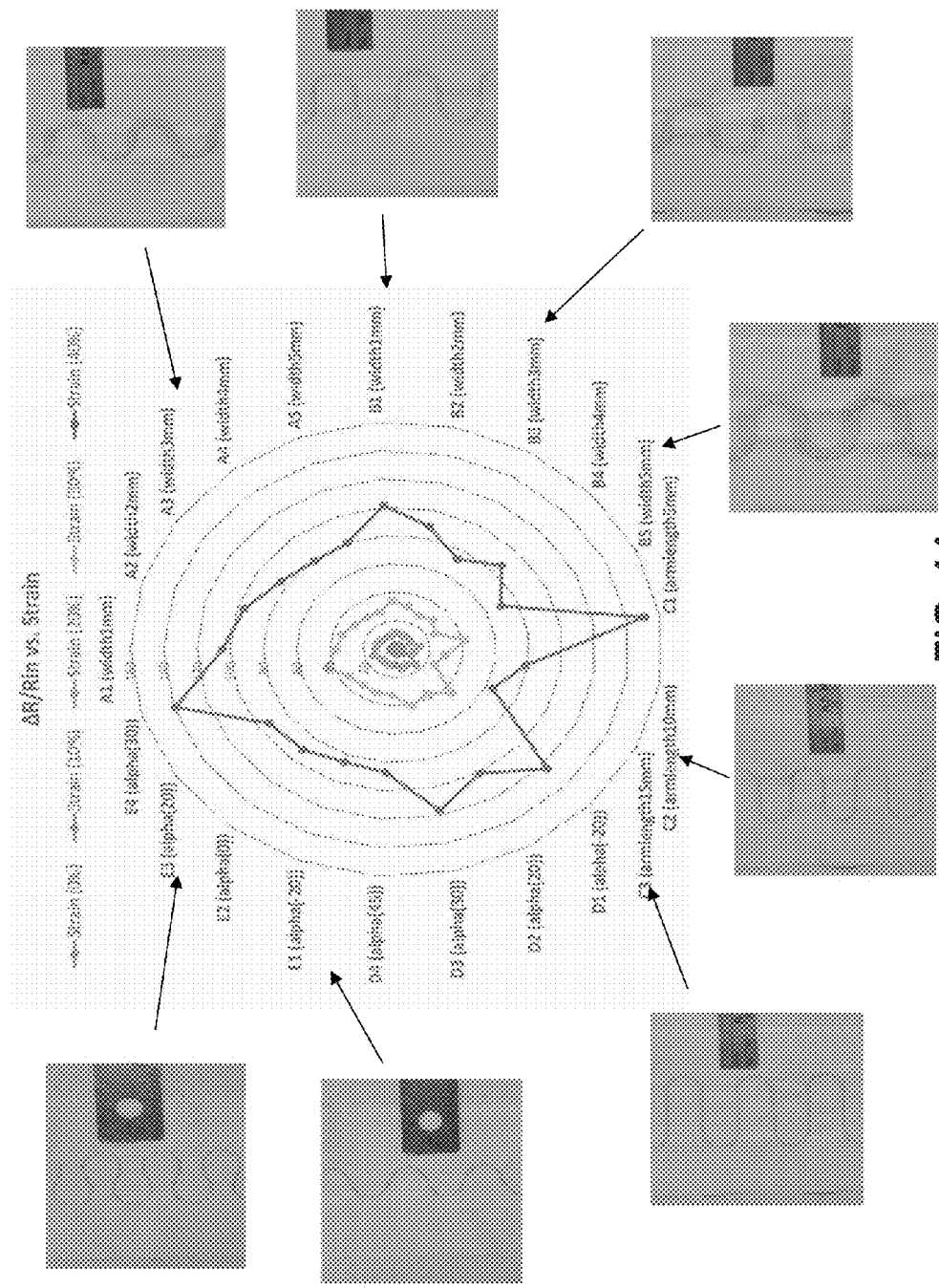
FIG. 14 demonstrates the effect of changing the dimension(s) of the conductive trace on the change in resistance ($\Delta R$) in the conductive trace.

As discussed above, the conductive trace can be configured in a variety of patterns and is only constrained by the design parameters previously discussed. Different combinations of design parameters can result in flexible interconnects and electronic textiles that can be suited for different purposes. FIG. 14 demonstrates the effect of altering different design parameters on the durability of textiles incorporating flexible interconnects described herein.

A modified standard stress-strain test was performed. The standard stress-strain test (generally following ASTM D5034-09(2013) was modified by having conductive wires extending from each end of the device for real-time resistance monitoring during testing.

Example 4

Figure 15:
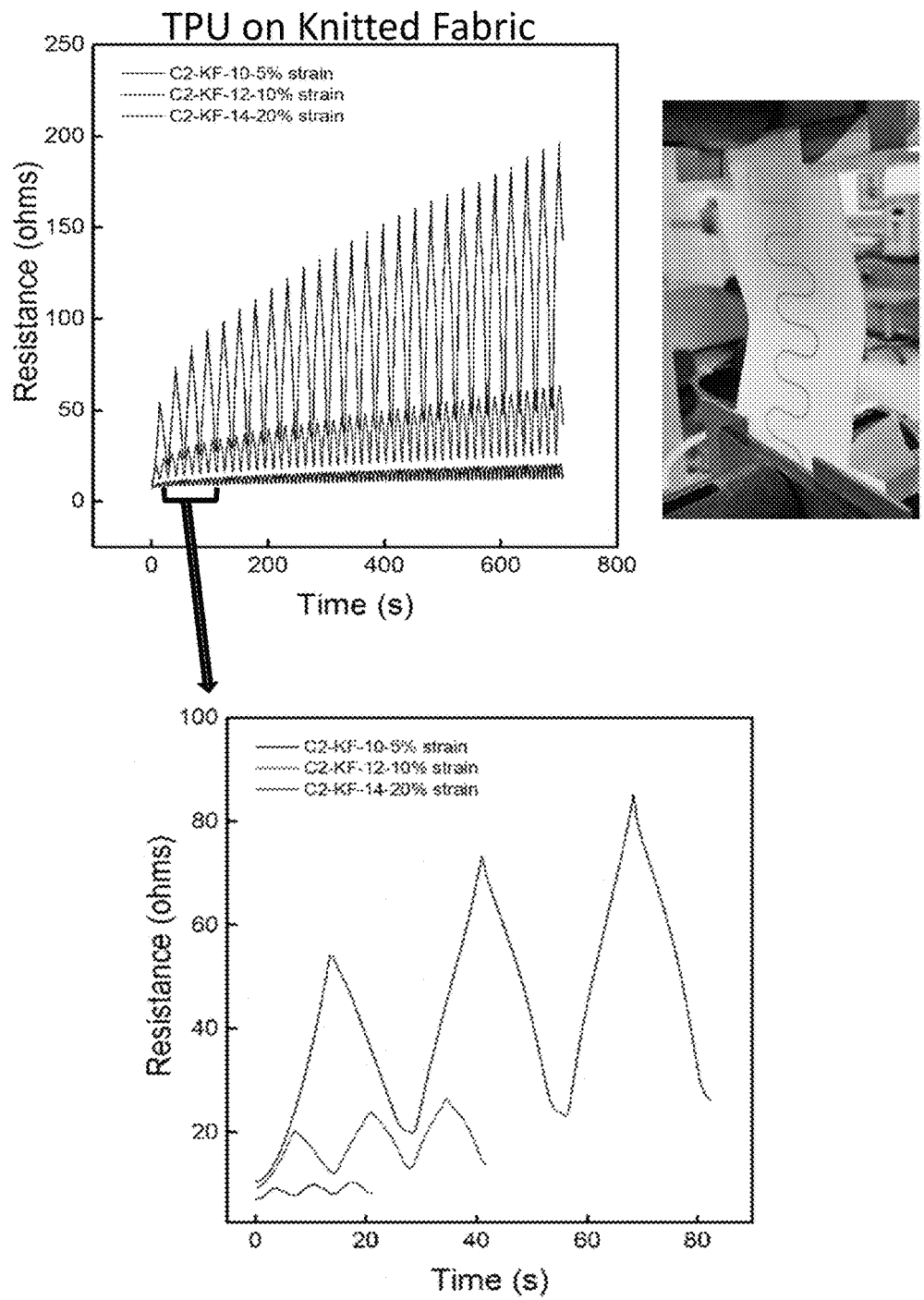
FIG. 15 shows graphs demonstrating the recovery of a flexible interconnect when incorporated in a knitted fabric (woven fabric).
Figure 16:
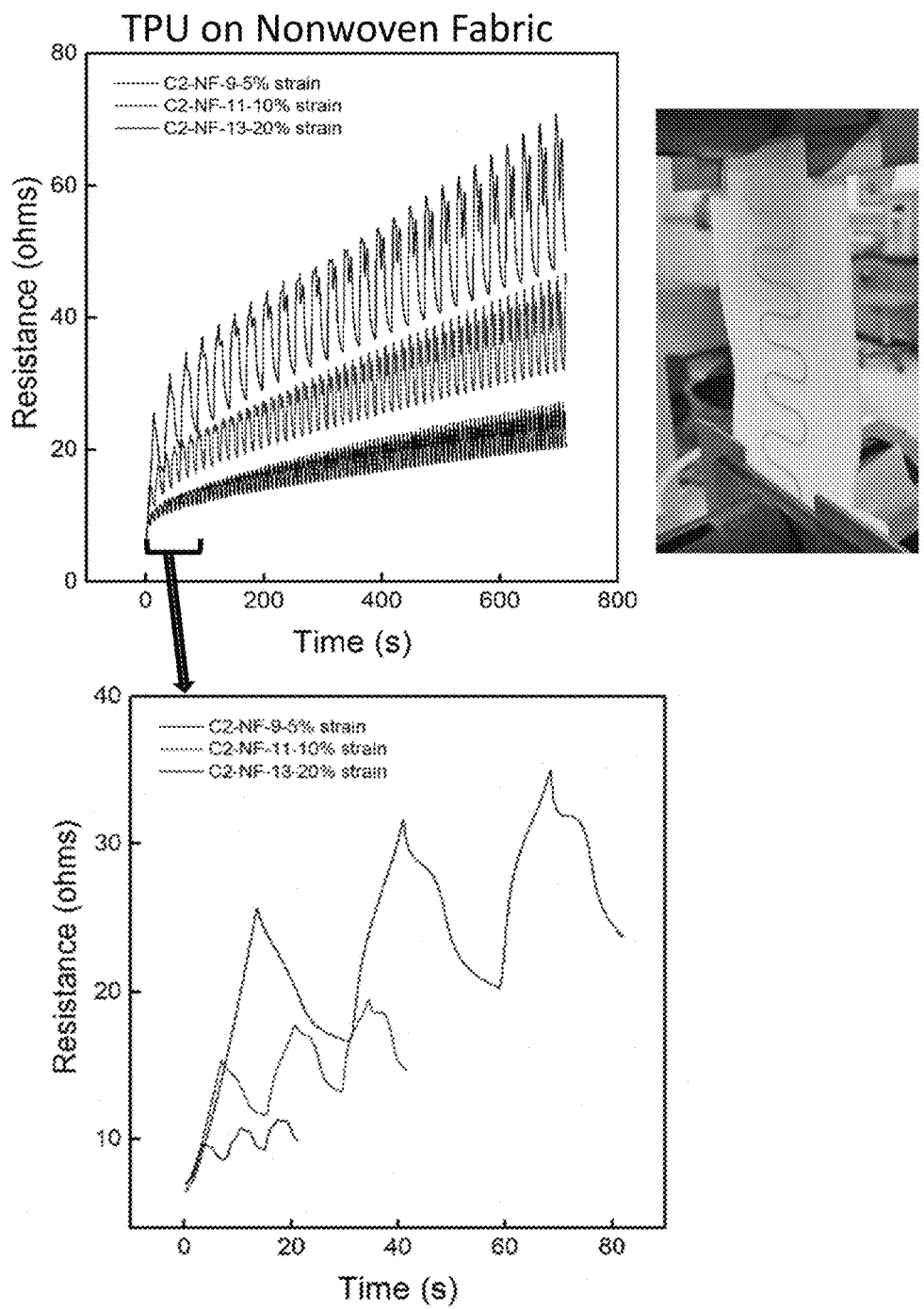
FIG. 16 shows graphs demonstrating the recovery of a flexible interconnect when incorporated into a non-woven fabric.

The type of textile that the flexible interconnect is incorporated with can affect the durability of the electronic textile. To determine the effect of the textile type on durability of the electronic textile, a flexible interconnect as described herein was coupled to either woven or non-woven textiles. Various strains were applied to the electronic textiles and resistance over time was measured. The results are demonstrated in FIGS. 15 and 16. A complete isotropic recovery was observed with knitted fabric at a 5% strain. The shoulder observed in the reverse cycle in the results shown in FIG. 16 from the electronic textile made with non-woven fabric indicated that a permanent deformation of the nonwoven fabric occurred.

Example 5

Figure 17:
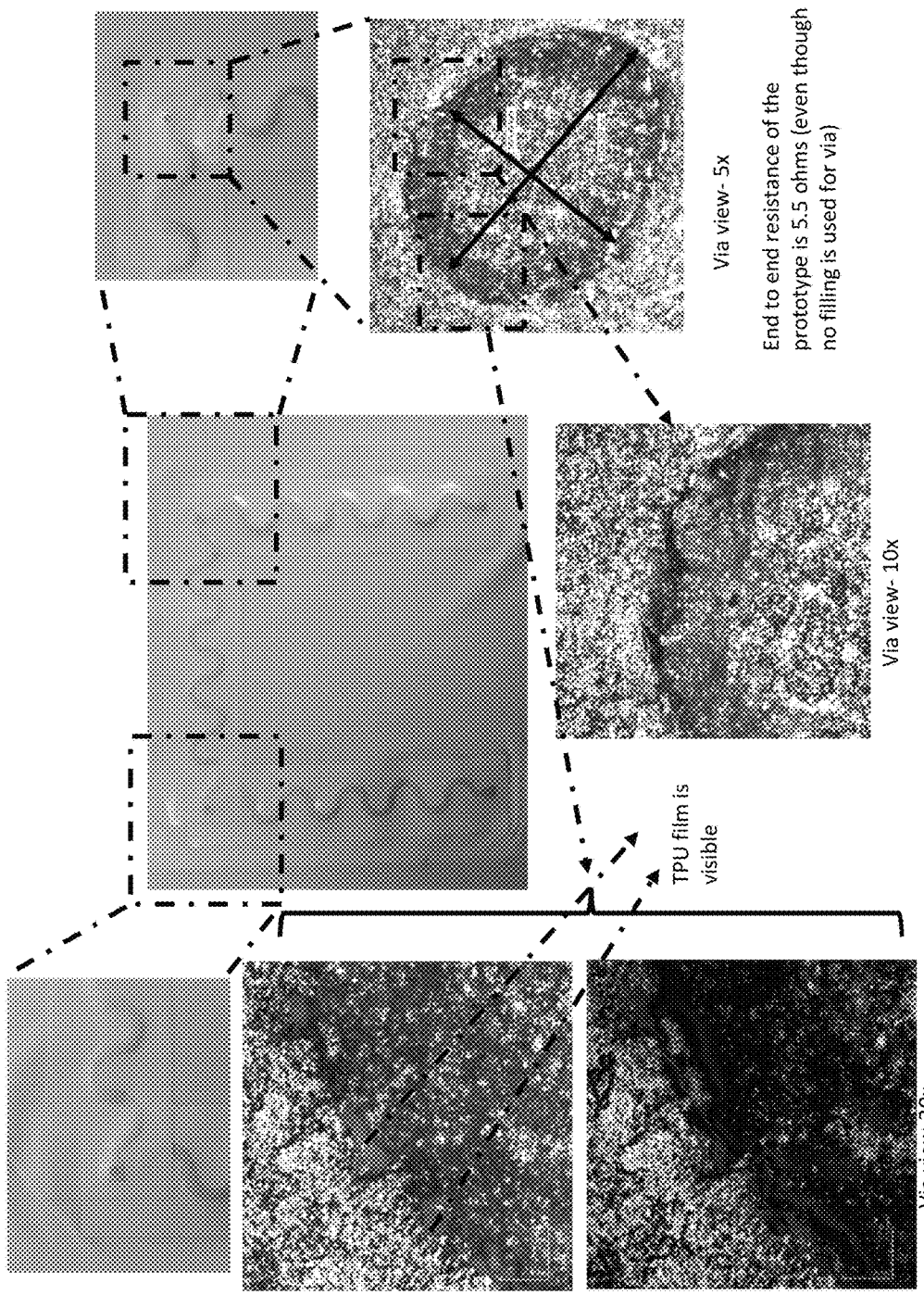
FIG. 17 shows images demonstrating the connection between two interconnects at a hole (via) in the thermoplastic polymer layers.

FIG. 17 shows several views and microscope images of an electronic textile according to the present disclosure.

Example 6

Figure 18:
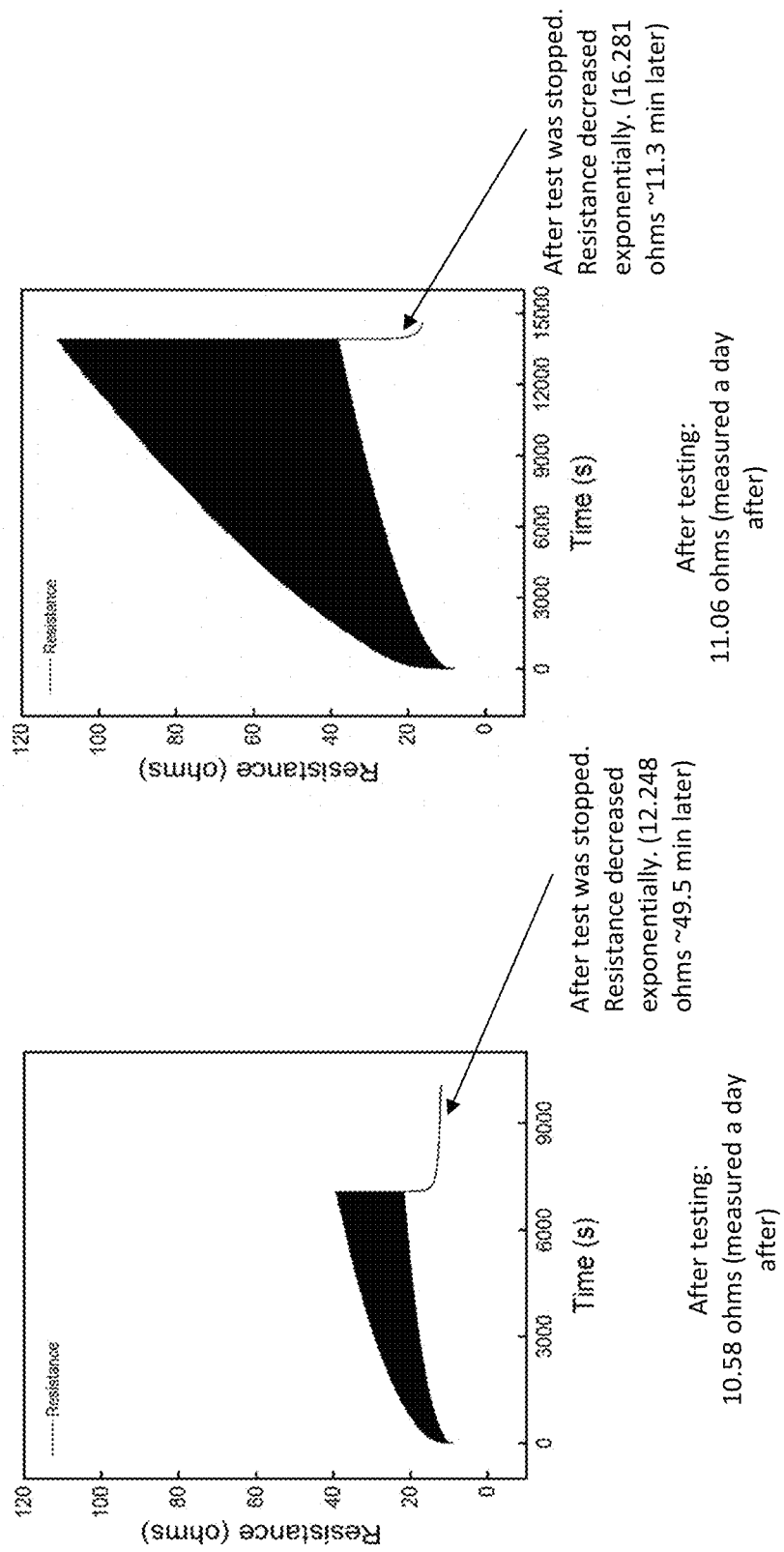
FIG. 18 shows graphs demonstrating the effect of strain on the resistance of the flexible interconnect over time.
Figure 19:
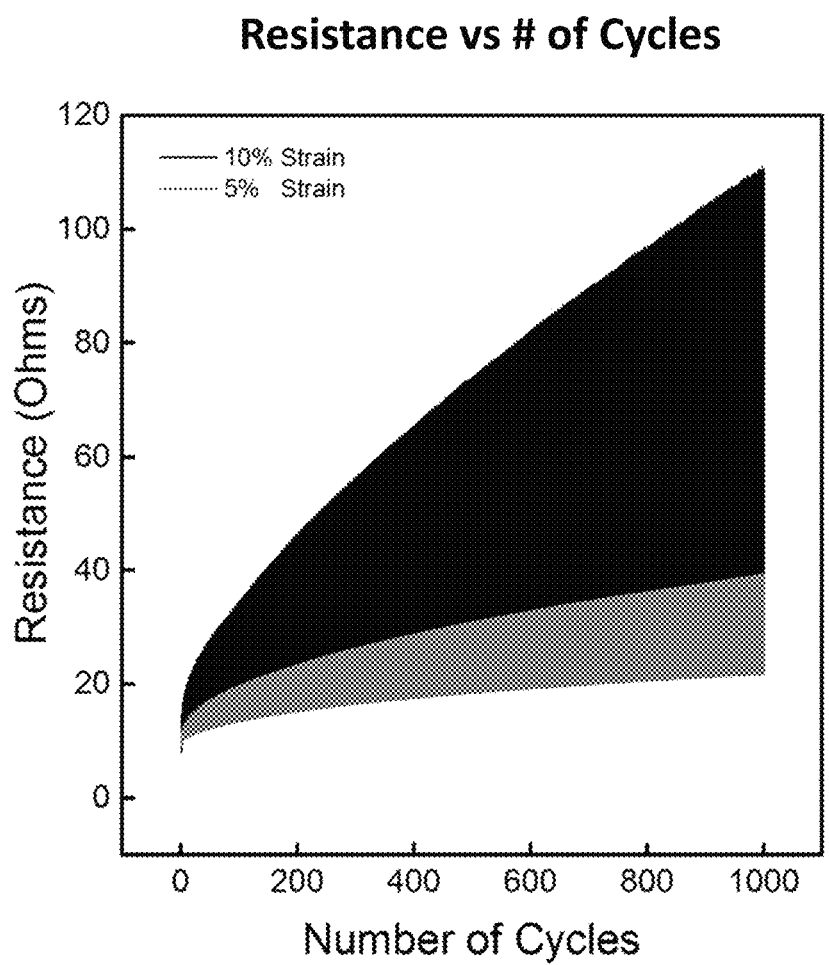
FIG. 19 shows graphs demonstrating the effect of strain on the resistance of the flexible interconnect over number of cycles of the oscillation test.

A prototype electronic textile was subjected to a 1000 cycle oscillation strain test. The test was performed at a 5% and a 10% strain. The results are shown in FIGS. 18 and 19. At 5% resistance, the measured resistance decreased exponentially to about 12.248 ohms at about 50 minutes after the test was stopped and was about 10.58 ohms 1 day after testing. At 10% strain the resistance decreased exponentially to about 16.281 ohms about 11.3 minutes after the test had stopped and was about 11.06 ohms when measured the following day. FIG. 19 demonstrates the resistance as per cycle number of the 1000 cycle oscillation test for both the 5% and the 10% strained conditions.

Example 7

Manufacture of an Electronic Textile Having a Flexible Interconnect

Ink and Substrate: Ag/AgCl ink (CM 124-36) from Creative Materials Inc. was used to create conductive traces on flexible thermoplastic polyurethane (TPU) films. The conductive ink was observed to have excellent adhesion to a variety of substrates, and it has been observed to be resistant to flexing and creasing. The TPU film (TL 644) was obtained from Bemis Inc., which has high modulus and good recovery that can work well for performance wear and compression wear applications. The TPU film has a matte finish on one side that can be activated at low temperatures. This film has excellent adhesion to various substrates (Nylon/Spandex, Polyester/Spandex and Cotton/Spandex blends). TL644 film is compatible with screen-printing process and resistant to high washing temperatures (up to about 60° C.).

Procedure: The printing of conductive ink onto TPU film was performed by hand operated lab scale screen-printing equipment. A CAD designed meandering shape was transferred to an adhesive stencil by Silhoutte Cameo die cutter for rapid prototyping. The adhesive stencil was placed on 100 size screen-printing mesh and the conductive ink was transferred onto the TPU film by hand held squeegee with 45° angle at an operator-controlled pressure. Two passes of ink were performed. The printed film was then cured at 60° C. for 15 min. Afterwards, the printed film was transferred onto a knitted fabric (87/13 Polyester/Spandex) via a heat pressing equipment. The heat press equipment's temperature was set to 125° C., and minimum pressure for 30 seconds was used to combine the printed TPU film with the knitted fabric. To be able to protect the printed lines from wear and rubbing, a similar high recovery transparent TPU film (TL 3916) was utilized. It was laminated on top of the printed lines with similar heat press conditions (125° C. for 30 sec.). Upon completion of each of the previous steps, a sandwiched structure was created (e.g. two or more TPU films enclose the conductive printed traces from top and bottom, and the three layers (TPU-ink-TPU) are bonded onto a knitted fabric). Ultimate multi-layer design was observed to be stretchable, bendable and washable. It was observed to maintain its electrical properties under certain washing and stretching cycles.

Example 8

Wearable electronics have been the focus of attention for researchers in the last couple decades. There is a significant growing interest in this field ranging from unobtrusive textile integrated bio-sensors [1], to electrochromic displays embedded into textiles [2]. Current research focuses on the use of nanotechnology, organic materials, and innovative fabrication techniques to create flexible electronic devices such as sensors [3], supercapacitors [4], conductive yarns [5], and energy harvesting devices [6]. These flexible devices are designed to bend and flex to form on curvilinear surfaces, which make them suitable for integration into textiles. The unobtrusive integration of discrete flexible devices into textiles creates a new norm for wearable technology, i.e., a smart garment.

There are several characteristics to be considered when creating a wearable smart garment, including air and vapor permeability biocompatibility, comfort, washing and chemical (e.g., detergent) resistance, and ease of deformation (bending, compression, extension etc.). Electro-mechanical durability of the smart garment when subjected to large strains is also important to consider in determining the endurance of the garment to the dynamic forces of body movement. Prior research has shown that fabrics may experience up to ~20% strain during a set of various physical activities [7], [8]. Electronics positioned various locations of the fabric will undergo this range of deformation from the body's movement. Ideally, this deformation needs to happen through stretchable interconnects between the less resilient, hard electronic components. Therefore, the design of stretchable interconnects is important for maximizing the functionality while at the same time accommodating larger strains without constraining body movement for human comfort.

In order to provide stretchability without diminishing the functionality of electronic devices, various fabrication methods and stretchable material structures have been studied. Fabrication of wavy or buckled single crystal semiconductor nanoribbons [9] or metals [10] (e.g., gold) by pre-straining the elastomeric substrate, and mesh-shaped structures [11] yielded electronic component (e.g., thin film transistors and transistor-based pressure sensors) functionalities up to 25% strain values by undergoing out-of-plane deformation. These techniques have yielded hemispherical electronic eye cameras based on an array of silicon photodetectors [12]. However, the methods require complex component transferring and mechanical pre-straining the polymeric substrate. A different approach to make stretchable interconnects is to fabricate planar horseshoe shaped structures by lithographically patterning gold on elastomeric substrates [13]. Failure strain of 54% and cyclic endurance of 200 cycles at 25% strain have been achieved. Moreover, a photoablation method [14] was utilized to fabricate rectilinear and meandering interconnect designs. Its fabrication process used metal layers for polymer masking; therefore, eliminating the alignment process and use of chemicals for etching. However, the presence of conical defects was stated to have an effect on the stretchability of the meandering lines. A failure strain of 50% with a resistance change ($\Delta R/R$) of 5% was shown. As an alternative method for stretchable interconnects, liquid alloy filled elastomeric micro-channels were studied [15]. This technique did not result in a crack formation, which is commonly encountered in metals upon elongation above 1%, due to the presence of alloy metal in liquid form at room temperature. Resistance change ($\Delta R$) of $0.24\Omega$ with 100% strain was indicated, but lower stretchability (~30%) was observed when active circuit elements were integrated into liquid metal filled micro-channels. Furthermore, an in-plane metal conductor technology for horseshoe shaped meandering lines was proposed by [16] to pattern copper with a polyimide support underneath. The polyimide support layer increased the fatigue life (3,400 cycles at 10% strain) of the meandering line. The fatigue life was further increased to 40,000 cycles at 30% strain by the addition of a supporting polyimide layer on top of the copper layer [17].

More recently, notable research has been done in nanomaterial research and development to fabricate stretchable interconnects. Carbon nanotubes (CNTs) and carbon black (CB) filled elastomers were developed toward the fabrication of strain gauges [18]. It was shown that CB filled elastomers had $\Delta R/R$ of ~140% at 5% strain because of separation of carbon particles with applied strain, which produced breakage of the conductive pathways. Likewise, serpentine shaped CNT filled elastomers had a $\Delta R/R$ of ~5% at 15% strain due to rotation and slide of CNTs against each other upon applied strain. In another study [19], silver nanowires (AgNWs) and silver nanoparticles (AgNPs) embedded in an elastomeric matrix had $\Delta R/R$ of ~2 after 1,000 cycles with 10% strain, which was attributed to AgNW breakage with high number of cycles. Even though some of the aforementioned methods and novel materials show excellent stretchability and endurance results, their manufacturing complexity, material cost, and scalability limit their usage in mass production of wearable electronics. For example, the current market price of CNTs and AgNWs is relatively expensive than conductive inks, which limits their usage to only nano-based applications rather than large-scale fabrications.

Other large-scale mass-production techniques such as knitting [20] and weaving [8] have been used in integration of electronic functionality into smart garments. Knitting polyurethane covered copper fibers with conventional yarns yielded 1% resistance change up to 300% strain values [21]. Screen-printing of the conductive inks, on the other hand, is an alternative industry scalable technique for fabrication of inexpensive electronic components action and removal steps as commonly found in semiconductor fabrication processes. Printing of various silver inks has been investigated on polyarylate films [22], woven and knitted fabrics [23], and nonwoven fabrics [24]. However, the electromechanical properties of the printed lines as a function of stretching were not investigated. On the other hand, a brush painting of poly(3,4-ethylenedioxythiophene):poly(styrene sulfonate) (PEDOT:PSS) conducting polymer on knitted fabrics was studied [25], reporting an elastic stretchability up to 30%. The resistance change after 1000 stretching cycles with 20% strain was about 10%. Screen-printing of horseshoe shaped silver ink on TPU films was studied in [26], and 7% stretchability value was reported. Finally, another study [27] showed development and printing of a new ink material with stretchability of >93% and endurance of 1,000 cycles at 30% strain. However, the design and optimization of the printed conductive meandering lines on films, its subsequent integration onto textile wearables, and the effect of stretching on the electrical properties of the printed lines were not studied thoroughly before. Addressing these matters will shed light on some of the challenges (e.g. interconnect reliability under large strains, electronics integration, and washability) in textile-based electronics.

Figure 20:
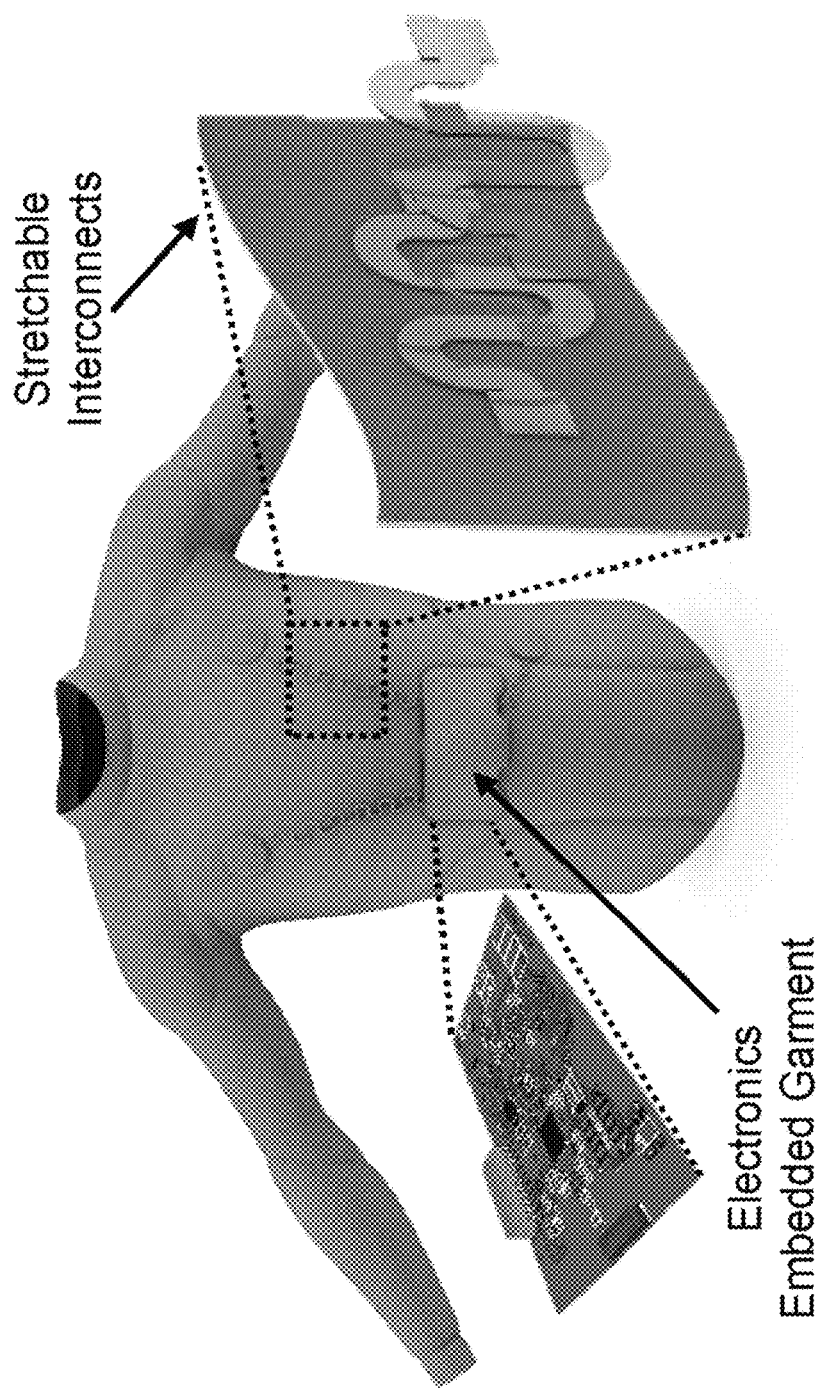
FIG. 20 shows an embodiment of a stretchable printed interconnect embedded smart garment that can incorporate low power electronics, sensors, and energy harvesting devices.

In this Example, printed meandering interconnects were fabricated on knit fabrics. Inexpensive and scalable screen printing techniques were utilized to print Ag/AgCl conductive ink on thermoplastic polyurethane (TPU) film. Its heat lamination onto knit fabric and subsequent protective encapsulation layer yielded stretchable interconnects, shown FIG. 20. The printed stretchable interconnects are used in integration of low power sensors and energy harvesting devices developed by a National Science Foundation Nanosystems Engineering Research Center on Advanced Self-Powered Systems of Integrated Sensors and Technologies (ASSIST). This article focuses on the design and optimization of printed conductive meandering lines, as well as the effect of the processing steps on the electrical properties of the printed lines. Two demonstrations are provided to exemplify the use of the technique developed in this manuscript. First, a surface mount LED integration onto printed meandering lines as a means of evaluating the application of multi-electrode devices. Second, a shirt is modified with the meandering lines to support a full-signal electrocardiography measurement.

Stretchable Interconnects Fabrication

A. Screen Printing Of Stretchable Interconnects. Stretchable interconnects were printed on both knit fabric and thermoplastic polyurethane film (TPU). The knit fabric, acquired from Hanes Brands Inc., NC, USA, is made of 87% polyester and 13% spandex yarns with a basis weight of 150 g/m$^2$. Inclusion of Spandex yarn within fabric construction yields high flexibility and recovery properties to the garment, which are important properties for intimate contact between the fabric and the diverse contours of the human body's surface. The TPU film (TL644), obtained from Bemis Inc., MA, USA, is composed of two layers: a polymer film layer and an adhesive barrier layer. Because of the adhesive layer's low softening point (~80° C.), the TPU film is suitable for heat sensitive fabrics during heat lamination. The film's ink receptive surface is suitable for screen-printing processes. It also has high washing resistance up to 60° C. Creative Materials Ag/AgCl electrically conductive ink (product number: 124-36) was used for printing of stretchable interconnects on the TPU film and the knit fabric. The conductive ink shows excellent adhesion to a variety of substrates and has sufficient resistance to flexing and creasing.

The conductive ink printing was performed by using hand operated lab scale screen-printing equipment. A CAD drawn interconnect design was patterned onto a vinyl stencil by using a Silhouette cameo die cutter. The adhesive stencil was then placed onto a 100-mesh size screen-printing frame, and the ink was transferred onto the substrates by a hand-held squeegee at a 45° angle with operator controlled pressure.

B. Multi-Layer Stretchable Interconnects.

The presented multilayer stretchable interconnect structure is given in FIG. 21A-21D. The layered structure is composed of four layers. The knit fabric (thickness: 0.46 mm) lies at the bottom, representing the garment. The TPU film (TL644, thickness: 0.1 mm), the meandering shaped conductive ink layer, and the TPU encapsulation (TL3916, Bemis Inc., thickness: 0.15 mm) are situated on top of the knitted fabric, respectively. The TPU film (TL644) and the TPU encapsulation film (TL3916) will be referred as printing layer and encapsulation layer, respectively, for the rest of the study. FIG. 21A shows the layered structure where the dimensions of the knitted fabric, the printing layer, and the encapsulation layer are similar (6 cm×16 cm). Whereas, in FIG. 21B the printing layer and encapsulation layer are cut to a meandering shape and then laminated on top of similar size knit fabric. FIGS. 21C and 21D display the top view of the layered structure. The width of printed ink and the encapsulation layer are shown as $w_{ink}$ and $w_{tpu}$, respectively. The printing layer and the encapsulation layer widths are the same, defined by an offset from the edge of the ink width, $w_{offset}=(w_{tpu}-w_{ink})/2$. The stretchable interconnect fabrication steps in FIG. 21A are given below.

1) Cut a 6 cm×16 cm knitted fabric in warp direction.
2) Cut a 6 cm×16 cm TPU film (TL644) for printing layer.
3) Screen-print conductive ink on the printing side (non-adhesive side) of the printing layer (2 passes of conductive ink) and cure at 60° C. for 15 min.
4) Laminate conductive ink printed layer onto knitted fabric with a heat press at 125° C. for 2 min.
5) Laminate the encapsulation layer on top of the printed line at 125° C. for 2 min.

Figure 22A:
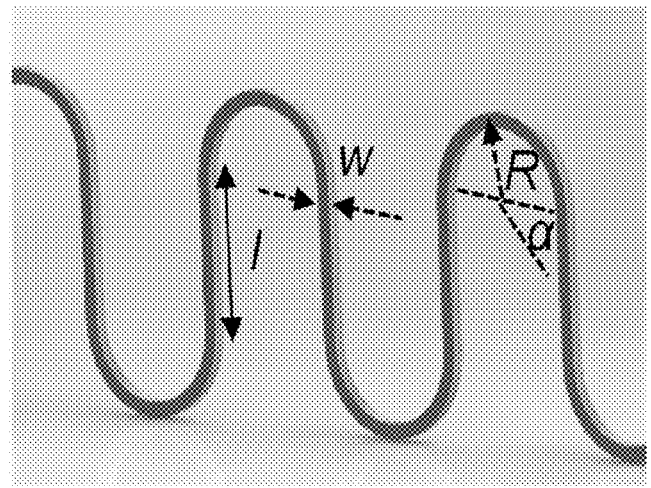

The multilayer interconnect structure in FIG. 21B was also fabricated by cutting of the printing and encapsulation layers with $w_{offset}$ values of 2 mm and 4 mm. The rest of the procedure is similar as given for FIG. 21A Results and Discussion A. Screen-Printing of Conductive Ink on Knitted Fabric and TPU Film Meandering and straight lines were initially printed on both the knit fabric and the TPU film individually without any lamination and encapsulation steps. The design of the meandering line is given in FIG. 22A. The design was determined by the parameters: width (w), arm length (l), radius (R), and angle (α). A straight line with a 3 mm width and 14 cm length, and a meandering line (w=3 mm, l=0 mm, R=5 mm, α=0° and total length=13.4 cm) were printed on both substrates.

Figure 22B:
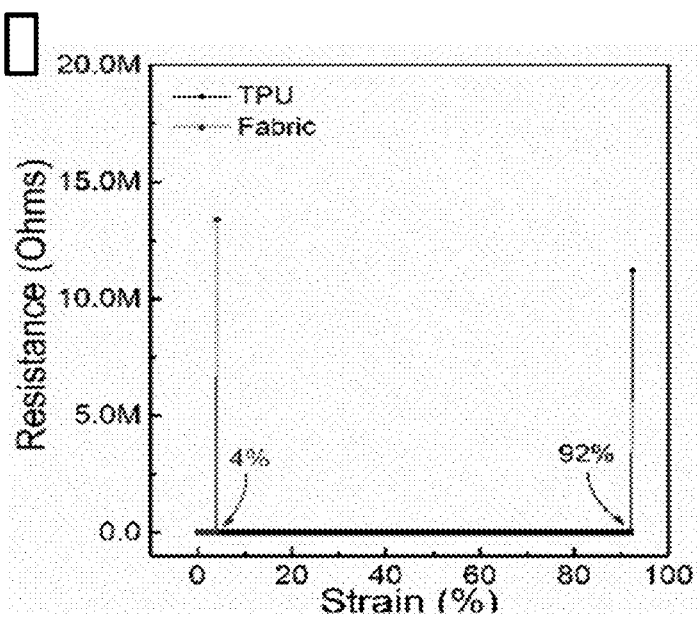
Figure 22C:
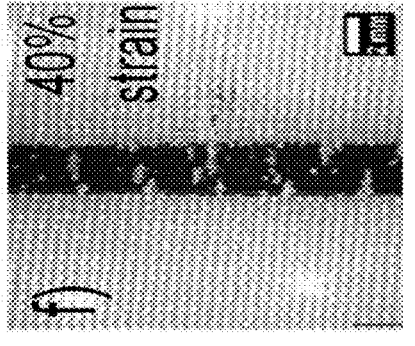
Figure 22D:
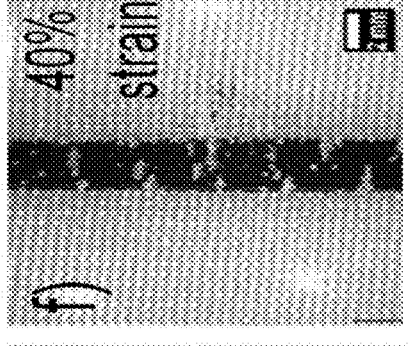
Figure 22E:
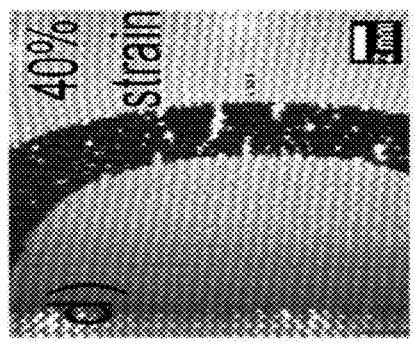
Figure 22G:
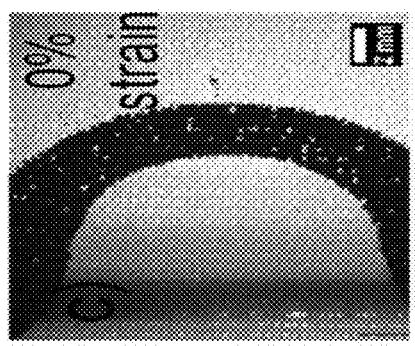
Figure 22H:
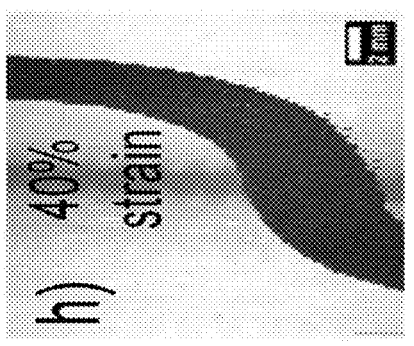
Figure 22I:
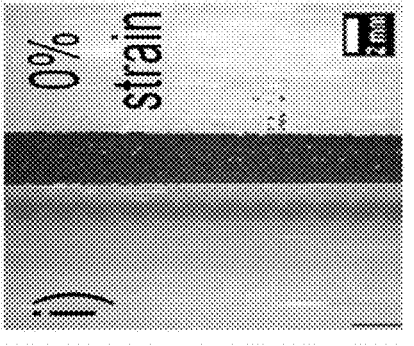
Figure 22J:
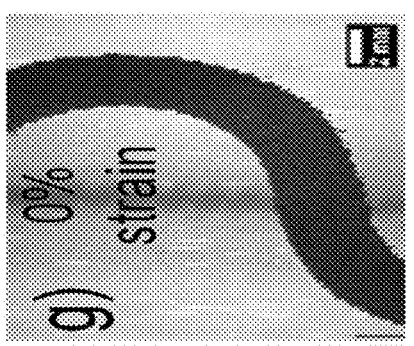
Figure 23A:
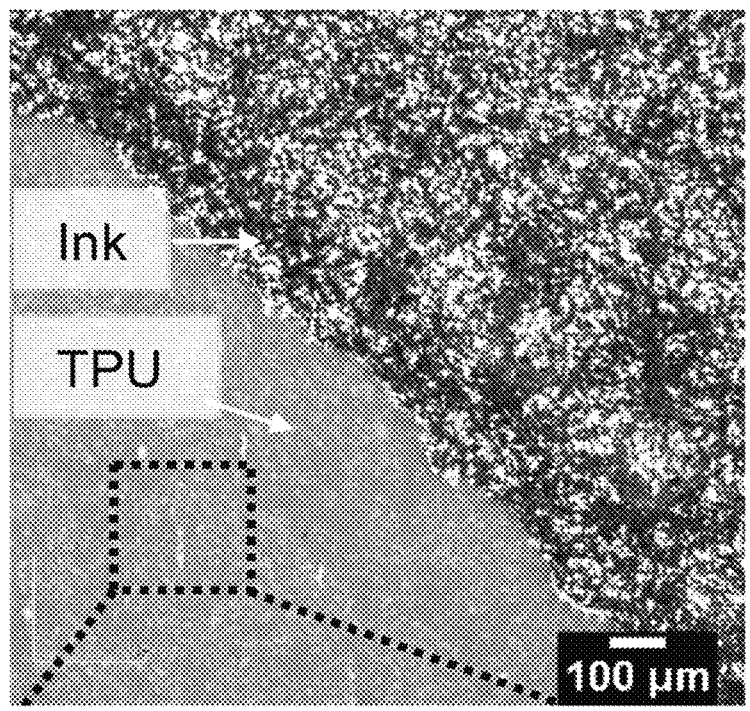
FIGS. 23A-23D show (FIG. 23A) Optical microscopy picture of the ink on TPU film, (FIG. 23B) SEM cross-sectional picture of the printed conductive ink on TPU film, (FIG. 23C) SEM surface picture of the TPU film, (FIG. 23D) AFM surface topology of the TPU printing layer.
Figure 23B:
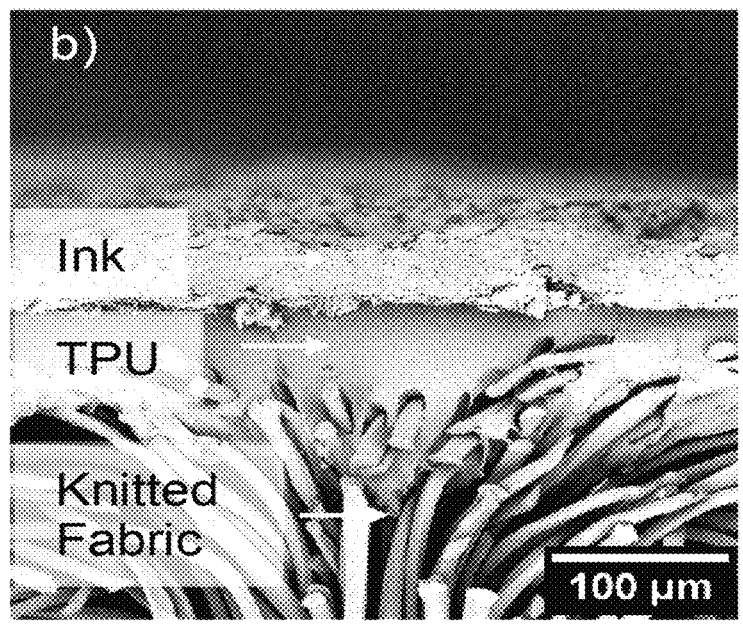
Figure 23C:
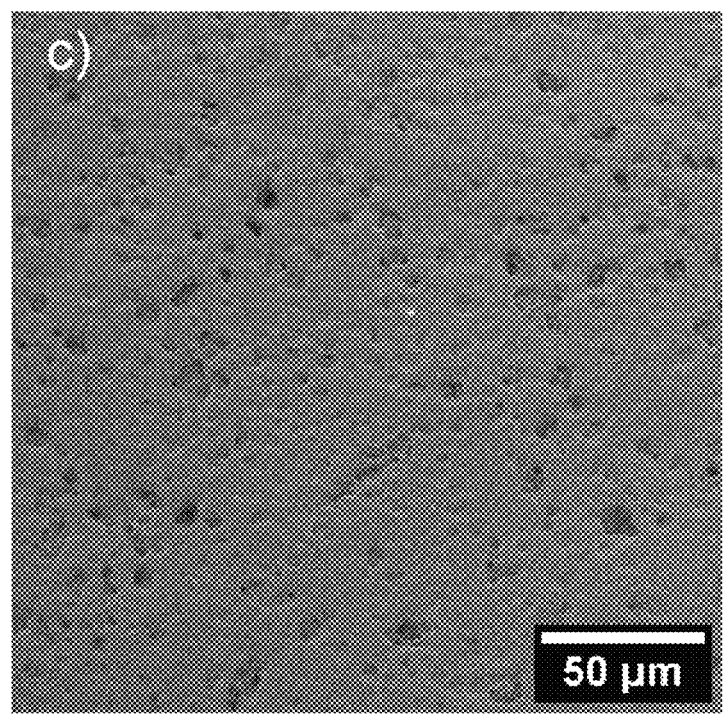
Figure 23D:
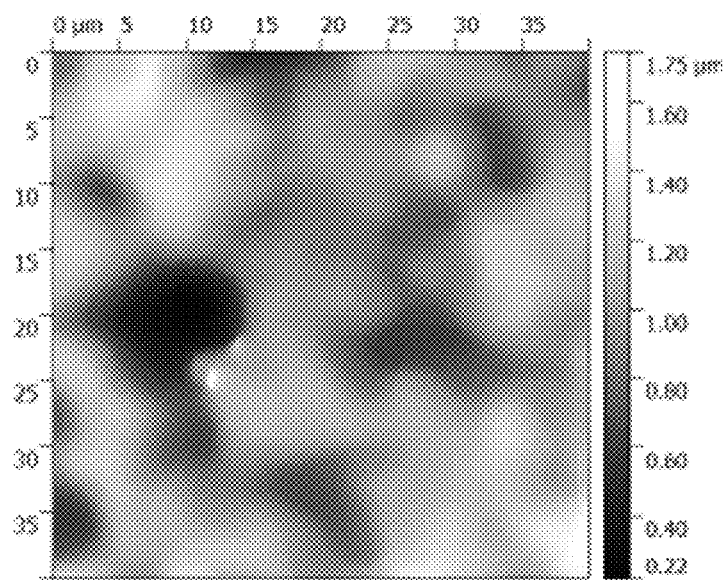

Their surface topology and electromechanical properties were compared. The surface properties of the printed ink were analyzed by Scanning Electron Microscopy (SEM), Optical Microscopy, and Digital Microscope and Atomic Force Microscope (AFM). The in-situ electromechanical properties of the printed lines were measured with a MTS tensile tester (gauge length: 11.5 cm, crosshead speed: 5 cm/min). Two-probe electrical resistance was simultaneously recorded (2 Hz) with LabVIEW software. FIG. 22B shows the resistance change of the printed straight traces on the knit fabric and the TPU film as the samples were elongated. The printed straight lines failed (open electrical resistance) at 2.16%±2.60% strain on the knit fabric. However, the same printed line on the TPU film could withstand up to 98.60%±9.02% strain. On the other hand, the meandering lines on the knit fabric and the TPU film were able to be stretched up to 34.85%±0.64% and 112.84%±23.67% strains, respectively, without electrical failure. The digital microscopy pictures of the printed meandering and straight lines on the knitted fabric and the TPU film are given in FIG. 22C-22F and FIG. 22G-22J. The pictures were taken with a digital microscope situated over a custom-built stretching device strained the sample in discrete strain intervals. The printed straight and meandering lines on the knit fabric showed significant crack formation at 40% strain, relative to that on the TPU film. This result can be attributed to the high surface roughness and surface area of the knit fabric compared to the TPU film. Two passes of conductive ink printing on the knitted fabric created less surface coating due to its high fibrous surface area. Uncoated areas were still visible on the surface of the knitted fabric after the screen-printing process in FIGS. 22C and 22E. The printed ink penetrates through the structure of the yarn. It also fills the large gaps that are created by the inter-looped formation during knitting process. Therefore, the same amount of ink on the knitted fabric yielded less continuous conductive tracks, which made it sensitive to stretching at low strain values. The conductive ink printing on the TPU film yielded had a thickness of 20 micrometers, as shown in FIG. 23B. Inspection did show localized sections of the meandering line to be as high as 50 micrometers. The variability in the thickness of the ink is much lower as compared to ink printed on fabrics. This was due to the TPU film's relatively smooth surface (FIGS. 23A and 23C) compared to the knitted fabric surface. This was shown with an AFM surface topology picture (FIG. 23D). The TPU film had a roughness value of 0.185 micrometers, which yielded a continuous formation of conductive tracks on TPU surface. Thus, the straight and meandering lines on TPU film at 40% strain had less visible holes and crack formation relative to that on the knit fabric. Due to strain relief property of the meandering line, the maximum stretchability of the meandering line on both substrates was higher than that of the straight line.

Figure 24A:
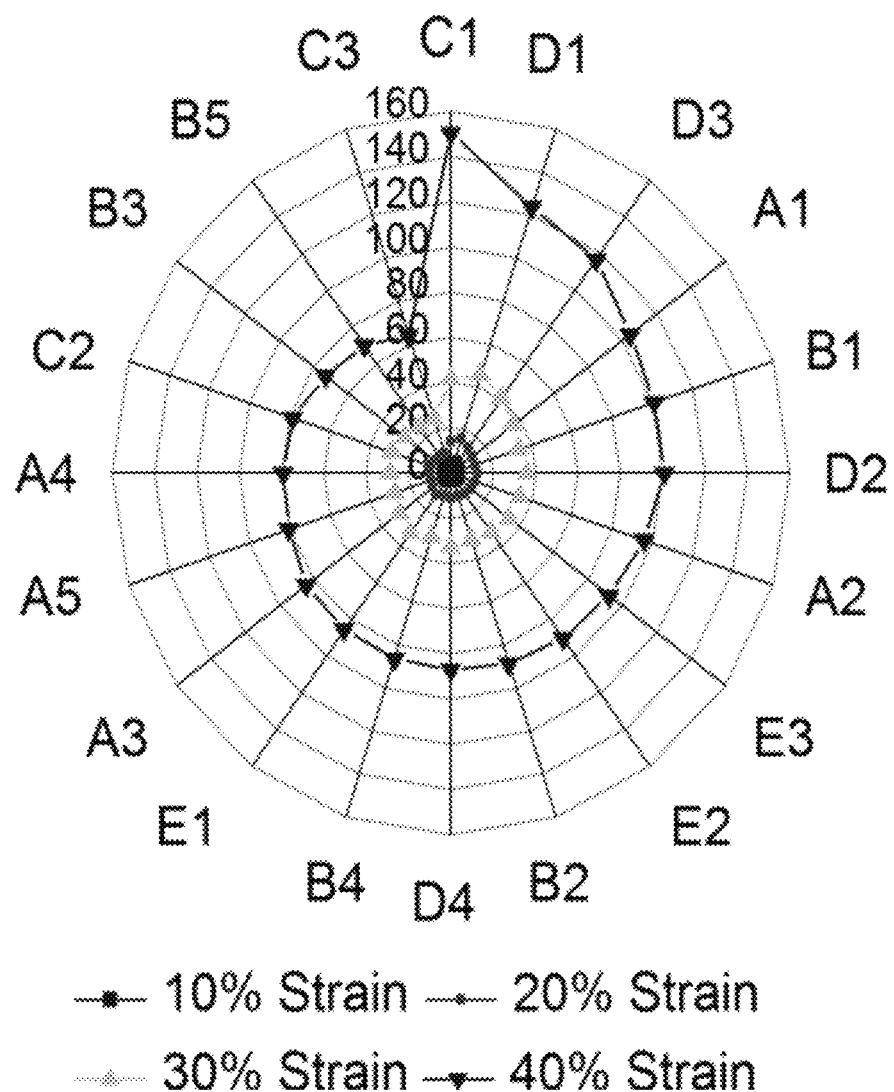
FIGS. 24A-24C show (FIG. 24A) $\Delta R/R$ vs. strain as a function of printed meandering line parameters (w, l, R, α), (FIG. 24B) $\Delta R/R$ vs. radius of block C2 at different strain values, and (FIG. 24C) $\Delta R/R$ vs. arm length of block C2 at different strain values.
Figure 30:
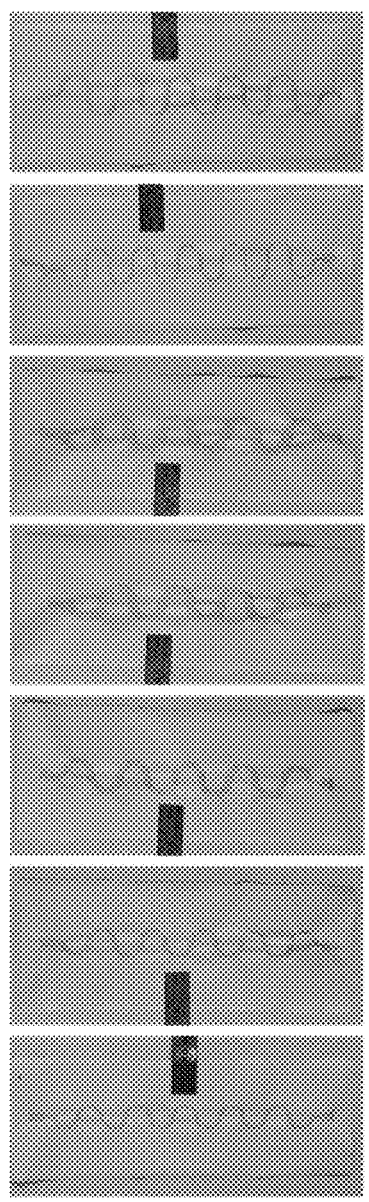
FIG. 30 shows Block A1-B2 meandering line design parameters.
Figure 31:
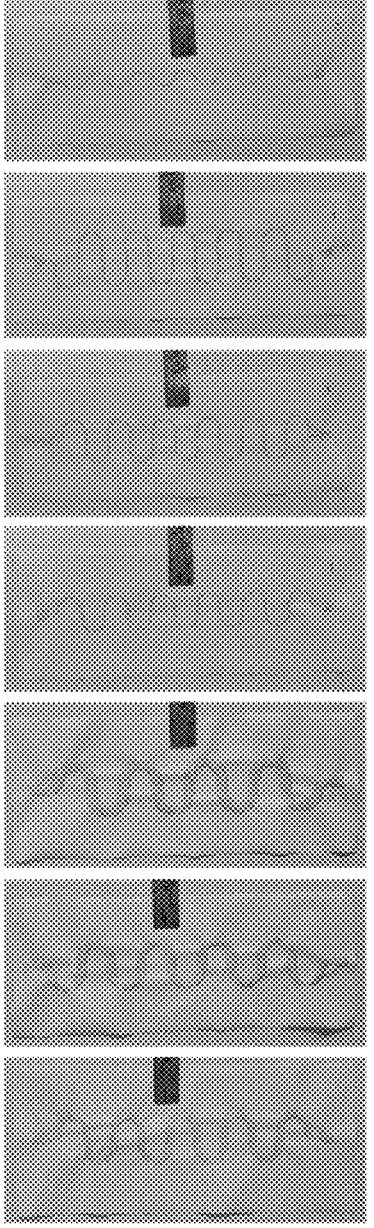
FIG. 31 shows Block B3-D1 meandering line design parameters.

To investigate the relationship of resistance change vs. meandering line design parameters (e.g., width (w), arm length (l), radius (R), angle (α)), different meandering lines were printed on the TPU printing layer (without lamination on the knit fabric and TPU encapsulation), and a final meandering line type was selected in the end to further study in the following sections. The meandering line design parameters along with digital pictures of the printed lines are given in FIGS. 30-32. Similar constant strain rate electromechanical tests were performed on the samples as was previously mentioned. The comparison of different meandering line types was made based upon ΔR/R values at 40% strains, which were obtained as a result of in-situ electromechanical tests. The results are shown in FIG. 24A. The figure shows ΔR/R vs. strain up to 40% applied strain. Each printed blocks were located on the perimeter of the plot according to decreasing ΔR/R value. The inner curves correspond to the applied strains of 10, 20, 30, 40%. Blocks A1 through A5 represent w=1 to 5 mm, l=0 mm, R=5 mm, and α=0° (width varies). Blocks B1 through B5 represent w=1 to 5 mm, l=5 mm, R=5 mm, and α=0° (width varies). Blocks C1 through C3 show w=1 mm, l=5, 10, 15 mm, R=5 mm, and α=0° (arm length varies). Blocks D1 through D4 denote w=1 mm, l=0 mm, R=5 mm, and α=−20, 20, 30, 45° (angle varies), and blocks E1 through E3 indicate w=1 mm, l=5 mm, R=5 mm, and α=−20, 0, 20° (angle varies). Total of 20 blocks were printed (three replications for each block). The dimensions of each block were tabulated in (FIGS. 30-32). In blocks A1-A5 and B1-B5, increasing the width (w) of the printed line decreased the value of ΔR/R. This might be attributed to crack formation and propagation across the width of the crest region of the meandering line, which might be the predominant effect in meandering lines with small width values. In blocks C1-C3, increasing the arm length (l) decreased the value of ΔR/R. In blocks D1-D4, increasing the angle (α) gave decreasing trend in ΔR/R. For the blocks E1-E3, decreasing the angle (α) yielded a decreasing trend in ΔR/R values. The printed lines (blocks: A5, B3, D3) did not follow the trend as it can be seen from FIG. 24A, which may be ascribed to uneven coating of the TPU film surface due to the variations in the screen-printing process. While finite element analysis (FEA) might be required to validate and compare the induced strain and stress on the printed lines and also the change in ΔR/R as a function of meandering line parameters, it is noted that a goal in this work is to evaluate the techno-economic performance of the patterned structures, ideally choosing a meandering line design that has a combination of high performance and low cost. The Blocks C2, B3, B5, and C3 had the lowest ΔR/R among the printed blocks (78.5, 73.1, 69.7, and 64.1Ω, respectively). The equivalent line length for each block type was calculated according to the resistance formula (R=ρL/wt). Averaged measured resistance (R, number of samples=3), resistivity (ρ) of 0.0002 Ω-cm, thickness (t) of 20 μm and printed width (w) were utilized in the calculation. Finally, the printing cost was calculated and plotted by finding the averaged ink amount (N=3) for a length of 11.5 cm and then multiplying it with the ink's cost ($4/g). Localized variation in these dimensions can expect to induce some uncertainty in the cost calculation. These effects would be two-fold. Increasing the thickness of the conductive layer would decrease the resistance of the line due to addition of more conductive material per unit length. The increased thickness would also increase materials usage and raise the cost of the printing. For the parameters used in this analysis, blocks E4, C2, D2, and D4 had the cheapest printing cost among the printed blocks (6.60, 6.00, 5.95, 5.43 cents, respectively). The block C2 was selected for further testing in following sections since its cost was much lower than blocks B5 and B3 (20 and 21 cents). Also, block C2 was less wide than the block C3 (22 mm vs. 27 mm). This architecture also occupies less printing space, thus allowing for a higher density of printed interconnects.

Figure 25A:
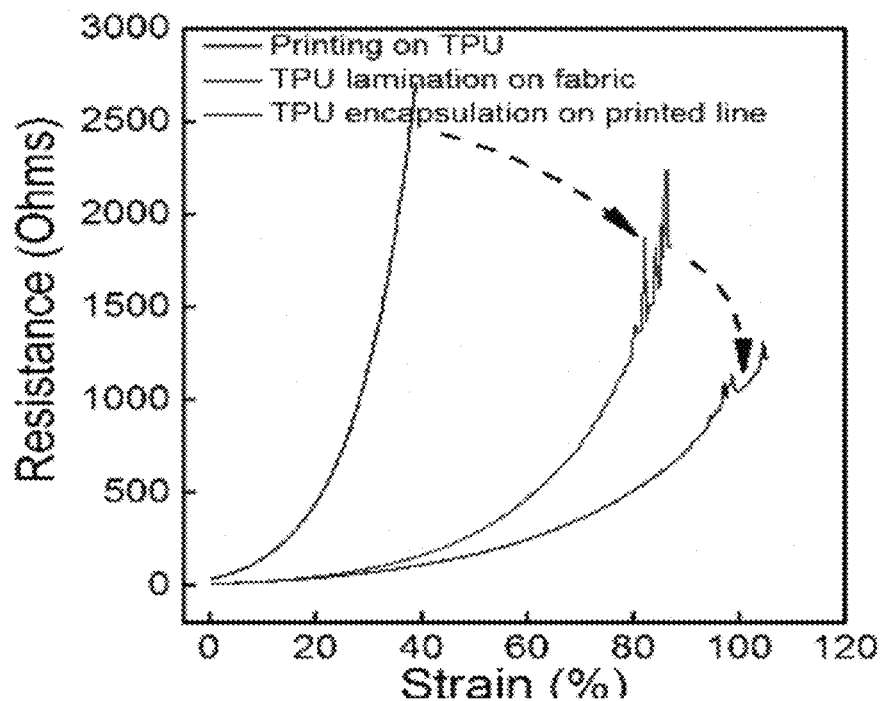
FIGS. 25A-25D show (FIG. 25A) One-time stretching test of each fabrication step samples (test speed: 5.08 cm/min), (FIG. 25B) cycling test of each fabrication step samples (test speed: 10.16 cm/min), (FIG. 25C) mechanical properties of constituents of multilayer structure, and (FIG. 25D) transverse contraction of the constituent layers and the final multilayer structure with axial strain.
Figure 25B:
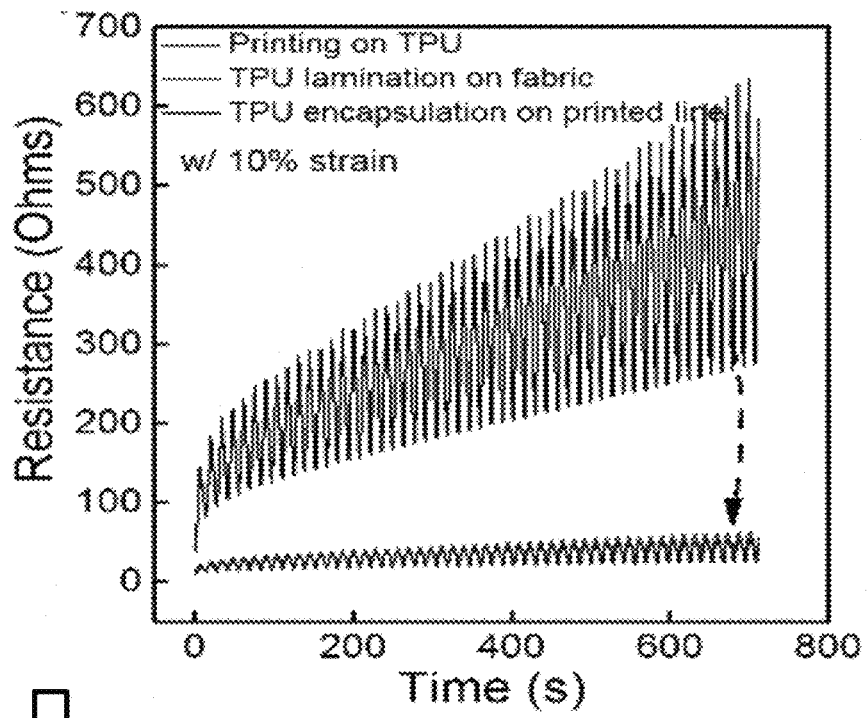
Figure 25C:
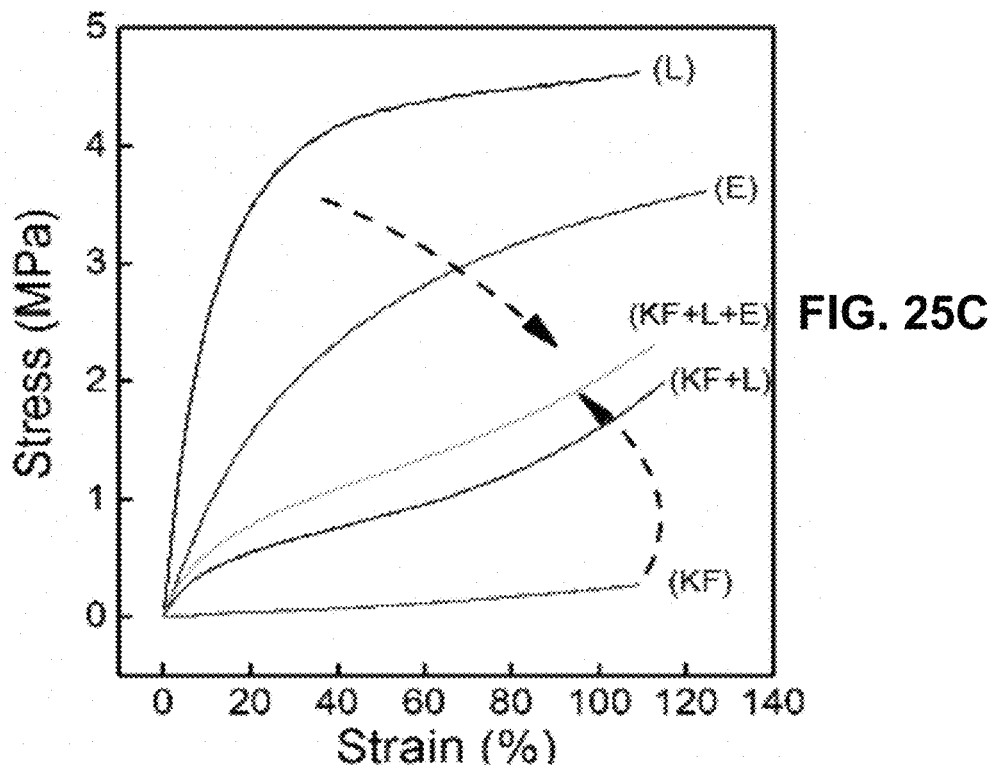
Figure 25D:
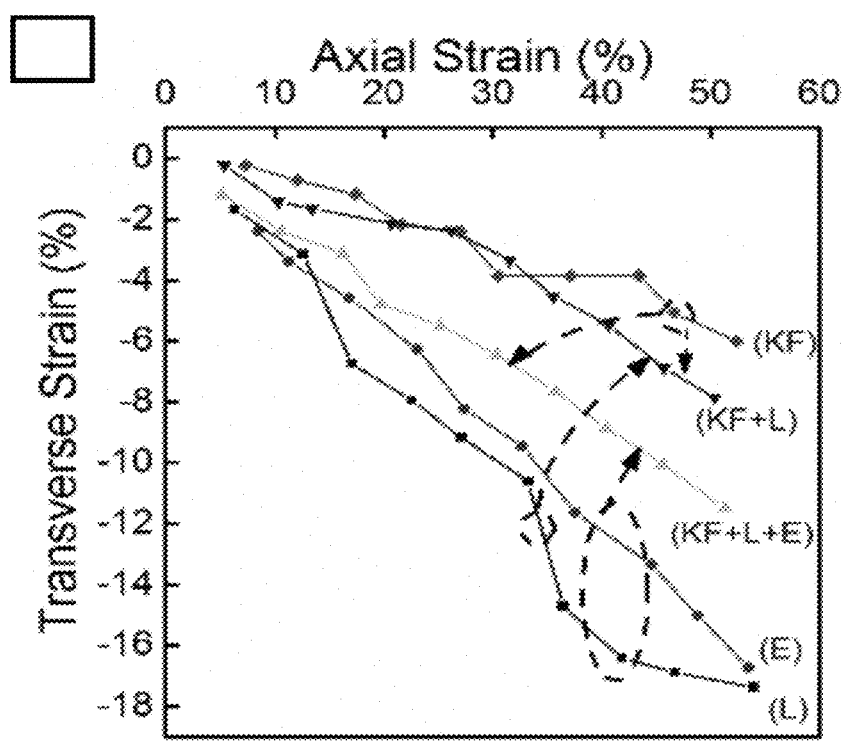
Figures 26A, 26B:
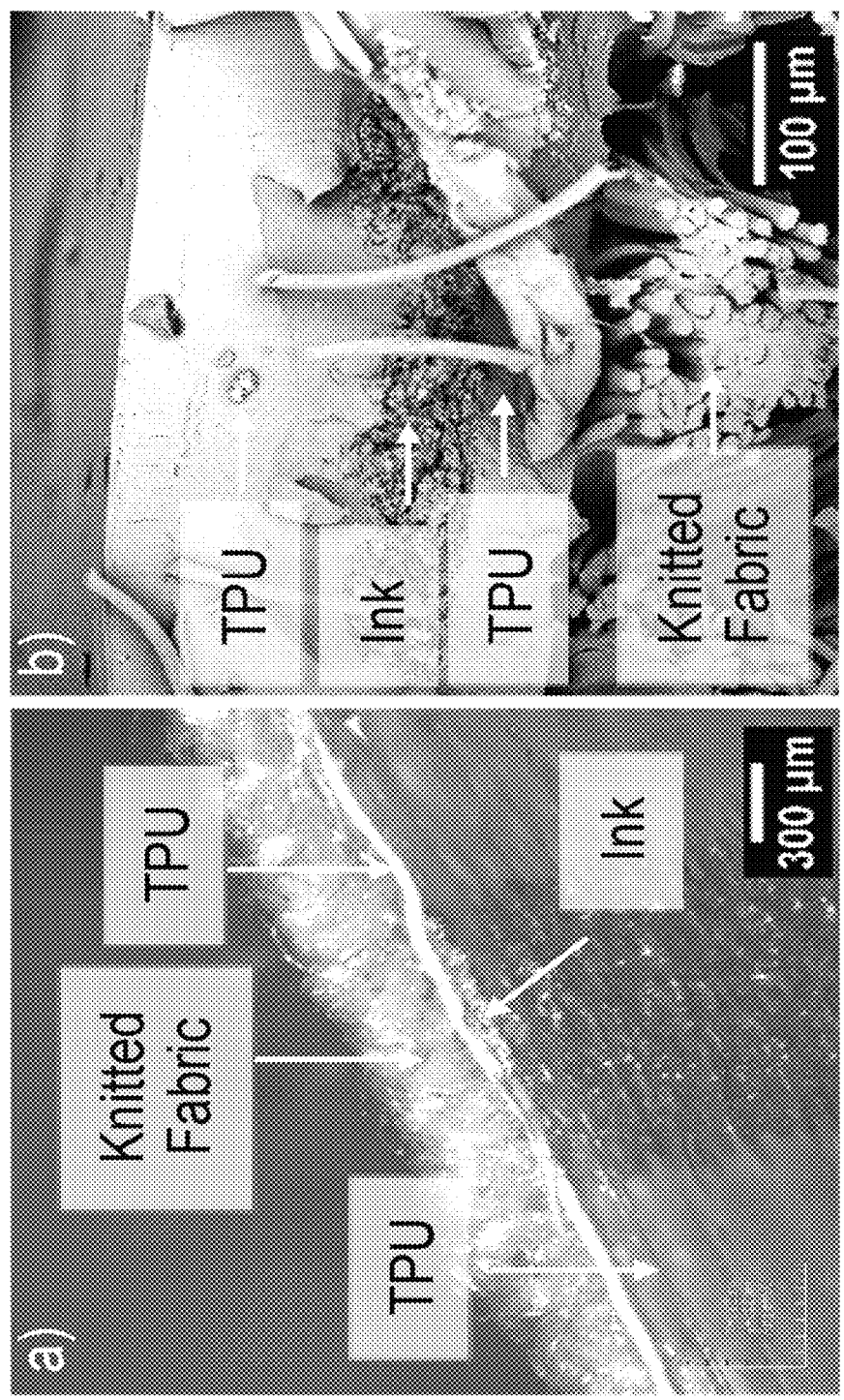
FIGS. 26A-26J show (FIG. 26A) an optical picture of TPU laminated and encapsulated multilayer stretchable interconnect structure, (FIG. 26B) a SEM cross-sectional view of multilayer stretchable interconnect structure, (FIGS. 26C-26F) digital microscope pictures with stretching of TPU film laminated knit fabric, (FIGS. 26G-26J) digital microscope pictures with stretching when TPU encapsulation layer was added on the printed line.
Figures 26C, 26D, 26E, 26F, 26G, 26H, 26I, 26J:
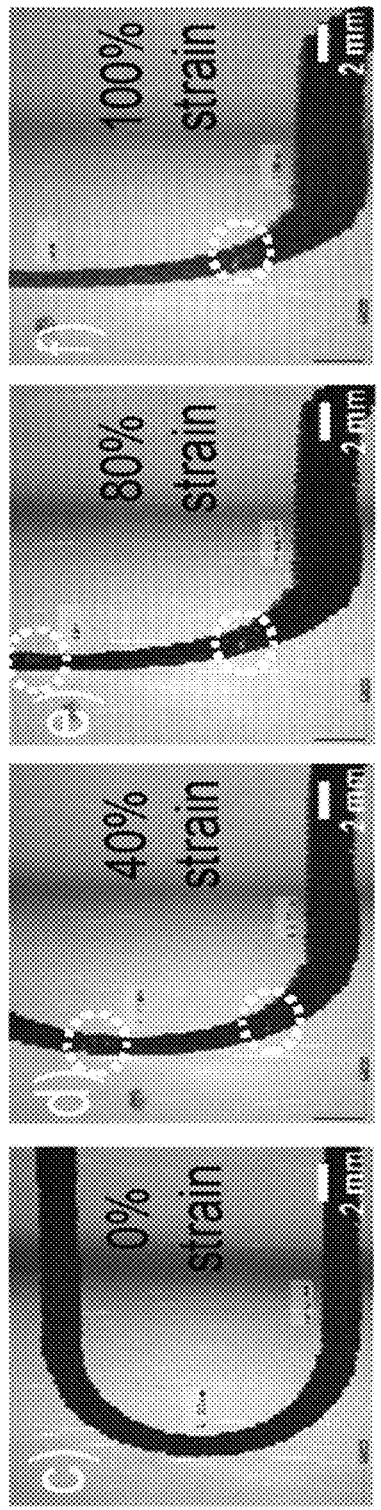

B. Lamination of TPU Printing Layer on Knit Fabric and Encapsulation of Conductive Ink The selected block C2 meandering line shape (w=1 mm, l=5 mm, R=5 mm, α=0° in Section III-A was used in this section. The fabrication procedure in FIG. 21A was followed as described in Section II-B. The meandering line was screen-printed onto the TPU printing layer (rectangular, 6 cm×16 cm). It was then laminated on the knit fabric. Afterwards, it was covered with a TPU film encapsulation (rectangular, 6 cm×16 cm). Heat laminated TPU film layer provides insulation and protects the printed lines from mechanical and environmental damage as other silicone and acrylic encapsulation coatings [23], [24]. In addition, it eliminates additional screen preparation and cleaning steps in screen-printing process. Optical microscopy and SEM cross-sectional pictures of the final multilayer structure are given in FIGS. 26A and 26B. Mechanical properties of each layer are given in FIGS. 25C and 25D. The TPU printing layer, the TPU encapsulation layer, and the knit fabric are denoted as L, E, and KF, respectively. Lamination of TPU printing layer on knit fabric is denoted as KF+L, and the combination of all of the layers is shown as KF+L+E. FIG. 25C shows the stress vs. strain graph of each layer and the final laminated multilayer structure. Young's modulus (modulus=stress/strain, calculated at 10% strain) of the printing layer (L), the encapsulation layer (E), and the knit fabric was calculated as 248, 90, and 1.4 kPa, respectively. The Young's modulus for KF+L and KF+L+E were found as 37 kPa and 52 kPa. Addition of the individual layers created a new multilayer structure whose mechanical properties fall between the mechanical properties of the individual layers. FIG. 25D describes how much transverse contraction occurs with an axial strain (e.g., Poisson's ratio=−transverse contraction/axial strain). The Poisson's ratios for L, E, KF+L+E, KF+L, and KF were calculated from the slope of the curves as 0.4, 0.3, 0.22, 0.14, and 0.09, respectively. Similar to the Young's modulus, Poisson's ratio for the multilayer structure falls between Poisson's ratio of the constituent layers.

Figure 24B:
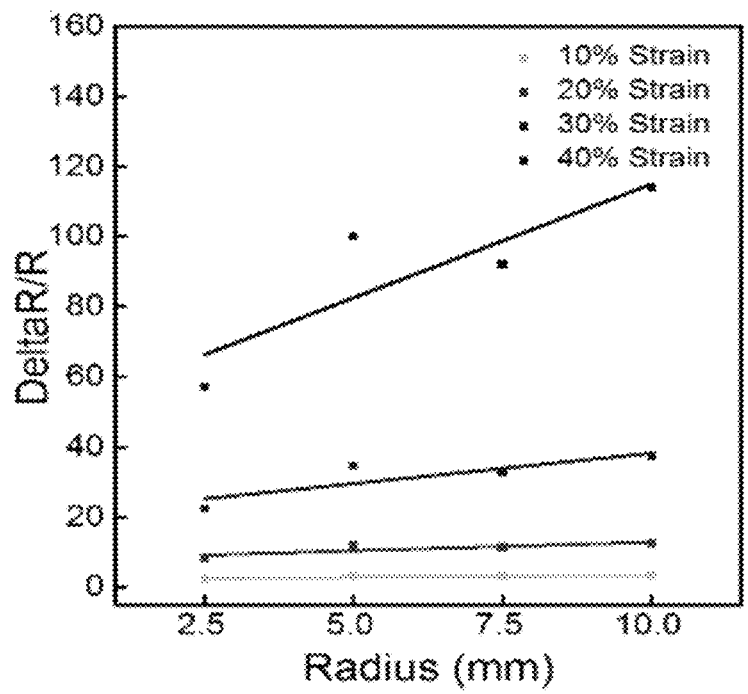
Figure 24C:
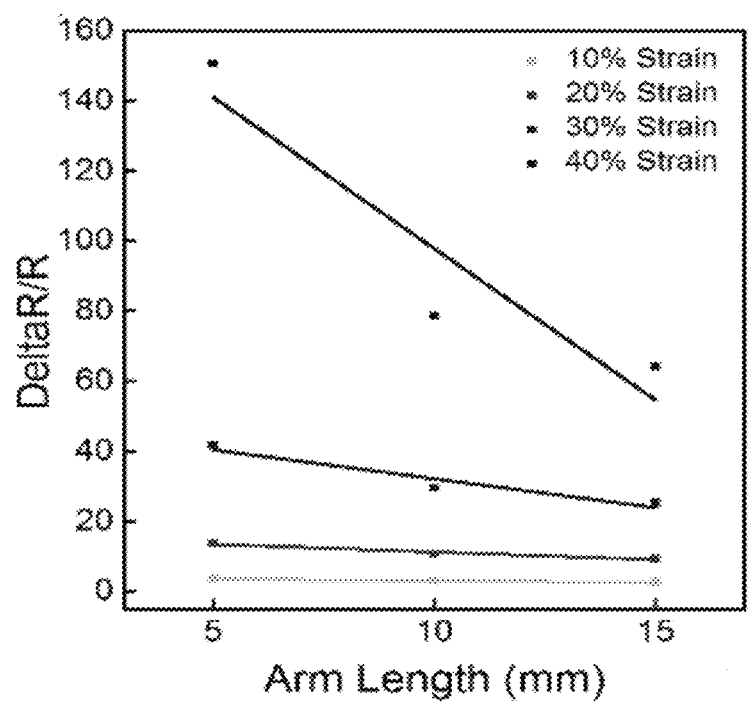

To investigate the effect of each step (lamination and encapsulation) on the electrical properties of the printed line, one-time in-situ stretching tensile test and cyclic tensile test were performed. The results are presented in FIGS. 25A and 25B. FIG. 25A shows the resistance change vs. strain for the test sample as it goes through each fabrication step. Block C2 printed TPU film had the sharpest strain change with strain, and its electrical failure was at 52.47%±8.28% strain. When the printed layer was laminated on the knit fabric, the failure strain went up to 78.82%±11.68%. As the TPU encapsulation layer was applied to the rest of the layered structure, the failure strain value went up to 103.91%±5.31%. The cyclic tensile test results (10% strain and 100 cycles) of each fabrication step are shown in FIG. 25B. The block C2 printed TPU film had the highest resistance change when the number of cycles increased. The cyclic tensile testing of the multilayer structure before and after the encapsulation layer had a very slight difference. The increase in stretchability in the one-time stretching test and cyclic tensile test was attributed to both lamination temperature and TPU encapsulation. The TPU film lamination and TPU encapsulation process temperatures (125° C.) were higher than the ink curing temperature (60° C.). Thus, this resulted in a resistance drop of about 70% in the ink. Since the TPU encapsulation layer enclosed the ink on the topside, an improvement in one time stretching and cyclic tensile testing properties was observed due to the retardation of deformation of the ink layer. The encapsulation layer inhibited significant crack formation with extension and helped to recover the ink layer to its initial state. Improvement of the results in FIGS. 25A and 25B can be explained by investigation of the microstructure of the ink as it is strained. FIGS. 26C-26F shows the crack formation on the printed line with strain for the printing layer laminated knit fabric sample. The visible cracks (encircled) were observed on the crest region of the meandering line starting at 20% strain and on. However, no visible cracks were found after TPU film encapsulation on the printed line in FIGS. 26G-26J. This explained the early resistance increase in low stain values in FIG. 26A. When the sample was uniaxially stretched, the width of the arm region of the meandering line increased, and the crest region of the meandering line was narrowed and elongated. In contrast, the length of crest region of the meandering line extended, and its peak width decreased. To investigate which region of the meandering line (crest vs. arm) had the most effect on the $\Delta R/R$ value, the C2 blocks with various radii (R=2.5, 5, 7.5, and 10 mm) and arm length values (l=5, 10, and 15 mm) were printed on the TPU film. It is helpful to note that an increased radius corresponds to increased crest length of the printed line (perimeter of crest region=$2\pi R$). The results are given in FIGS. 24B and 24C. FIG. 24B shows $\Delta R/R$ vs. radius change at different strain values. As the radius of the meandering line was increased, the deformation in the printed line increased. This testing scenario corresponds to the stretched sample conditions in FIGS. 26C-26J. The meandering line's crest region length increases with stretching, thus, the deformation ($\Delta R/R$) of the printed line increases. Increasing the arm length decreased the deformation in the meandering line, shown in FIG. 24C. However, when the sample was stretched in FIGS. 26G-26J, the arm length did not change (its width was widened). Therefore, it was concluded that the crest region was the region resulting in a significant resistance increase as the sample was elongated.

Figures 27A, 27B:
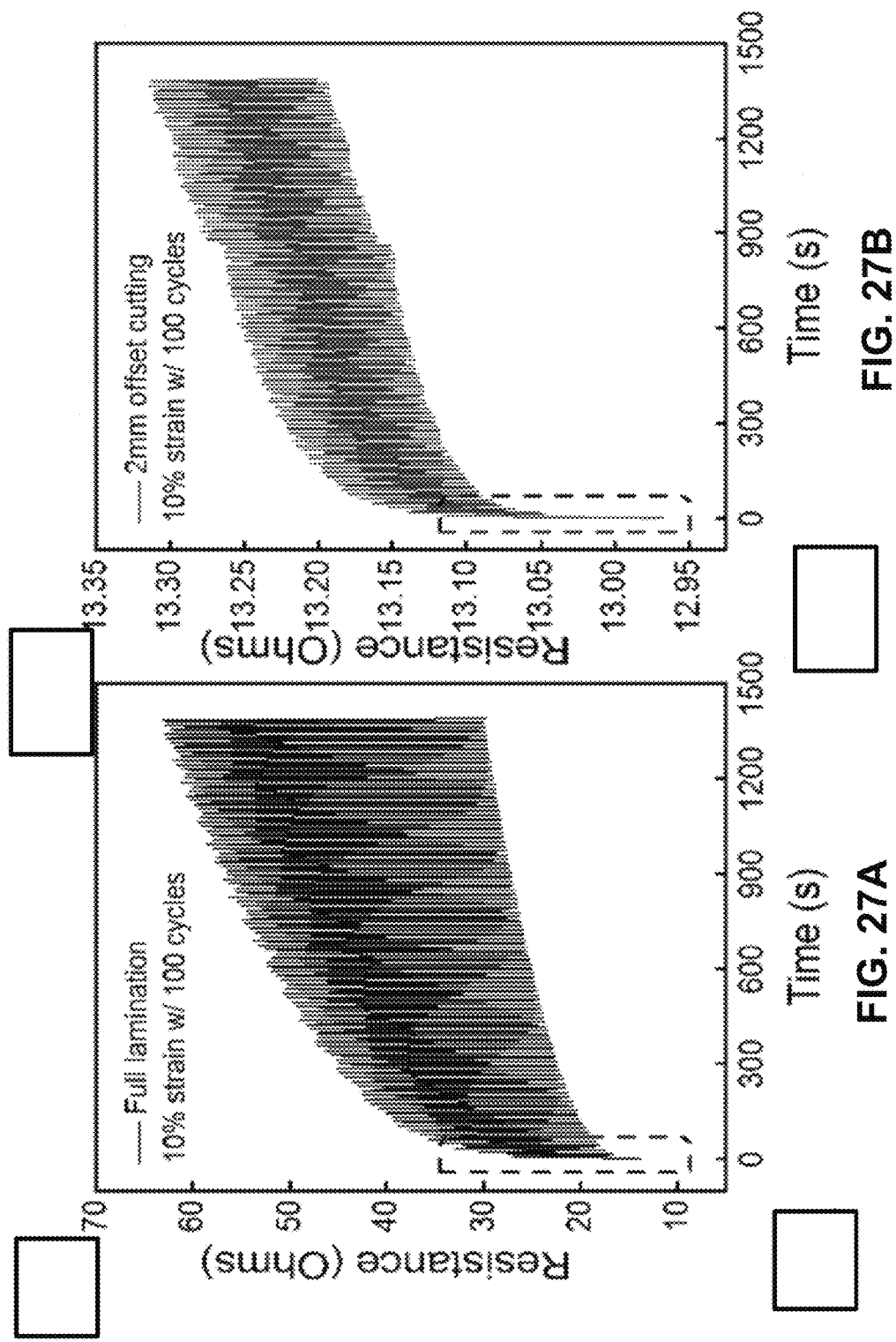
Figure 28B:
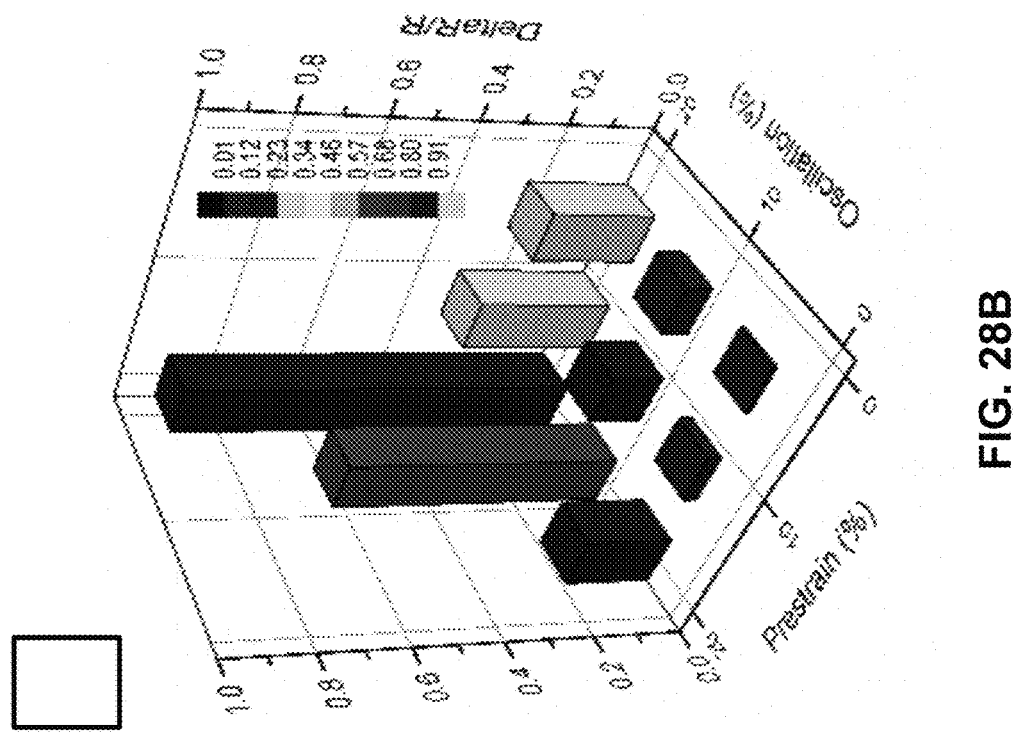
FIGS. 28A-28D show graphs demonstrating (FIG. 28A) one-time stretching test of whole area TPU lamination vs. 2 mm and 4 mm offset meandering shaped TPU lamination (test speed: 5.08 cm/min), (FIG. 28B) ΔR/R vs. discrete pre-strain and cyclic tensile strains (test speed: 10.16 cm/min), (FIG. 28C) 1000 cycle cycling test with 10% prestrain and succeeding 10% cycling strain (test speed: 10.16 cm/min), (FIG. 28D) zoom-out region of the marked region in FIG. 28C.
Figure 28A:
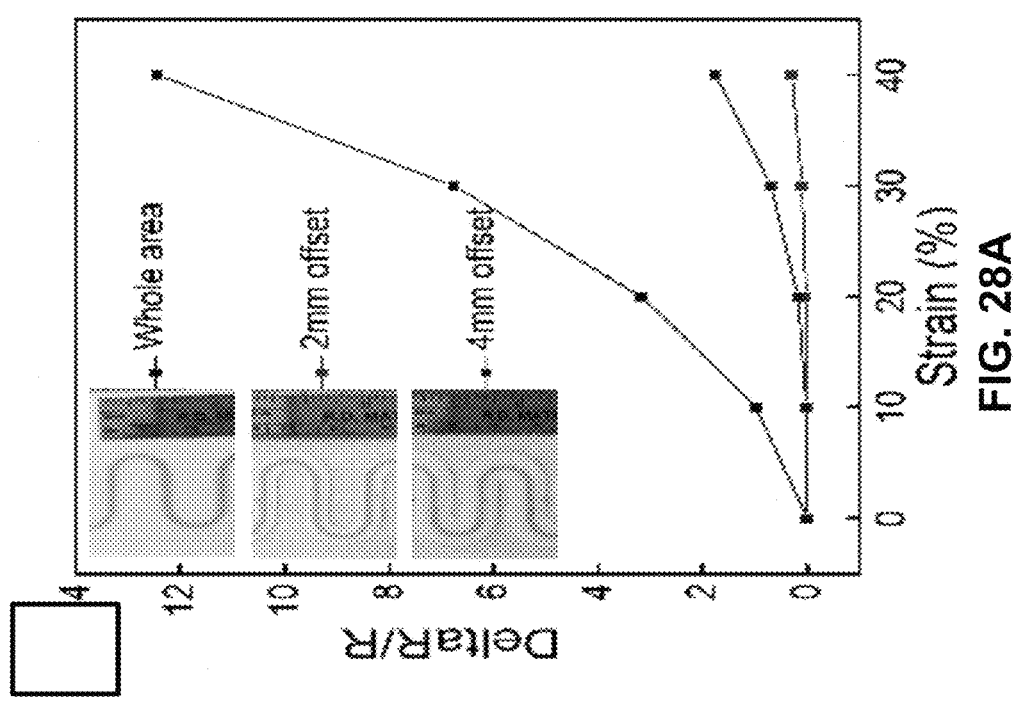

Thus far, only rectangular cut (6 cm×16 cm) samples of the printing layer and encapsulation layer lamination onto knitted fabric were presented, shown in FIG. 21A. The effect of removing excess TPU printing layer and encapsulation layer on the electrical properties of the printed interconnects is studied from now on, shown in FIG. 21B. A similar fabrication procedure was followed as described in Section II-B except the dimensions of the TPU printing layer and TPU encapsulation layer were determined by offsetting the printed Block C2 meandering design by amount of $w_{offset}$, as shown in FIG. 21D. Two offset values (2 mm and 4 mm) were tested. Similar one-time stretching and cyclic tensile tests were performed to explore the effect of removing extra material from the printing and encapsulation layers. FIGS. 27A-27B shows the cycling testing (10% strain and 100 cycles) results of whole area (rectangular) vs. 2 mm offset cut (meandering shaped TPU layer) multilayer structure. The latter had only 0.23Ω resistance change at the end of 100 cycles, whereas, the rectangular cut lamination had a resistance change of 16.37Ω. The first three oscillation cycles of FIGS. 27A-27B are given in FIGS. 27C and 27D. In FIG. 27C, an initial straining of the sample by 10% resulted in a resistance increase of 95.96%, and the subsequent second and third cycles had a percent resistance increase of 13.10% and 7.97%. The percent resistance change trend decreased with succeeding stretching cycles (e.g., less deformation in the ink with succeeding cycles). In contrast, the percent resistance increase in FIG. 27D was only 1.13%, and the following cycles had 0.19% and 0.1% resistance increase. For the meandering shaped multilayer interconnect (FIG. 21B), the applied strain resulted in extension of the knit fabric between the printed meandering lines, where there was no lamination of TPU film. This part of the fabric underwent more straining without imposing more strain on the ink, which produced high flexibility while minimizing resistance change with strain. One-time stretching results are shown in FIG. 28A, which shows up to 40% strain. The inset image in FIG. 28A shows the pictures of the fabricated samples. The 2 mm offset cut sample showed the smallest resistance change ($\Delta R/R=0.29$) at 40% strain. The 4 mm offset and full area laminated multilayer interconnects had $\Delta R/R$ values of 1.75 and 12.43, respectively. Removing the excess material resulted in less strain in the ink layer, which contributed to smaller resistance change upon elongation. The removal of TPU layers between two subsequent arms of printed meandering lines yielded larger strain values for a constant $\Delta R/R$ value compared to whole area rectangular lamination.

Figure 28D:
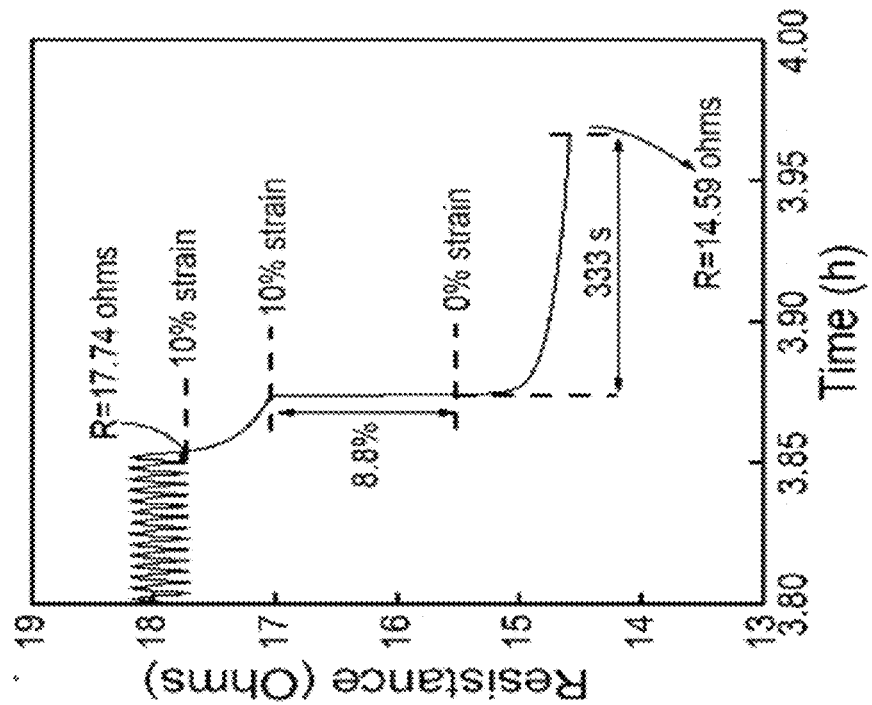
Figure 28C:
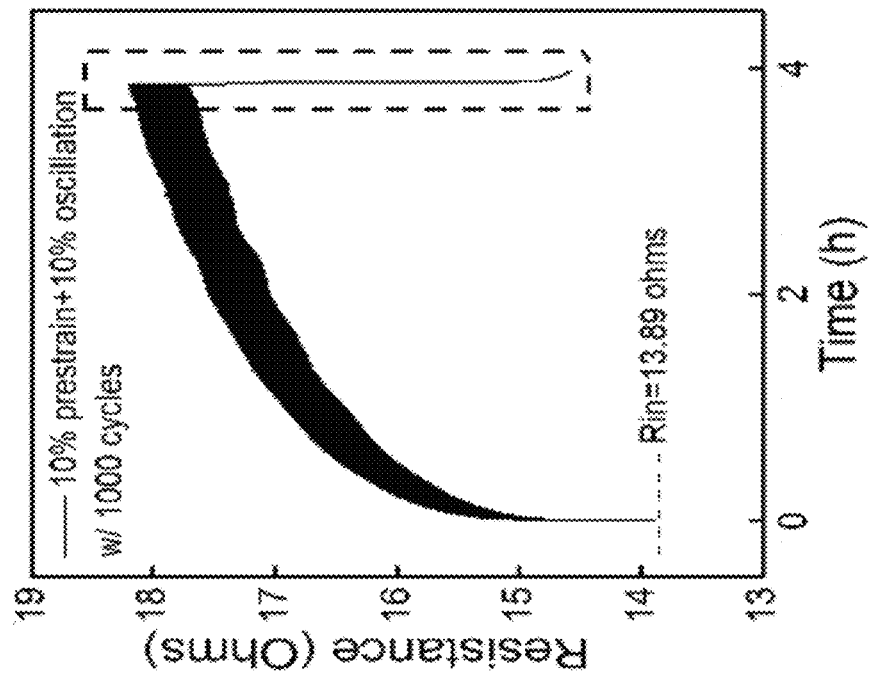

To simulate the daily use of the garment (e.g., straining during dressing and additional strains due to body movement), the multilayer stretchable printed line structure (FIG. 21B(b), $w_{offset}$=2 mm) was exposed to various pre-strain and cyclic strains in cyclic tensile testing. In other words, the test sample was pre-strained by a certain amount on tensile testing equipment, and then subsequent 100 cycles were applied with an additional cyclic tensile strain. The pre-strain and cyclic tensile strain values were selected as 5%, 10%, and 20%. The result is given in FIG. 28B. At a constant pre-strain value, increasing the cyclic strain value increased the ΔR/R. Similar increasing trend in ΔR/R was obtained for increasing pre-strain value at constant cyclic tensile strain. The lowest ΔR/R value calculated was with 5% pre-strain+5% cyclic tensile strain (ΔR/R=0.009). The highest ΔR/R value was with 20% pre-strain+20% cyclic strain (ΔR/R=0.91), as expected. Higher total strain (pre-strain+cyclic strain) led to increased deformation in the printed line. To further investigate electrical properties of the stretchable meandering printed lines a 1,000 cycles were performed on the cyclic tensile test with a 10% pre-strain+10% cyclic strain. The results of the test are given in FIGS. 28C and 28D. The resistance curve slightly levels off over time in FIG. 28C. This was attributed to the decreasing percent resistance change of the printed line with an increasing number of cycles, as explained in FIG. 27D. The printed line resistance changed only by 3.85Ω at the end of 1,000 cycles, shown in FIG. 28D. When the tensile tester crosshead was brought down from 10% strain to 0% strain, the recovery in the resistance was 8.8%. At 0% strain, the resistance of the sample decreased exponentially over time due to the recovery of ink and the multilayer substrate. The resistance value was 14.59Ω after 333 seconds. This value could further decrease over time if the decreasing slope of the resistance was taken into account in the rectangular marked area in FIG. 28C. It is important to reiterate that the testing in FIGS. 28C and 28D mimics a real human scenario, where the pre-strain is the initial strain generated on the printed line when a garment is placed on the body. This is followed by a cyclic strain that simulates the daily use of the garment. The self-healing of the resistance at the end of the test replicates the garment removal and storage.

C. Washing Durability and Stretchable Interconnects Demonstrations

An accelerated wash test (AATCC 61-2a) was performed to examine the effectiveness of the TPU encapsulation on the ink's electrical performance. One accelerated wash test is equivalent to 5 home launderings. A total of six samples with and without TPU encapsulation were fabricated according to the procedure in FIG. 21A. The samples were placed into metal containers with 50 steel spheres and washed at 49° C. with a powder detergent. The samples without TPU encapsulation were not conductive after initial 5 home washing cycles. However, the samples with the TPU encapsulation ($R_{initial}$=7.45Ω±1.73Ω) were still conductive after 100 washing cycles with a resistance increase of 4.6Ω.

Figures 33C, 33D:
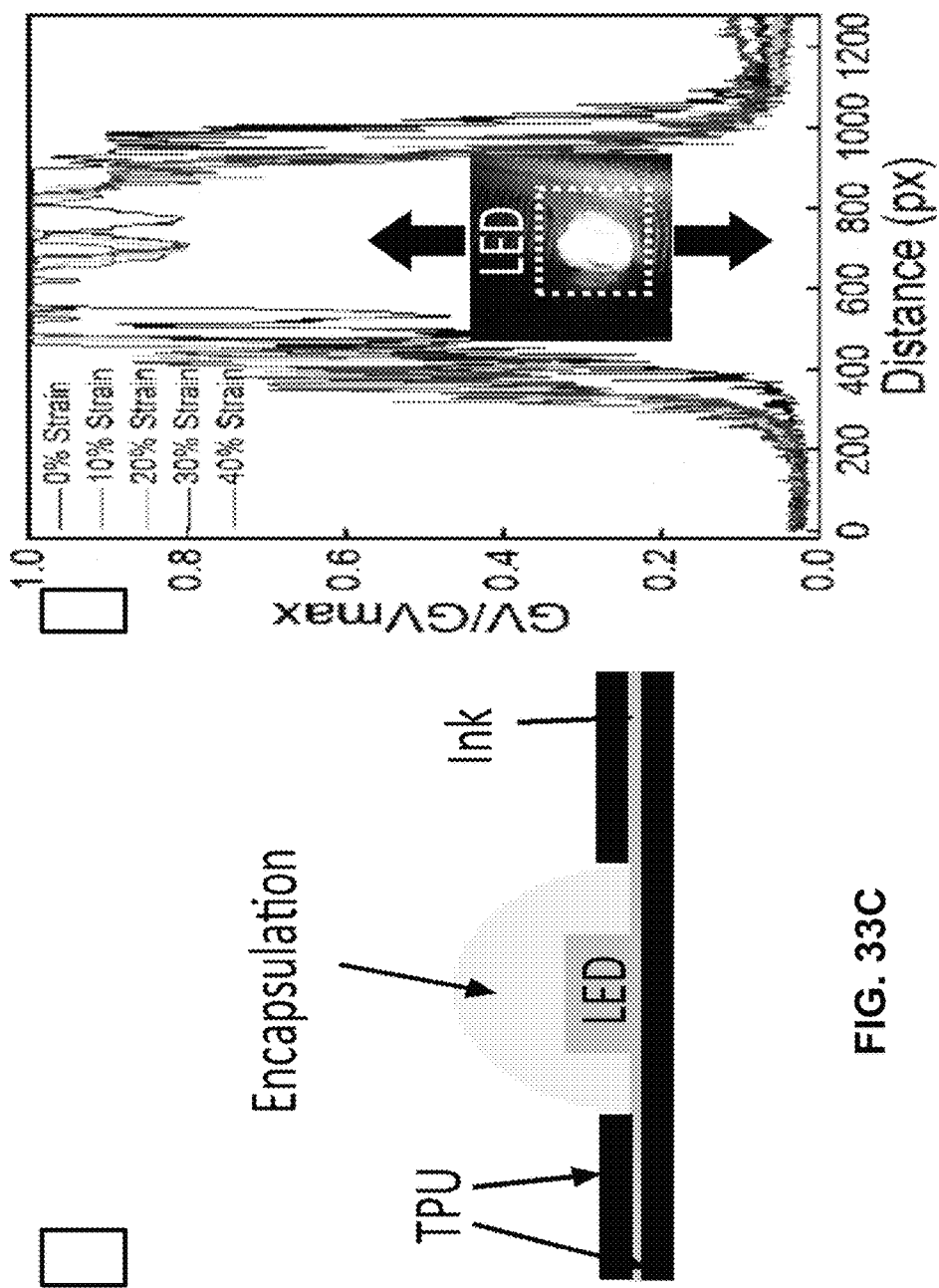

To demonstrate this technology, a surface mount LED was integrated on the stretchable printed line with a 51Ω surface mount resistor to show the applicability and use of the proposed stretchable printed meandering lines, shown in FIGS. 33A and 33B. The LED was bonded to conductive traces by using silver epoxy (CircuitWorks 2400). It was then encapsulated with UV curable encapsulant (Dymax 9001) to give mechanical stiffening and eliminate debonding of LED. The cross-sectional image of its integration is shown in FIG. 33C. The integrated LED was powered with a 3V coin cell battery. Afterwards, the LED integrated printed line was stretched up 100% strain with a custom-built straining device, and simultaneously the surface picture was taken with a digital microscope in a dark room. The LED light turned off above 80% strain due to the resistance increase in the printed line, which decreased the voltage drop across the LED. However, the LED light turned back on with the recovery of the printed line. The LED light intensity up to 40% strain is given in FIG. 33D. The intensity plot was obtained by image processing of the captured image in MATLAB software. The vertical axis represents normalized grayscale value ($GV/GV_{max}$). It was observed that the light intensity did not change up to 40% strain. However, a horizontal shift was observed in the graph due to out-of-plane rotation of the LED during stretching. FIGS. 34A-34C and 35 further demonstrate a flexible interconnect containing an integrated LED.

Figures 29A, 29B:
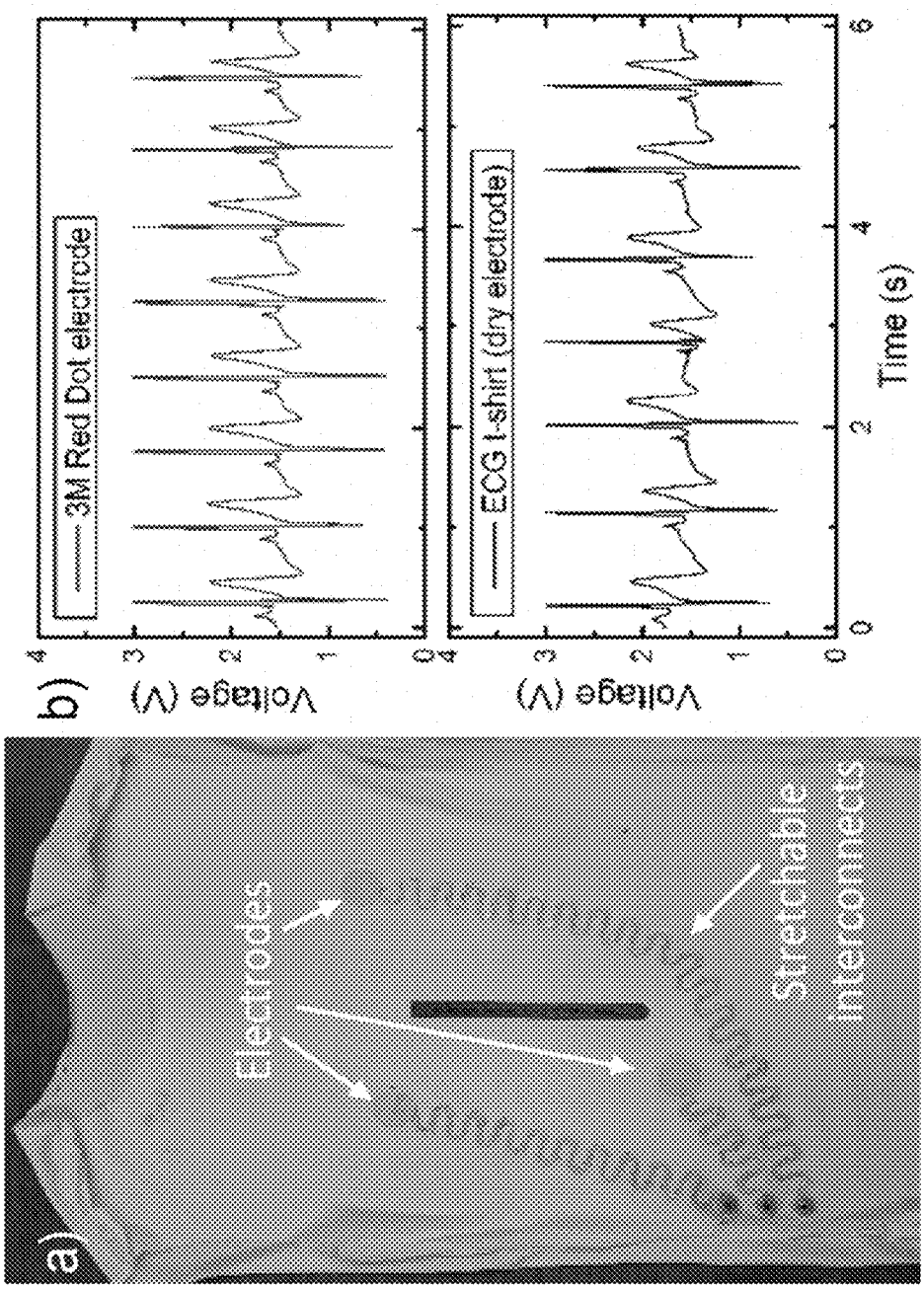
FIGS. 29A-29B show (FIG. 29A) the inner side of a fabricated ECG t-shirt and (FIG. 29B) recorded ECG signals from 3M Red Dot electrode and ECG t-shirt.

For a second demonstration, an electrocardiography (ECG) shirt was fabricated to show the use of fabricated stretchable printed lines to monitor the electrical activity of the heart. FIG. 29A shows the inner side of the t-shirt, where three 30 mm printed dry electrodes [28] were printed along with stretchable meandering lines. The distance between electrode pairs was kept at 13 cm. Lead I of Einthoven's triangle configuration was used to measure the potential difference between electrode pairs. ECG measurement was made with a Vernier ECG signal acquisition device (1 V/1 mV gain, sampling rate: 100 Hz). A healthy male subject wore the fabricated t-shirt, and an ECG measurement was taken while the subject was standing. FIG. 29B shows the recorded ECG signals with 3M Red Dot electrode (as reference) and with the ECG shirt. The acquired ECG signals show comparable ECG signals with characteristic PQRST electrocardiogram peaks.

Discussion

A multilayer stretchable interconnect design was fabricated by screen-printing Ag/AgCl ink on thermoplastic polyurethane (TPU) film. Its subsequent heat lamination onto a knit fabric, and a TPU encapsulation on the ink layer yielded a novel multilayer stretchable interconnect structure.

Printing the meandering and straight line on the TPU film layer provided high failure strain values compared to the knit fabric alone. A set of design of experiments was conducted to determine the most suitable meandering line by changing the meandering line parameters (width, arm length, radius, and angle). Block C2 (w=1 mm, l=5 mm, R=5 mm, α=0° was chosen due to its low ΔR/R value and inexpensive printing cost.

Lamination of the printing layer on the knit fabric and encapsulation of the ink layer with TPU film were explored. The conductive ink printed TPU layer with a knit fabric backing decreased deformation on the ink. Moreover, the TPU film encapsulation on the ink layer prevented the ink from significantly cracking and helped to recover the ink to its initial position.

The effect of decreasing the area and shape of the printing and encapsulation layer was investigated. It was found that the meandering shaped printing and encapsulation layers significantly decreased the resistance change in one time stretching and cycling tests. The multilayer meandering shaped structure was cycled 1,000 times in a simulation of a human use scenario, and only 0.7Ω resistance change was observed. In our study, the maximum stretchability achieved was about 110% with the 2 mm offset sample. Materials factors of the ink not considered in this work such as chemical and physical properties of the polymer, solvent and surfactant type, and filler type and its concentration provide additional opportunities for improved performance. In addition, synergy of novel elastic ink chemistries with strain-relief printed line designs may yield higher stretchability values.

Finally, a surface mount LED integration on stretchable printed lines and an ECG shirt with meandering lines were demonstrated. The integrated LED was resistant to stretching, flexing and twisting, which might be used in wearable optical based sensors. Moreover, the ECG shirt acquired similar ECG signals compared to the reference electrodes. The proposed inexpensive and washable (100 wash cycles) multilayer interconnects design has utmost importance in integration of sensors, antennas, and energy harvesting devices on garments for wearable electronics.

REFERENCES FOR EXAMPLE 8

[1] M. Ciocchetti, C. Massaroni, P. Saccomandi, M. A. Caponero, A. Polimadei, D. Formica, and E. Schena, "Smart Textile Based on Fiber Bragg Grating Sensors for Respiratory Monitoring: Design and Preliminary Trials," *Biosensors*, vol. 5, no. 3, pp. 602-615, September 2015.

[2] F. M. Kelly, L. Meunier, C. Cochrane, and V. Koncar, "Polyaniline: Application as solid state electrochromic in a flexible textile display," *Displays*, vol. 34, no. 1, pp. 1-7, January 2013.

[3] Q. He, Z. Zeng, Z. Yin, H. Li, S. Wu, X. Huang, and H. Zhang, "Fabrication of Flexible MoS2 Thin-Film Transistor Arrays for Practical Gas-Sensing Applications," *Small*, vol. 8, no. 19, pp. 2994-2999, October 2012.

[4] Y. He, W. Chen, X. Li, Z. Zhang, J. Fu, C. Zhao, and E. Xie, "Freestanding Three-Dimensional Graphene/MnO2 Composite Networks As Ultralight and Flexible Supercapacitor Electrodes," *ACS Nano*, vol. 7, no. 1, pp. 174-182, January 2013.

[5] Y. Cheng, R. Wang, J. Sun, and L. Gao, "Highly Conductive and Ultrastretchable Electric Circuits from Covered Yarns and Silver Nanowires," *ACS Nano*, vol. 9, no. 4, pp. 3887-3895, April 2015.

[6] X. Pu, L. Li, H. Song, C. Du, Z. Zhao, C. Jiang, G. Cao, W. Hu, and Z. L. Wang, "A Self-Charging Power Unit by Integration of a Textile Triboelectric Nanogenerator and a Flexible Lithium-Ion Battery for Wearable Electronics," *Adv. Mater.*, vol. 27, no. 15, pp. 2472-2478, April 2015.

[7] C. Mattmann, O. Amft, H. Harms, G. Troster, and F. Clemens, "Recognizing Upper Body Postures using Textile Strain Sensors," in *2007 11th IEEE International Symposium on Wearable Computers*, 2007, pp. 29-36.

[8] K. Cherenack, C. Zysset, T. Kinkeldei, N. Münzenrieder, and G. Tröster, "Woven Electronic Fibers with Sensing and Display Functions for Smart Textiles," *Adv. Mater.*, vol. 22, no. 45, pp. 5178-5182, December 2010.

[9] Y. Sun and J. A. Rogers, "Structural forms of single crystal semiconductor nanoribbons for high-performance stretchable electronics," *J. Mater. Chem.*, vol. 17, no. 9, pp. 832-840, February 2007.

[10] S. P. Lacour, S. Wagner, Z. Huang, and Z. Suo, "Stretchable gold conductors on elastomeric substrates," *Appl. Phys. Lett.*, vol. 82, no. 15, pp. 2404-2406, April 2003.

[11] T. Someya, Y. Kato, T. Sekitani, S. Iba, Y. Noguchi, Y. Murase, H. Kawaguchi, and T. Sakurai, "Conformable, flexible, large-area networks of pressure and thermal sensors with organic transistor active matrixes," *Proc. Natl. Acad. Sci. U. S. A.*, vol. 102, no. 35, pp. 12321-12325, August 2005.

[12] H. C. Ko, M. P. Stoykovich, J. Song, V. Malyarchuk, W. M. Choi, C.-J. Yu, J. B. Geddes Iii, J. Xiao, S. Wang, Y. Huang, and J. A. Rogers, "A hemispherical electronic eye camera based on compressible silicon optoelectronics," *Nature*, vol. 454, no. 7205, pp. 748-753, August 2008.

[13] D. S. Gray, J. Tien, and C. S. Chen, "High-Conductivity Elastomeric Electronics," *Adv. Mater.*, vol. 16, no. 5, pp. 393-397, March 2004.

[14] K. L. Lin and K. Jain, "Design and Fabrication of Stretchable Multilayer Self-Aligned Interconnects for Flexible Electronics and Large-Area Sensor Arrays Using Excimer Laser Photoablation," *IEEE Electron Device Lett.*, vol. 30, no. 1, pp. 14-17, January 2009.

[15] H.-J. Kim, C. Son, and B. Ziaie, "A multiaxial stretchable interconnect using liquid-alloy-filled elastomeric microchannels," *Appl. Phys. Lett.*, vol. 92, no. 1, p. 011904, January 2008.

[16] F. Bossuyt, T. Vervust, and J. Vanfleteren, "Stretchable Electronics Technology for Large Area Applications: Fabrication and Mechanical Characterization," *IEEE Trans. Compon. Packag. Manuf. Technol.*, vol. 3, no. 2, pp. 229-235, February 2013.

[17] Y.-Y. Hsu, M. Gonzalez, F. Bossuyt, J. Vanfleteren, and I. De Wolf, "Polyimide-Enhanced Stretchable Interconnects: Design, Fabrication, and Characterization," *IEEE Trans. Electron Devices*, vol. 58, no. 8, pp. 2680-2688, August 2011.

[18] N. Lu, C. Lu, S. Yang, and J. Rogers, "Highly Sensitive Skin-Mountable Strain Gauges Based Entirely on Elastomers," *Adv. Funct. Mater.*, vol. 22, no. 19, pp. 4044-4050, October 2012.

[19] S. Lee, S. Shin, S. Lee, J. Seo, J. Lee, S. Son, H. J. Cho, H. Algadi, S. Al-Sayari, D. E. Kim, and T. Lee, "Ag Nanowire Reinforced Highly Stretchable Conductive Fibers for Wearable Electronics," *Adv. Funct. Mater.*, vol. 25, no. 21, pp. 3114-3121, June 2015.

[20] Q. Li and X. Tao, "A stretchable knitted interconnect for three-dimensional curvilinear surfaces," *Text. Res. J.*, vol. 81, no. 11, pp. 1171-1182, July 2011.

[21] Q. Li and X. M. Tao, "Three-dimensionally deformable, highly stretchable, permeable, durable and washable fabric circuit boards," *Proc. R. Soc. Lond. Math. Phys. Eng. Sci.*, vol. 470, no. 2171, p. 20140472, November 2014.

[22] T. H. J. van Osch, J. Perelaer, A. W. M. de Laat, and U. S. Schubert, "Inkjet Printing of Narrow Conductive Tracks on Untreated Polymeric Substrates," *Adv. Mater.*, vol. 20, no. 2, pp. 343-345, January 2008.

[23] M. Suh, K. E. Carroll, E. Grant, and W. Oxenham, "Effect of fabric substrate and coating material on the quality of conductive printing," *J. Text. Inst.*, vol. 104, no. 2, pp. 213-222, February 2013.

[24] B. Karaguzel, C. R. Merritt, T. Kang, J. M. Wilson, H. T. Nagle, E. Grant, and B. Pourdeyhimi, "Flexible, durable printed electrical circuits," *J. Text. Inst.*, vol. 100, no. 1, pp. 1-9, March 2009.

[25] S. Takamatsu, T. Lonjaret, E. Ismailova, A. Masuda, T. Itoh, and G. G. Malliaras, "Wearable Keyboard Using Conducting Polymer Electrodes on Textiles," *Adv. Mater.*, p. n/a-n/a, November 2015.

[26] K.-S. Kim, K.-H. Jung, and S.-B. Jung, "Design and fabrication of screen-printed silver circuits for stretchable electronics," *Microelectron. Eng.*, vol. 120, pp. 216-220, May 2014.

[27] N. Matsuhisa, M. Kaltenbrunner, T. Yokota, H. Jinno, K. Kuribara, T. Sekitani, and T. Someya, "Printable elastic conductors with a high conductivity for electronic textile applications," *Nat. Commun.*, vol. 6, p. 7461, June 2015.

[28] M. A. Yokus and J. S. Jur, "Fabric-Based Wearable Dry Electrodes for Body Surface Biopotential Recording," *IEEE Trans. Biomed. Eng.*, vol. 63, no. 2, pp. 423-430, February 2016.

Example 9

Figure 36:
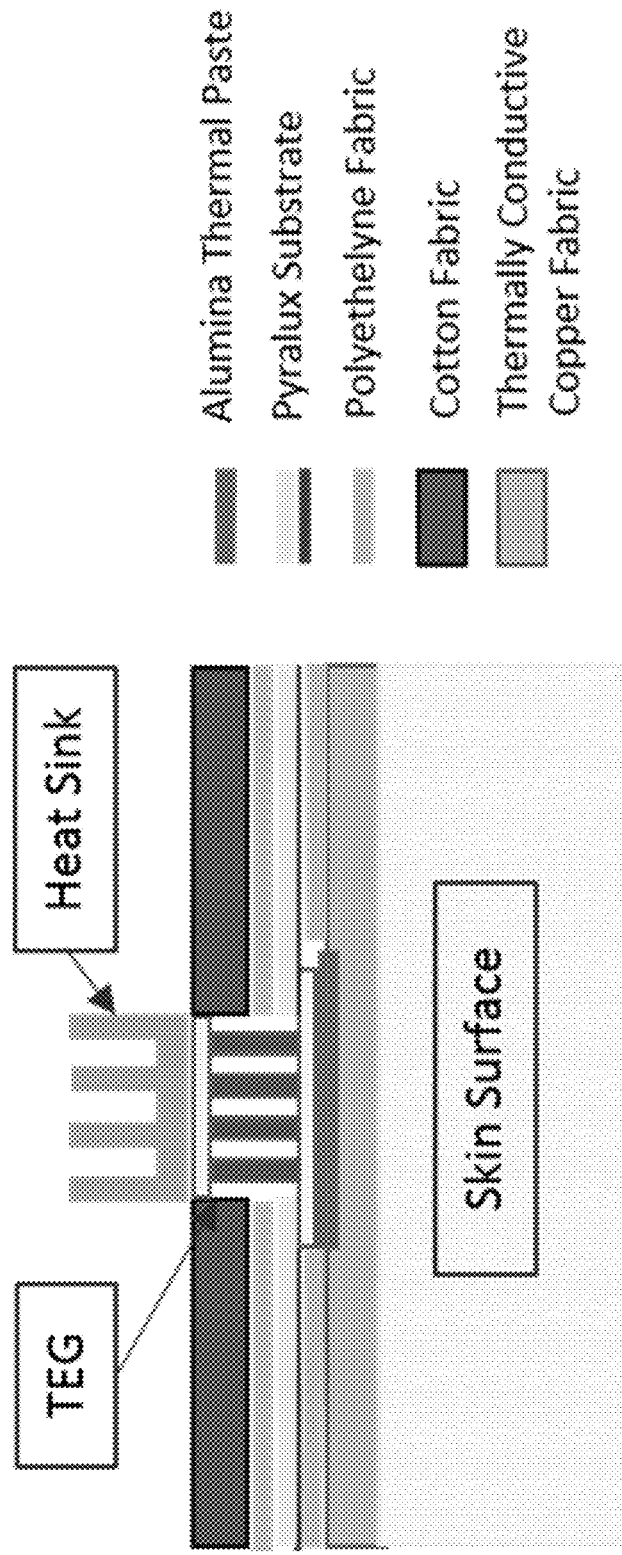
FIG. 36 shows a cross-section of some embodiments of an electronic textile having a flexible interconnect with an integrated electronic component.
Figure 37:
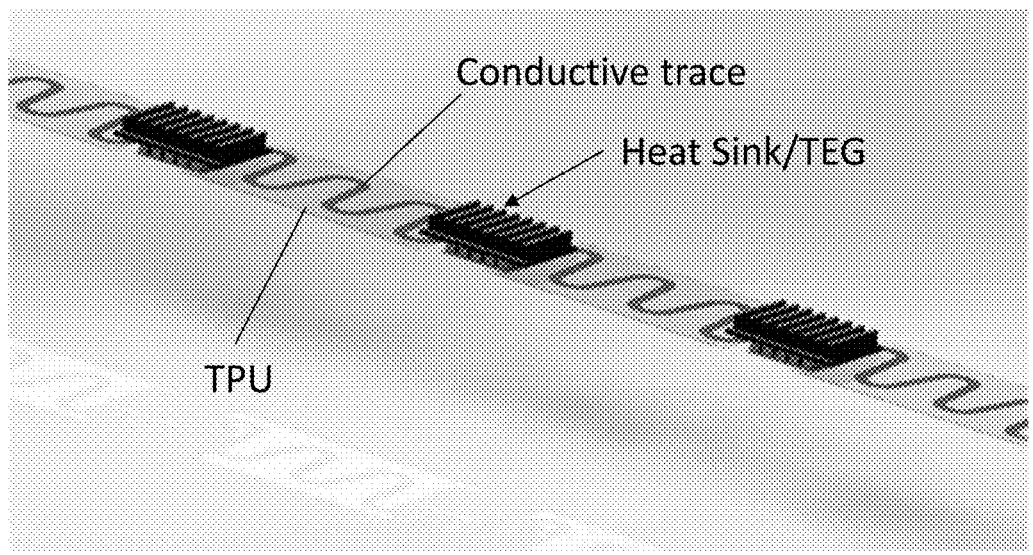
FIG. 37 shows an embodiment of a flexible interconnect with integrated thermoelectric generator (TEG) and a heat sink.
Figure 38:
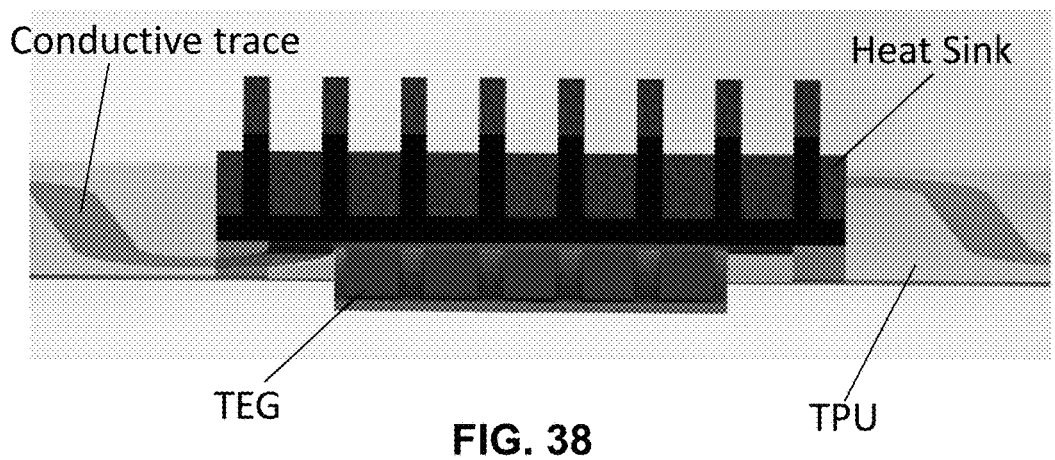
FIG. 38 shows a close-up view of the flexible interconnect of FIG. 37.

Other electronic components can be integrated into the flexible interconnect. As demonstrated in FIGS. 36-38, one or more TEGs can be incorporated into the flexible interconnect. These TEGs can use body heat from a user to provide power to other electronic components in an electronic textile, including those electronically coupled to the flexible interconnect. TEGs and/or other devices and/or electronic components can be integrated into gaps/holes cut into the polymer film or be applied directly onto the bottom TPU layer and then encapsulated. Combinations of the integration methods exist. The connections to the flexible interconnect can occur to pads from the TEG packaging header that are in direct contact with the interconnect. Similar constructions using solar cells are applicable. Heat sinks may or may not be used as necessary. In other words, heat sinks are optional. Heat sinks can also be a flexible material that is applied separately or can be embedded within the encapsulating TPU. The bottom side of the TPU can also be a heat spreader that is enabled by thermally conductive fillers situated in the underlying or adjacent TPU. The flexible interconnect and systems incorporating the flexible interconnect can have heat can flow from a larger area surrounding the TEG to the TEG.

We claim:

1. A flexible interconnect comprising:
    a first thermoplastic polymer film;
    a first hole, where the first hole in in the first thermoplastic polymer film;
    a second thermoplastic polymer film;
    a second hole, where the second hole is in the second thermoplastic polymer film;
    a conductive trace;
    a first conductive pad, where the first conductive pad is electrically coupled to the conductive trace and where the first conductive pad is in physical contact with the first hole; and
    a second conductive pad, where the second conductive pad is electrically coupled to the conductive trace and where the second conductive pad is in physical contact with the second hole,
    where the conductive trace, the first conductive pad, and the second conductive pad are encapsulated between the first thermoplastic polymer film and the second thermoplastic polymer film, and
    where the flexible interconnect is stretchable at least along a longitudinal axis that is parallel to the longitudinal axis extending from the first conductive pad and the second conductive pad.

2. The flexible interconnect of claim 1, wherein at least one of the first thermoplastic polymer film and second thermoplastic polymer film is polyurethane.

3. The flexible interconnect of claim 1, wherein the conductive trace comprises conductive ink.

4. The flexible interconnect of claim 3, wherein the conductive ink consists of at least one compound selected from the group consisting of: silver, carbon, silver chloride, gold, and combinations thereof.

5. The flexible interconnect of claim 4, wherein the conductive ink is at least one of the inks selected from the group consisting of: a dielectric ink, transparent conductive ink, a silver plated copper ink, and a positive temperature coefficient ink.

6. The flexible interconnect of claim 1, further comprising an electrical component, where the electrical component is electrically coupled to the conductive trace.

7. The flexible interconnect of claim 6, wherein the electrical component is electrically coupled to the first conductive pad or the second conductive pad.

8. The flexible interconnect of claim 6, wherein the electrical component is integrated with the conductive trace.

9. The flexible interconnect of claim 1, wherein the first thermoplastic polymer film and/or the second thermoplastic polymer film is physically attached to a textile.

10. A system comprising:
    a first flexible interconnect and a second flexible interconnect, where the first conductive pad of the first flexible interconnect is electronically coupled to the second conductive pad of the second flexible interconnect, wherein the first flexible interconnect and the second flexible interconnect each comprise:
    a first thermoplastic polymer film;
    a first hole, where the first hole in in the first thermoplastic polymer film;
    a second thermoplastic polymer film;
    a second hole, where the second hole is in the second thermoplastic polymer film;
    a conductive trace;
    a first conductive pad, where the first conductive pad is electrically coupled to the conductive trace and where the first conductive pad is in physical contact with the first hole; and
    a second conductive pad, where the second conductive pad is electrically coupled to the conductive trace and where the second conductive pad is in physical contact with the second hole,
    where the conductive trace, the first conductive pad, and the second conductive pad are encapsulated between the first thermoplastic polymer film and the second thermoplastic polymer film, and
    where the flexible interconnect is stretchable at least along a longitudinal axis that is parallel to the longitudinal axis extending from the first conductive pad and the second conductive pad.

11. The system of claim 10, wherein the first conductive pad of the first flexible interconnect is in physical contact with the second conductive pad of the second flexible interconnect.

12. The system of claim 10, wherein the first conductive pad of the first flexible interconnect is physically integrated with the second conductive pad of the second flexible interconnect.

13. The system of claim 10, further comprising a third flexible interconnect, where the second conductive pad of the first flexible interconnect is electronically coupled to the first conductive pad of the third flexible interconnect, and where the third flexible interconnect comprises:
    a first thermoplastic polymer film;
    a first hole, where the first hole in in the first thermoplastic polymer film;
    a second thermoplastic polymer film;
    a second hole, where the second hole is in the second thermoplastic polymer film;
    a conductive trace;

a first conductive pad, where the first conductive pad is electrically coupled to the conductive trace and where the first conductive pad is in physical contact with the first hole; and a second conductive pad, where the second conductive pad is electrically coupled to the conductive trace and where the second conductive pad is in physical contact with the second hole, where the conductive trace, the first conductive pad, and the second conductive pad are encapsulated between the first thermoplastic polymer film and the second thermoplastic polymer film.

14. The system of claim 13, wherein the second conductive pad of the first flexible interconnect is in physical contact with the first conductive pad of the third flexible interconnect.

15. The system of claim 13, wherein the second conductive pad of the first flexible interconnect is physically integrated with the first conductive pad of the third flexible interconnect.

16. The system of claim 10, wherein at least one of the first flexible interconnect, second flexible interconnect, and third flexible interconnect is physically attached to a textile.

17. A textile comprising:
a first thermoplastic polymer film;
a first hole, where the first hole in in the first thermoplastic polymer film;
a second thermoplastic polymer film;
a second hole, where the second hole is in the second thermoplastic polymer film;
a conductive trace;
a first conductive pad, where the first conductive pad is electrically coupled to the first conductive trace and where the first conductive pad is in physical contact with the first hole; and
a second conductive pad, where the second conductive pad is electrically coupled to the first conductive trace and where the second conductive pad is in physical contact with the second hole,
where the conductive trace, the first conductive pad, and the second conductive pad are encapsulated between the first thermoplastic polymer film and the second thermoplastic polymer film,
where the flexible interconnect is stretchable at least along a longitudinal axis that is parallel to the longitudinal axis extending from the first conductive pad and the second conductive pad, and
where the first thermoplastic polymer film and/or the second thermoplastic polymer film is physically attached to the textile.

18. The textile of claim 17, wherein at least one of the first thermoplastic polymer film and the second thermoplastic polymer film comprises polyurethane.

19. The textile of claim 17, wherein the conductive trace comprises conductive ink.

20. The textile of claim 17, wherein the textile further comprises an electrical component, where the electrical component is electrically coupled to the conductive trace.

* * * * *